United States Patent
Canich et al.

(10) Patent No.: US 9,796,795 B2
(45) Date of Patent: Oct. 24, 2017

(54) TETRAHYDROINDACENYL CATALYST COMPOSITION, CATALYST SYSTEM, AND PROCESSES FOR USE THEREOF

(71) Applicant: ExxonMobil Chemical Patents Inc., Baytown, TX (US)

(72) Inventors: Jo Ann M. Canich, Houston, TX (US); Crisita Carmen H. Atienza, Houston, TX (US); Vyatcheslav V. Izmer, Moscow (RU); Dmitry S. Kononovich, Moscow (RU); Alexander Z. Voskoboynikov, Moscow (RU)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 15/145,314

(22) Filed: May 3, 2016

(65) Prior Publication Data

US 2016/0244535 A1 Aug. 25, 2016

Related U.S. Application Data

(63) Continuation-in-part of application No. PCT/US2015/067582, filed on Dec. 28, 2015, and a continuation-in-part of application No. PCT/US2015/067586, filed on Dec. 28, 2015, and a continuation-in-part of application No. PCT/US2015/067587, filed on Dec. 28, 2015, and a continuation-in-part of application No. PCT/US2016/021751, filed on Mar. 10, 2016, and a continuation-in-part of application No. PCT/US2016/021748, filed on Mar. 10, 2016.

(60) Provisional application No. 62/103,372, filed on Jan. 14, 2015, provisional application No. 62/149,799, filed on Apr. 20, 2015, provisional application No. 62/149,814, filed on Apr. 20, 2015.

(51) Int. Cl.

| | |
|---|---|
| C07F 17/00 | (2006.01) |
| C08F 4/6592 | (2006.01) |
| C08F 10/00 | (2006.01) |
| C08F 4/76 | (2006.01) |
| C07F 7/28 | (2006.01) |
| C08F 110/02 | (2006.01) |
| C08F 110/06 | (2006.01) |
| C08F 210/02 | (2006.01) |
| C08F 4/659 | (2006.01) |

(52) U.S. Cl.
CPC .......... *C08F 4/76* (2013.01); *C07F 7/28* (2013.01); *C07F 17/00* (2013.01); *C08F 4/6592* (2013.01); *C08F 4/65912* (2013.01); *C08F 110/02* (2013.01); *C08F 110/06* (2013.01); *C08F 210/02* (2013.01); *C08F 4/65908* (2013.01); *C08F 2420/02* (2013.01)

(58) Field of Classification Search
CPC .... C07F 17/00; C08F 4/6592; C08F 4/65908; C08F 4/65912; C08F 10/00
See application file for complete search history.

(56) References Cited

U.S. PATENT DOCUMENTS

| | | | |
|---|---|---|---|
| 4,701,432 | A | 10/1987 | Welborn, Jr. |
| 5,077,255 | A | 12/1991 | Welborn, Jr. |
| 5,135,526 | A | 8/1992 | Zinnanti et al. |
| 5,382,630 | A | 1/1995 | Stehling et al. |
| 5,382,631 | A | 1/1995 | Stehling et al. |
| 5,516,848 | A | 5/1996 | Canich et al. |
| 5,965,756 | A | 10/1999 | McAdon et al. |
| 6,069,213 | A | 5/2000 | Nemzek et al. |
| 6,175,409 | B1 | 1/2001 | Nielsen et al. |
| 6,207,606 | B1 | 3/2001 | Lue et al. |
| 6,260,407 | B1 | 7/2001 | Petro et al. |
| 6,294,388 | B1 | 9/2001 | Petro |
| 6,310,164 | B1 | 10/2001 | Morizono et al. |
| 6,406,632 | B1 | 6/2002 | Safir et al. |
| 6,420,507 | B1 | 7/2002 | Kale et al. |

(Continued)

FOREIGN PATENT DOCUMENTS

| | | |
|---|---|---|
| EP | 1120424 | 8/2001 |
| WO | 98/06727 | 2/1998 |
| WO | 98/09999 | 3/1998 |
| WO | 98/27103 | 6/1998 |
| WO | 00/12565 | 3/2000 |
| WO | 01/42315 | 6/2001 |
| WO | 02/060957 | 8/2002 |
| WO | 03/025027 | 3/2003 |
| WO | 2004/013149 | 2/2004 |
| WO | 2004/046214 | 6/2004 |

(Continued)

OTHER PUBLICATIONS

Amaya, et al., "Sumanenly Metallocenes: Synthesis and Structure of Mono-and Trinuclear Zirconocene Complexes," Journal of the American Chemical Society, 2014, vol. 136 (36), pp. 12794-12798.

(Continued)

*Primary Examiner* — Caixia Lu
(74) *Attorney, Agent, or Firm* — Catherine L. Bell

(57) ABSTRACT

This invention relates to a compound represented by the formula: $T_yCp'_mMG_nX_q$ wherein: Cp' is a tetrahydroindacenyl group which may be substituted or unsubstituted, provided that when Cp' is tetrahydro-s-indacenyl: 1) the 3 and/or 4 positions are not aryl or substituted aryl, 2) the 3 position is not directly bonded to a group 15 or 16 heteroatom, 3) there are no additional rings fused to the tetrahydroindacenyl ligand, 4) T is not bonded to the 2-position, and 5) the 5, 6, or 7-position is geminally disubstituted; M is a group 3, 4, 5, or 6 transition metal; G is a heteroatom group represented by the formula $JR^i_z$ where J is N, P, O or S, $R^i$ is a $C_1$ to $C_{20}$ hydrocarbyl group, and z is 1 or 2; T is a bridging group; y is 0 or 1; X is a leaving group; m=1; n=1, 2 or 3; q=1, 2 or 3, and the sum of m+n+q is equal to the oxidation state of the transition metal.

25 Claims, 3 Drawing Sheets

(56) References Cited

U.S. PATENT DOCUMENTS

| | | |
|---|---|---|
| 6,436,292 B1 | 8/2002 | Petro |
| 6,444,764 B1 | 9/2002 | Kristen et al. |
| 6,451,724 B1 | 9/2002 | Nifant'ev et al. |
| 6,454,947 B1 | 9/2002 | Safir et al. |
| 6,461,515 B1 | 10/2002 | Safir et al. |
| 6,475,391 B2 | 11/2002 | Safir et al. |
| 6,491,816 B2 | 12/2002 | Petro |
| 6,491,823 B1 | 12/2002 | Safir et al. |
| 6,613,713 B2 | 9/2003 | Becke et al. |
| 6,646,071 B1 | 11/2003 | Klosin et al. |
| 6,656,866 B2 | 12/2003 | Wenzel et al. |
| 6,664,348 B2 | 12/2003 | Speca |
| 6,846,770 B2 | 1/2005 | Speca |
| 7,115,761 B2 | 10/2006 | Resconi et al. |
| 7,141,632 B2 | 11/2006 | Vaughan et al. |
| 7,192,902 B2 | 3/2007 | Brinen et al. |
| 7,214,745 B2 | 5/2007 | Arai et al. |
| 7,355,058 B2 | 4/2008 | Luo et al. |
| 7,385,015 B2 | 6/2008 | Holtcamp |
| 8,088,867 B2 | 1/2012 | Jiang et al. |
| 8,110,518 B2 | 2/2012 | Marin et al. |
| 8,575,284 B2 | 11/2013 | Luo et al. |
| 8,598,061 B2 | 12/2013 | Yang et al. |
| 8,815,357 B1 | 8/2014 | Inn et al. |
| 9,193,856 B2 | 11/2015 | Ebata et al. |
| 2001/0014725 A1* | 8/2001 | Becke .................. C07C 17/10 526/126 |
| 2002/0007023 A1 | 1/2002 | McDaniel et al. |
| 2004/0214953 A1 | 10/2004 | Yamada et al. |
| 2005/0288461 A1 | 12/2005 | Jensen et al. |
| 2008/0287620 A1 | 11/2008 | Ravishankar |
| 2012/0130032 A1 | 5/2012 | Hussein et al. |
| 2014/0031504 A1 | 1/2014 | Jacobsen et al. |
| 2014/0213734 A1 | 7/2014 | Jiang |
| 2014/0350189 A1* | 11/2014 | Hustad ................ C08F 297/08 525/247 |

FOREIGN PATENT DOCUMENTS

| | | |
|---|---|---|
| WO | 2005/075525 | 8/2005 |
| WO | 2007/080365 | 7/2007 |
| WO | 2012/006272 | 1/2012 |
| WO | 2015/009474 | 1/2015 |
| WO | 2015/067582 | 3/2015 |
| WO | 2016/114914 | 7/2016 |
| WO | 2016/114915 | 7/2016 |
| WO | 2016/114916 | 7/2016 |
| WO | 2016/171807 | 10/2016 |
| WO | 2016/171808 | 10/2016 |
| WO | 2016/172099 | 10/2016 |
| WO | 2017/034680 | 3/2017 |

OTHER PUBLICATIONS

Busico, et al., "*Effects of Regiochemical and Sterochemical Errors on the Course of Isotactic Propene Polyinsertion Promoted by Homogenous Ziegler—Natta Catalysts*," Macromolecules, 1994, vol. 27, pp. 7538-7543.

Grassi, et al., "*Microstructure of Isotactic Polypropylene Prepared with Homogeneous Catalysis: Steroregularity, Regioregularity*," and 1,3-Insertion, 1988, vol. 21, pp. 617-622.

Hong, et al., "*Immobilized $Me_2Si(C_5Me_4)(N\text{-}tBu)TiCl_2/(nBuCp)_2ZrCl_2$ Hybrid Metallocene Catalyst System for the Production of Poly(ethylene-co-hexene) With Pseudo-Bimodal Molecular Weight and Inverse Comonomer Distribution*," Wiley InterScience, Polymer Engineering and Science, 2007, pp. 131-139.

Iedema, et al., "*Predicting the Molecular Weight Distribution of Polyethylene for Mixed Systems with a Constrained-Geometry Metallocene Catalyst in a Semibatch Reactor*," Industrial & Engineering Chemistry Research, 2004, vol. 43, pp. 36-50.

Kim, et al., "*Copolymerization of Ethylene and α-Olefins with Combined Metallocene Catalysts. III. Production of Polyolefins with Controlled Microstructres*," Journal of Polymer Science; Part A: Polymer Chemistry, 2000, vol. 38, pp. 1427-1432.

Kociolek, et al., "*Intramolecular Thermal Cyclotrimerization of an Acyclic Triyne: An Uncatalyzed Process*," Tetrahedron Letters, 1999, vol. 40, pp. 4141-4144.

Mironov, et al, "*Effect of Chlorosilyl Groups on the Liability of Chlorine in (2-Chloroalkyl) Silanes in the Reaction of Dehydrochlorination with Quinoline*," N.D. Zelinskii Institute of Organic Chemistry Academy of Sciences USSR, 1957, pp. 1188-1194.

U.S. Appl. No. 62/149,799, filed Apr. 20, 2015.
U.S. Appl. No. 62/103,372, filed Jan. 14, 2015.
PCT/US2017/025400 filed Mar. 31, 2017 ExxonMobil Chemical Patents Inc.

\* cited by examiner

Figure 1: PP data: Mn vs. Catalyst activity at two different reactor temperatures; 0.04 μmol catalyst used.
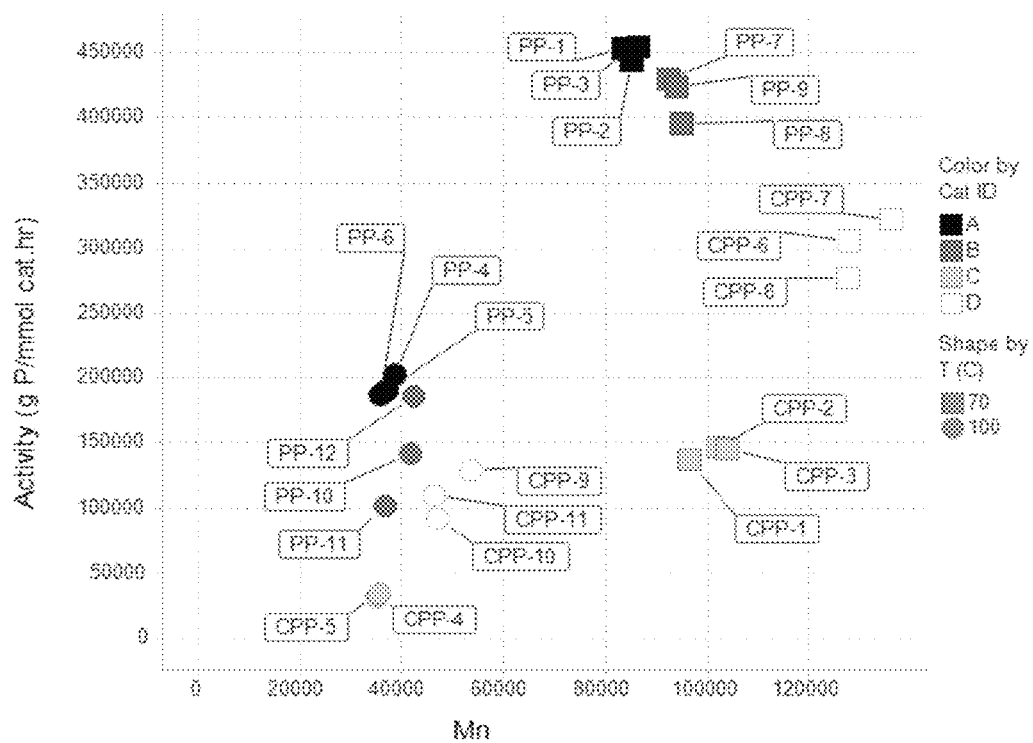

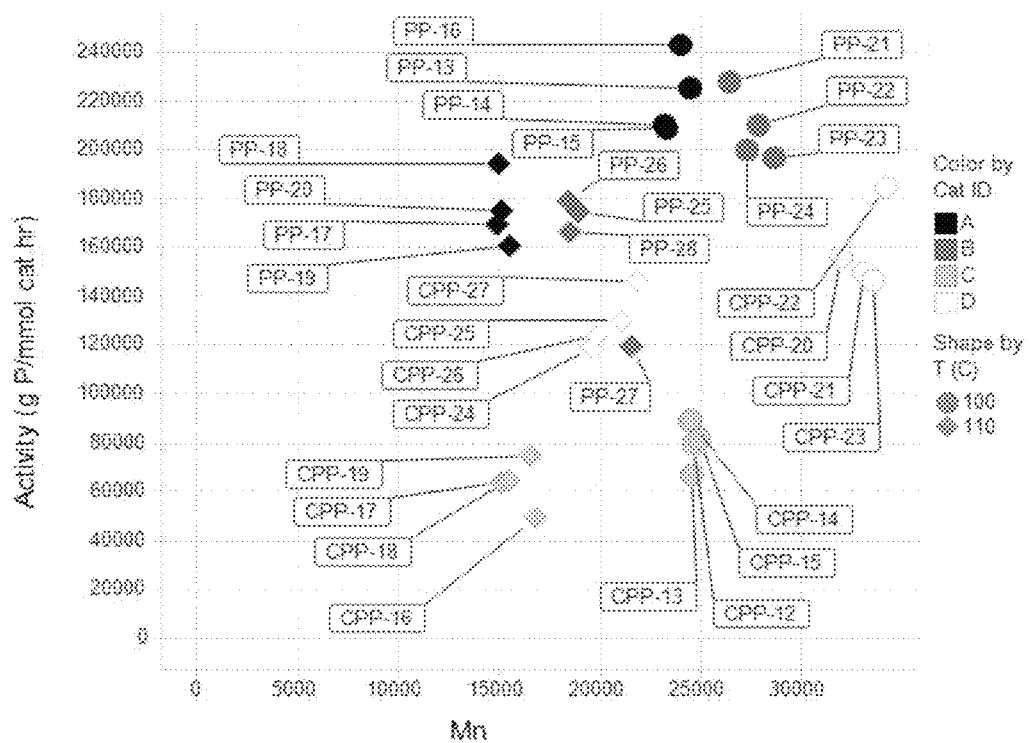
Figure 2: PP data: Mn vs. Catalyst activity at two different reactor temperatures; 0.10 µmol catalyst used at 100°C and 0.15 µmol catalyst used at 110°C

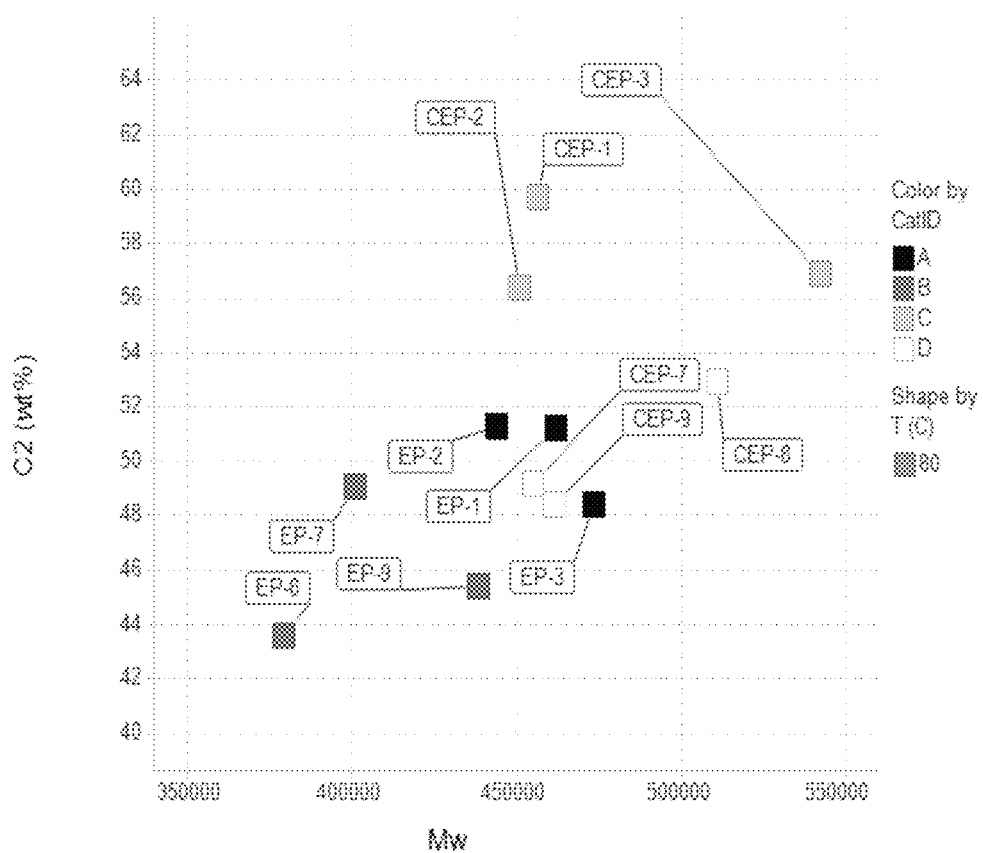
Figure 3: EP data: Mw vs. Ethylene incorporation

US 9,796,795 B2

TETRAHYDROINDACENYL CATALYST COMPOSITION, CATALYST SYSTEM, AND PROCESSES FOR USE THEREOF

STATEMENT OF RELATED CASES

This Application is a continuation in part of PCT/US2015/067582 filed Dec. 28, 2015 which claims priority to and the benefit of U.S. Ser. No. 62/103,372, filed Jan. 14, 2015.

This Application is also a continuation in part of PCT/US2015/067586 filed Dec. 28, 2015 which claims priority to and the benefit of U.S. Ser. No. 62/103,372, filed Jan. 14, 2015.

This Application is also a continuation in part of PCT/US2015/067587 filed Dec. 28, 2015 which claims priority and the benefit of U.S. Ser. No. 62/103,372, filed Jan. 14, 2015.

This Application is a continuation in part of PCT/US2016/021751, filed Mar. 10, 2016 which claims priority to and the benefit of U.S. Ser. No. 62/149,799, filed Apr. 20, 2015.

This Application is a continuation in part of PCT/US2016/021748, filed Mar. 10, 2016 which claims priority to and the benefit of U.S. Ser. No. 62/149,814, filed Apr. 20, 2015.

This application also relates to concurrently filed U.S. Ser. No. 15/145,320.

FIELD OF THE INVENTION

This invention relates to novel monocyclopentadienyl transition metal compounds, catalyst systems comprising such and polymerization process using such.

BACKGROUND OF THE INVENTION

Olefin polymerization catalysts are of great use in industry. Hence, there is interest in finding new catalyst systems that increase the commercial usefulness of the catalyst and allow the production of polymers having improved properties.

Catalysts for olefin polymerization are often based on cyclopentadienyl transition metal compounds as catalyst precursors, which are activated either with an alumoxane or with an activator containing a non-coordinating anion. A typical catalyst system includes a metallocene catalyst and an activator, and an optional support. Many metallocene catalyst systems can be used in homogeneous polymerizations (such as solution or supercritical) and supported catalyst systems are used in many polymerization processes, often in slurry or gas phase polymerization processes.

WO 2004/013149 A1 discloses group 4 metal constrained geometry complexes of tricyclic 4-aryl substituted indenyl ligands, esp. 1,5,6,7-tetrahydro-4-aryl-s-indacen-1-yl ligands, where the tetrahydro-s-indacene is substituted in the 4 position with a $C_{6-12}$ aryl group, and is preferably not substituted in the 5, 6, or 7 position, and if substituted in the 5, 6, or 7 position, is substituted by at most only one substituent at each position.

U.S. Pat. No. 6,420,507 discloses substituted tetrahydro-s-indacenyl transition metal complexes (such as Examples H to N), where the tetrahydro-s-indacene is not substituted the 5, 6, or 7 position and is substituted in the 2 and/or 3 position.

EP 1 120 424 (and family member U.S. Pat. No. 6,613,713) disclose tert-butylamino-2-(5,6,7-tetrahydro-s-indacenyldimethylsilyl)titanium dichloride indenyl ligands as polymerization catalyst where the tetrahydro-s-indacene is not substituted the 5, 6, or 7 position.

WO 2001/042315 discloses dimethylsilylene(t-butylamido)(2-methyl-tetrahydro-s-indacenyl)Ti(CH$_2$SiMe$_3$)$_2$ (see examples 27 and 28, and compounds IB5 and IB5' in claim 21) as polymerization catalysts where the tetrahydro-s-indacene is not substituted the 5, 6, or 7 position.

WO 98/27103 discloses dimethylsilylene(t-butylamido)(2-methyl-tetrahydro-s-indacenyl)TiCl$_2$ (see example 1) and others as polymerization catalysts where the tetrahydro-s-indacene is not substituted the 5, 6, or 7 position.

Other references of interest include: U.S. Pat. No. 5,382,630; U.S. Pat. No. 5,382,631; U.S. Pat. No. 8,575,284; U.S. Pat. No. 6,069,213; Kim, J. D. et al., J. Polym. Sci. Part A: Polym. Chem., 38, 1427 (2000); Iedema, P. D. et al., Ind. Eng. Chem. Res., 43, 36 (2004); U.S. Pat. No. 6,656,866; U.S. Pat. No. 8,815,357; US 2014/0031504; U.S. Pat. No. 5,135,526; U.S. Pat. No. 7,385,015; WO 2007/080365; WO2012/006272; WO2014/0242314; WO 00/12565; WO 02/060957; WO 2004/046214; U.S. Pat. No. 6,846,770; U.S. Pat. No. 6,664,348; WO 05/075525; US 2002/007023; WO 2003/025027; US 2005/0288461; US 2014/0031504; U.S. Pat. No. 8,088,867; U.S. Pat. No. 5,516,848; U.S. Pat. No. 4,701,432; U.S. Pat. No. 5,077,255; U.S. Pat. No. 7,141,632; U.S. Pat. No. 6,207,606; U.S. Pat. No. 8,598,061; Polymer Engineering and Science-2007, DOI 10.1002/pen, pages 131-139, published online in Wiley InterScience (www.interscience.wiley.com) 2007 Society of Plastics Engineers; US 2012/0130032; U.S. Pat. No. 7,192,902; U.S. Pat. No. 8,110,518; U.S. Pat. No. 9,193,856; U.S. Pat. No. 7,355,058; U.S. Ser. No. 62/149,799, filed Apr. 20, 2015 (and all cases claiming priority to or the benefit of U.S. Ser. No. 62/149,799); U.S. Ser. No. 62/103,372, filed Jan. 14, 2015 (and all cases claiming priority to or the benefit of U.S. Ser. No. 62/103,372); and PCT/US2015/067582, filed Dec. 28, 2015.

There is still a need in the art for new and improved catalyst systems for the polymerization of olefins, in order to achieve increased activity or specific polymer properties, such as high melting point, high molecular weights, to increase conversion or comonomer incorporation, or to alter comonomer distribution without deteriorating the resulting polymer's properties.

It is therefore also an object of the present invention to provide novel supported catalysts systems and processes for the polymerization of olefins using such catalyst systems.

The metallocene compounds and catalyst systems described herein address these needs by producing highly active catalysts containing a higher comonomer incorporation and molecular weight, that when formed into a molded part has improved properties (such as improved strength).

SUMMARY OF THE INVENTION

This invention relates to monocyclopentadienyl transition metal compounds represented by the formula: $T_yCp'_m\text{-}MG_nX_q$ wherein: Cp' is a tetrahydroindacenyl group (such as tetrahydro-s-indacenyl or tetrahydro-as-indacenyl) which may be substituted or unsubstituted, provided that when Cp' is tetrahydro-s-indacenyl: 1) the 3 and/or 4 positions are not aryl or substituted aryl, 2) the 3 position is not directly bonded to a group 15 or 16 heteroatom, 3) there are no additional rings fused to the tetrahydroindacenyl ligand, 4) T is not bonded to the 2-position, and 5) the 5, 6, or 7-position (preferably the 6 position) is geminally disubstituted, preferably with two $C_1$-$C_{10}$ alkyl groups;

M is a group 3, 4, 5, or 6 transition metal (preferably group 4);

G is a heteroatom group represented by the formula $JR^i_z$ where J is N, P, O or S, $R^i$ is a $C_1$ to $C_{20}$ hydrocarbyl group, and z is 2−y when J is N or P, and 1−y when J is O or S;

T is a bridging group;

y is 0 or 1, indicating the absence or presence of T;

X is a leaving group;

m=1;

n=1, 2 or 3;
q=1, 2 or 3; and
the sum of m+n+q is equal to the oxidation state of the transition metal, e.g. 3, 4, 5, or 6.

This invention also relates to a monocyclopentadienyl transition metal compound represented by the formula I:

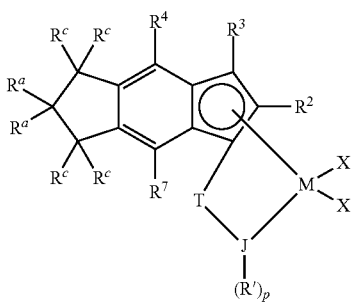

(I)

where M is a group 4 metal;
J is N, O, S or P;
p is 1 when J is N or P, and is 0 when J is O or S;
each $R^2$, $R^3$, $R^4$, and $R^7$ is independently hydrogen, or a $C_1$-$C_{50}$ substituted or unsubstituted hydrocarbyl, halocarbyl or silylcarbyl, provided that $R^3$ and/or $R^4$ are not aryl or substituted aryl;
each $R^a$ is independently a $C_1$-$C_{10}$ alkyl;
each $R^c$ is independently hydrogen or a $C_1$-$C_{10}$ alkyl, and provided that adjacent $R^4$, $R^c$, $R^a$, and or $R^7$ do not join together to form a fused ring system;
each R' is independently a $C_1$-$C_{100}$ substituted or unsubstituted hydrocarbyl, halocarbyl, or silylcarbyl;
T is $(CR^8R^9)_x$, $SiR^8R^9$ or $GeR^8R^9$ where x is 1 or 2, $R^8$ and $R^9$ are independently selected from hydrogen, or substituted or unsubstituted hydrocarbyl, halocarbyl, silylcarbyl and germylcarbyl and $R^8$ and $R^9$ may optionally be bonded together to form a ring structure;
each X is, independently, a leaving group, or two Xs are joined and bound to the metal atom to form a metallocycle ring, or two Xs are joined to form a chelating ligand, a diene ligand, or an alkylidene.

This invention also relates to a monocyclopentadienyl transition metal compound represented by the formula III:

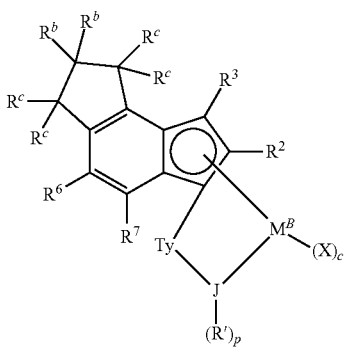

where M is group 3, 4, 5, or 6 transition metal;
B is the oxidation state of M, and is 3, 4, 5 or 6;
c is B−2;
J is N, O, S or P;
p is 2−y when J is N or P, and 1−y when J is O or S;

each $R^2$, $R^3$, $R^6$, and $R^7$, is independently hydrogen, or a $C_1$-$C_{50}$ substituted or unsubstituted hydrocarbyl, halocarbyl or silylcarbyl;
each $R^b$ and $R^c$ is independently $C_1$-$C_{10}$ alkyl, or hydrogen;
each R' is, independently, a $C_1$-$C_{100}$ substituted or unsubstituted hydrocarbyl, halocarbyl, silylcarbyl or germycarbyl;
T is $(CR^8R^9)_x$, $SiR^8R^9$ or $GeR^8R^9$ where x is 1 or 2, $R^8$ and $R^9$ are independently selected from hydrogen, substituted or unsubstituted hydrocarbyl, halocarbyl, silylcarbyl and germylcarbyl, and $R^8$ and $R^9$ may optionally be bonded together to form a ring structure;
y is 0 or 1, indicating the absence or presence of T;
each X is, independently, a leaving group, or two Xs are joined and bound to the metal atom to form a metallocycle ring, or two Xs are joined to form a chelating ligand, a diene ligand, or an alkylidene.

This invention also relates to a catalyst system comprising the bridged monocyclopentadienyl transition metal compound and an activator.

This invention also relates to a process to produce olefin polymer comprising: i) contacting olefin and optional $C_2$ to $C_{20}$ comonomer with a catalyst system comprising activator and a bridged monocyclopentadienyl transition metal compound described above, and ii) obtaining an olefin polymer.

This invention also relates to metallocene catalyst compositions comprising the reaction product of: (1) one or more bridged metallocenes described above; (2) one or more activators.

This invention further relates to polymer compositions produced by the methods described herein.

BRIEF DESCRIPTION OF THE DRAWINGS

FIG. 1 is a graph of polypropylene data from the Experimental section comparing polymer Mn vs. catalyst activity at two different reactor temperatures and at a catalyst content of 0.04 μmol.

FIG. 2 is a graph of polypropylene data: polymer Mn vs. Catalyst activity at two different reactor temperatures; 0.10 μmol catalyst used at 100° C. and 0.15 μmol catalyst used at 110° C.

FIG. 3 is a graph of polymer molecular weight vs. ethylene incorporation for ethylene-propylene copolymers.

DETAILED DESCRIPTION OF THE INVENTION

For the purposes of this invention and the claims thereto, the new numbering scheme for the Periodic Table Groups is used as described in CHEMICAL AND ENGINEERING NEWS, 63(5), pg. 27 (1985), e.g., a "Group 4 metal" is an element from Group 4 of the Periodic Table, e.g. Hf, Ti, or Zr.

An "olefin," alternatively referred to as "alkene," is a linear, branched, or cyclic compound of carbon and hydrogen having at least one carbon-carbon double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

For the purposes of this invention, ethylene shall be considered an α-olefin.

The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be a radical, which contains hydrogen atoms and up to 50 carbon atoms and which may be linear, branched, or cyclic, and when cyclic, aromatic or non-aromatic.

Substituted hydrocarbyl radicals are radicals in which at least one hydrogen atom has been substituted with at least one functional group such as $NR^x{}_2$, $OR^x$, $SeR^x$, $TeR^x$, $PR^x{}_2$, $AsR^x{}_2$, $SbR^x{}_2$, $SR^x$, $BR^x$ and the like or where at least one non-hydrocarbon atom or group has been inserted within the hydrocarbyl radical, such as —O—, —S—, —Se—, —Te—, —N($R^x$)—, =N—, —P($R^x$)—, =P—, —As($R^x$)—, =As—, —Sb($R^x$)—, =Sb—, —B($R^x$)—, =B— and the like, where $R^x$ is independently a hydrocarbyl or halocarbyl radical, and two or more $R^x$ may join together to form a substituted or unsubstituted saturated, partially unsaturated or aromatic cyclic or polycyclic ring structure. Examples of a substituted hydrocarbyls would include —CH$_2$CH$_2$—O—CH$_3$ and —CH$_2$—NMe$_2$ where the radical is bonded via the carbon atom, but would not include groups where the radical is bonded through the heteroatom such as —OCH$_2$CH$_3$ or —NMe$_2$.

Silylcarbyl radicals are radicals in which one or more hydrocarbyl hydrogen atoms have been substituted with at least one $SiR^*{}_3$ containing group or where at least one —Si(R*)$_2$— has been inserted within the hydrocarbyl radical where R* is independently a hydrocarbyl or halocarbyl radical, and two or more R* may join together to form a substituted or unsubstituted saturated, partially unsaturated or aromatic cyclic or polycyclic ring structure.

Substituted silylcarbyl radicals are radicals in which at least one hydrogen atom has been substituted with at least one functional group such as $NR^*{}_2$, OR*, SeR*, TeR*, $PR^*{}_2$, $AsR^*{}_2$, $SbR^*{}_2$, SR*, $BR^*{}_2$, $GeR^*{}_3$, $SnR^*{}_3$, $PbR^*{}_3$ and the like or where at least one non-hydrocarbon atom or group has been inserted within the silylcarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure. Substituted silylcarbyl radicals are only bonded via a carbon or silicon atom.

Germylcarbyl radicals are radicals in which one or more hydrocarbyl hydrogen atoms have been substituted with at least one $GeR^*{}_3$ containing group or where at least one —Ge(R*)$_2$— has been inserted within the hydrocarbyl radical where R* independently a hydrocarbyl or halocarbyl radical, and two or more R* may join together to form a substituted or unsubstituted saturated, partially unsaturated or aromatic cyclic or polycyclic ring structure. Substituted germylcarbyl radicals are only bonded via a carbon or germanium atom.

Substituted germylcarbyl radicals are radicals in which at least one hydrogen atom has been substituted with at least one functional group such as $NR^*{}_2$, OR*, SeR*, TeR*, $PR^*{}_2$, $AsR^*{}_2$, $SbR^*{}_2$, SR*, $BR^*{}_2$, $SiR^*{}_3$, $SnR^*{}_3$, $PbR^*{}_3$ and the like or where at least one non-hydrocarbon atom or group has been inserted within the germylcarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g. F, Cl, Br, I) or halogen-containing group (e.g. CF$_3$).

Substituted halocarbyl radicals are radicals in which at least one halocarbyl hydrogen or halogen atom has been substituted with at least one functional group such as $NR^*{}_2$, OR*, SeR*, TeR*, $PR^*{}_2$, $AsR^*{}_2$, $SbR^*{}_2$, SR*, $BR^*{}_2$ and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure. Substituted halocarbyl radicals are only bonded via a carbon atom.

A heteroatom is an atom other than carbon or hydrogen.

The term "aryl" or "aryl group" means a monocyclic or polycyclic aromatic ring and the substituted variants thereof, including but not limited to, phenyl, naphthyl, 2-methylphenyl, xylyl, 4-bromo-xylyl. Likewise "heteroaryl" means an aryl group where a ring carbon atom (or two or three ring carbon atoms) has been replaced with a heteroatom, such as N, O, or S. The term "substituted aryl" means: 1) an aryl group where a hydrogen has been replaced by a substituted or unsubstituted hydrocarbyl group, a substituted or unsubstituted halocarbyl group, a substituted or unsubstituted silylcarbyl group, or a substituted or unsubstituted germylcarbyl group. The term"substituted heteroaryl" means: 1) a heteroaryl group where a hydrogen has been replaced by a substituted or unsubstituted hydrocarbyl group, a substituted or unsubstituted halocarbyl group, a substituted or unsubstituted silylcarbyl group, or a substituted or unsubstituted germylcarbyl group.

For nomenclature purposes, the following numbering schemes are used for indenyl, tetrahydro-s-indacenyl and tetrahydro-as-indacenyl ligands.

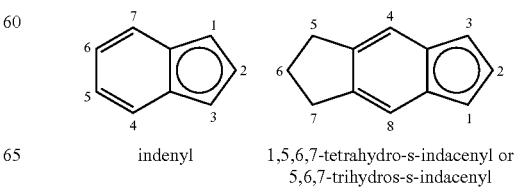

indenyl    1,5,6,7-tetrahydro-s-indacenyl or
           5,6,7-trihydros-s-indacenyl -continued 3,6,7,8-trihydro-as-indacenyl or
6,7,8-trihydro-as-indacenyl As used herein, Mn is number average molecular weight, Mw is weight average molecular weight, and Mz is z average molecular weight, wt % is weight percent, and mol % is mole percent. Molecular weight distribution (MWD), also referred to as polydispersity, is defined to be Mw divided by Mn. Unless otherwise noted, all molecular weight units (e.g., Mw, Mn, Mz) are g/mol. The following abbreviations may be used herein: Me is methyl, Et is ethyl, Pr is propyl, cPr is cyclopropyl, nPr is n-propyl, iPr is isopropyl, Bu is butyl, nBu is normal butyl, iBu is isobutyl, sBu is sec-butyl, tBu is tert-butyl, Oct is octyl, Ph is phenyl, Bn is benzyl, Cp is cyclopentadienyl, Ind is indenyl, Flu is fluorenyl, and MAO is methylalumoxane.

For purposes of this invention and the claims thereto, a "catalyst system" is the combination of at least one catalyst compound, at least one activator, an optional co-activator, and an optional support material. For the purposes of this invention and the claims thereto, when catalyst systems are described as comprising neutral stable forms of the components, it is well understood by one of ordinary skill in the art, that the ionic form of the component is the form that reacts with the monomers to produce polymers.

In the description herein, the metallocene catalyst may be described as a catalyst precursor, a pre-catalyst compound, metallocene catalyst compound or a transition metal compound, and these terms are used interchangeably.

A metallocene catalyst is defined as an organometallic transition metal compound with at least one π-bound cyclopentadienyl moiety (or substituted cyclopentadienyl moiety) bound to a transition metal.

For purposes of this invention and claims thereto in relation to metallocene catalyst compounds, the term "substituted" means that one or more hydrogen atoms have been replaced with a hydrocarbyl, heteroatom (such as a halide), or a heteroatom containing group, (such as silylcarbyl, germylcarbyl, halocarbyl, etc.). For example, methyl cyclopentadiene (Cp) is a Cp group substituted with a methyl group.

For purposes of this invention and claims thereto, "alkoxides" include those where the alkyl group is a $C_1$ to $C_{10}$ hydrocarbyl. The alkyl group may be straight chain, branched, or cyclic. The alkyl group may be saturated or unsaturated. In some embodiments, the alkyl group may comprise at least one aromatic group.

Embodiments

This invention relates to mono-tetrahydroindacenyl metallocene catalyst compounds, catalyst systems comprising such compounds and an optional support and polymerization processes using such.

This invention relates to monocyclopentadienyl group 4 transition metal compounds represented by the formula: $T_y Cp'_m MG_n X_q$
wherein Cp' is a tetrahydroindacenyl group (such as tetrahydro-s-indacenyl or tetrahydro-as-indacenyl) which may be substituted or unsubstituted, provided that when Cp' is tetrahydro-s-indacenyl: 1) the 3 and/or 4 positions are not aryl or substituted aryl, 2) the 3 position is not directly bonded to a group 15 or 16 heteroatom, 3) there are no additional rings fused to the tetrahydroindacenyl ligand, 4) T is not bonded to the 2-position, and 5) the 5, 6, or 7-position (preferably the 6 position) is geminally disubstituted, preferably with two $C_1$-$C_{10}$ alkyl groups;

M is a group 3, 4, 5, or 6 transition metal, preferably group 4 transition metal, for example titanium, zirconium, or hafnium (preferably titanium);

G is a heteroatom group represented by the formula $JR^i_z$ where J is N, P, O or S, $R^i$ is a $C_1$ to $C_{20}$ hydrocarbyl group, and z is 2−y when J is N or P, and 1−y when J is O or S (preferably J is N and z is 1);

T is a bridging group (such as dialkylsilylene or dialkylcarbylene); T is preferably $(CR^8R^9)_x$, $SiR^8R^9$ or $GeR^8R^9$ where x is 1 or 2, $R^8$ and $R^9$ are independently selected from substituted or unsubstituted hydrocarbyl, halocarbyl, silylcarbyl and germylcarbyl and $R^8$ and $R^9$ may optionally be bonded together to form a ring structure, and in a particular embodiment, $R^8$ and $R^9$ are not aryl);

y is 0 or 1, indicating the absence or presence of T;

X is a leaving group (such as a halide, a hydride, an alkyl group, an alkenyl group or an arylalkyl group);

m=1; n=1, 2 or 3; q=1, 2 or 3; and the sum of m+n+q is equal to the oxidation state of the transition metal (preferably 3, 4, 5, or 6, preferably 4); preferably m=1, n=1, q is 2, and y=1.

This invention relates to a catalyst system comprising an activator, and at least one metallocene catalyst compound, where the metallocene is a tetrahydroindacenyl group 4 transition metal compound, preferably represented by the formula: $T_y Cp'_m MG_n X_q$ wherein Cp' is a tetrahydroindacenyl group (such as tetrahydro-s-indacenyl or tetrahydro-as-indacenyl) which may be substituted or unsubstituted, provided that when Cp' is tetrahydro-s-indacenyl: 1) the 3 and/or 4 positions are not aryl or substituted aryl, 2) the 3 position is not directly bonded to a group 15 or 16 heteroatom, 3) there are no additional rings fused to the tetrahydroindacenyl ligand, 4) T is not bonded to the 2-position, and 5) the 5, 6, or 7-position (preferably the 6 position) is geminally disubstituted, preferably with two $C_1$-$C_{10}$ alkyl groups;

M is a group 3, 4, 5, or 6 transition metal, preferably group 4 transition metal, for example titanium, zirconium, or hafnium (preferably titanium);

G is a heteroatom group represented by the formula $JR^i_z$ where J is N, P, O or S, $R^i$ is a $C_1$ to $C_{20}$ hydrocarbyl group, and z is 2−y when J is N or P, and 1−y when J is O or S (preferably J is N and z is 1);

T is a bridging group (such as dialkylsilylene or dialkylcarbylene); T is preferably $(CR^8R^9)_x$, $SiR^8R^9$ or $GeR^8R^9$ where x is 1 or 2, $R^8$ and $R^9$ are independently selected from substituted or unsubstituted hydrocarbyl, halocarbyl, silylcarbyl and germylcarbyl and $R^8$ and $R^9$ may optionally be bonded together to form a ring structure, and in a particular embodiment, $R^8$ and $R^9$ are not aryl);

y is 0 or 1, indicating the absence or presence of T;

X is a leaving group (such as a halide, a hydride, an alkyl group, an alkenyl group or an arylalkyl group);

m=1; n=1, 2 or 3; q=1, 2 or 3; and the sum of m+n+q is equal to the oxidation state of the transition metal (preferably 3, 4, 5, or 6, preferably 4); preferably m=1, n=1, q is 2, and y=1.

In any embodiment of the invention described herein, each $R^i$ is a linear, branched or cyclic $C_1$ to $C_{20}$ hydrocarbyl group, preferably independently selected from the group consisting of methyl, ethyl, propyl, butyl, pentyl, hexyl, heptyl, octyl, nonyl, decyl, and isomers thereof, preferably t-butyl and or cyclododecyl.

Catalyst Compounds

This invention relates to mono-tetrahydro-s-indacenyl group 4 transition metal compounds represented by the formula I or II:

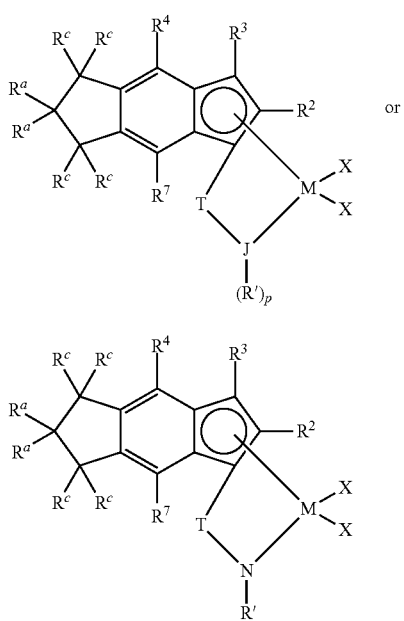

(I)

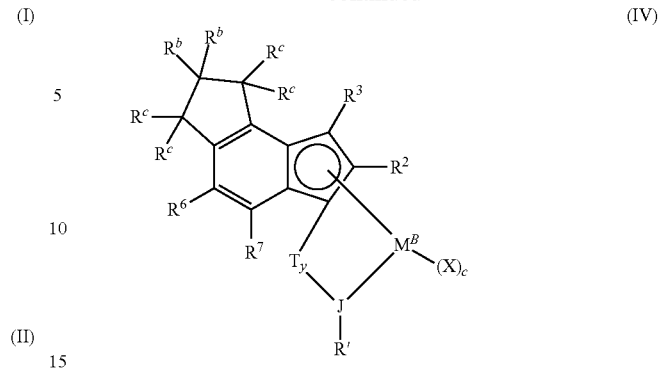

(IV)

(II)

where M is group 3, 4, 5, or 6 transition metal;
B is the oxidation state of M, and is 3, 4, 5 or 6;
c is B−2;
J is N, O, S or P;
p is 2−y when J is N or P, and 1−y when J is O or S;
each $R^2$, $R^3$, $R^6$, and $R^7$, is independently hydrogen, or a $C_1$-$C_{50}$ substituted or unsubstituted hydrocarbyl, halocarbyl or silylcarbyl;
each $R^b$ and $R^c$ is independently $C_1$-$C_{10}$ alkyl, or hydrogen;
each R' is, independently, a $C_1$-$C_{100}$ substituted or unsubstituted hydrocarbyl, halocarbyl, silylcarbyl or germycarbyl;
T is $(CR^8R^9)_x$, $SiR^8R^9$ or $GeR^8R^9$ where x is 1 or 2, $R^8$ and $R^9$ are independently selected from hydrogen, substituted or unsubstituted hydrocarbyl, halocarbyl, silylcarbyl and germylcarbyl, and $R^8$ and $R^9$ may optionally be bonded together to form a ring structure;
y is 1 when T is present and y is 0 when T is absent; and
each X is, independently, a leaving group, or two Xs are joined and bound to the metal atom to form a metallocycle ring, or two Xs are joined to form a chelating ligand, a diene ligand, or an alkylidene.

where M is a group 4 metal (such as Hf, Ti or Zr, preferably Ti);
J is N, O, S or P (preferably N and p=1);
p is 1 when J is N or P, and is 0 when J is O or S;
each $R^a$ is independently $C_1$-$C_{10}$ alkyl;
each $R^c$ is independently hydrogen or a $C_1$-$C_{10}$ alkyl;
each $R^2$, $R^3$, $R^4$, and $R^7$ is independently hydrogen, or a $C_1$-$C_{50}$ substituted or unsubstituted hydrocarbyl, halocarbyl, silylcarbyl or germylcarbyl, provided that: 1) $R^3$ and/or $R^4$ are not aryl or substituted aryl, 2) $R^3$ is not directly bonded to a group 15 or 16 heteroatom, and 3) adjacent $R^4$, $R^c$, $R^a$ or $R^7$ do not join together to form a fused ring system;
each R' is, independently, a $C_1$-$C_{100}$ substituted or unsubstituted hydrocarbyl, halocarbyl, silylcarbyl or germylcarbyl; T is $(CR^8R^9)_x$, $SiR^8R^9$ or $GeR^8R^9$ where x is 1 or 2, $R^8$ and $R^9$ are independently selected from substituted or unsubstituted hydrocarbyl, halocarbyl, silylcarbyl and germylcarbyl and $R^8$ and $R^9$ may optionally be bonded together to form a ring structure;
each X is, independently, a leaving group, or two Xs are joined and bound to the metal atom to form a metallocycle ring, or two Xs are joined to form a chelating ligand, a diene ligand, or an alkylidene.

This invention also relates to bridged mono-tetrahydro-as-indacenyl transition metal compounds represented by the formula A or B:

(A)

This invention also relates to bridged mono-tetrahydro-as-indacenyl transition metal compounds represented by the formula III or IV:

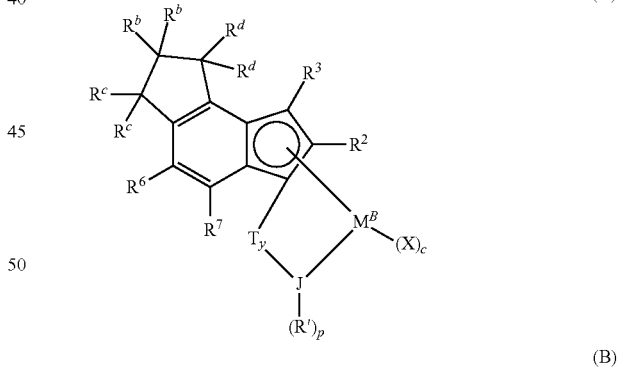

(III)

(B)

where M, B, c, J, p, $R^2$, $R^3$, $R^6$, $R^7$, R', T, y and X are as defined above for formula III and IV and each $R^b$, $R^c$, and $R^d$ is independently $C_1$-$C_{10}$ alkyl, or hydrogen, provided that both $R^b$, both $R^c$, or both $R^d$ are not hydrogen. In any embodiment of the invention described herein, $R^d$ is independently selected from the group consisting of hydrogen, methyl, ethyl, propyl, butyl, pentyl, hexyl, heptyl, octyl, nonyl, decyl, and isomers thereof, preferably hydrogen or methyl.

This invention also relates to bridged monoindacenyl group 4 transition metal compounds represented by the formula V or VI:

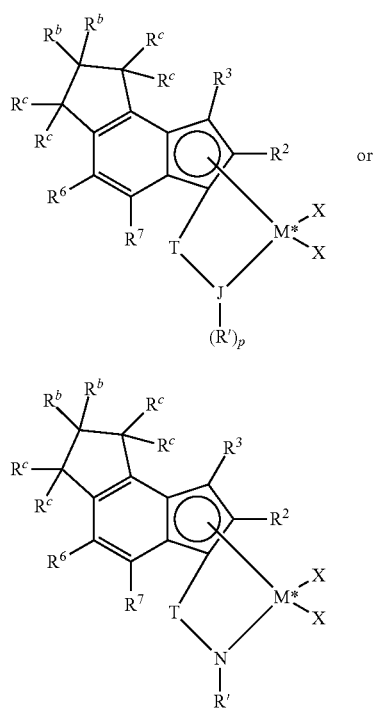

where M* is a group 4 transition metal (such as Hf, Zr or Ti);
J is N, O, S or P (preferably J is N and p is 1);
p is 2−y when J is N or P, and 1−y when J is O or S,
each $R^2$, $R^3$, $R^6$, and $R^7$ is independently hydrogen, or a $C_1$-$C_{50}$ substituted or unsubstituted hydrocarbyl, halocarbyl, silylcarbyl or germycarbyl;
each $R^b$ and each $R^c$ is independently a $C_1$-$C_{10}$ alkyl or hydrogen;
each R' is, independently, a $C_1$-$C_{100}$ substituted or unsubstituted hydrocarbyl, halocarbyl, silylcarbyl or germylcarbyl;
T is $(CR^8R^9)_x$, $SiR^8R^9$ or $GeR^8R^9$ where x is 1 or 2, $R^8$ and $R^9$ are independently selected from substituted or unsubstituted hydrocarbyl, halocarbyl, silylcarbyl and germylcarbyl and
$R^8$ and $R^9$ may optionally be bonded together to form a ring structure;
y is 1 when T is present and y is 0 when T is absent; and
each X is, independently, a leaving group, or two Xs are joined and bound to the metal atom to form a metallocycle ring, or two Xs are joined to form a chelating ligand, a diene ligand, or an alkylidene.

In a particularly useful embodiment of formula (V) and/or (VI), M* is a group 4 metal (such as Hf, Zr or Ti); J is nitrogen; each $R^2$, $R^3$, $R^6$, and $R^7$ is independently hydrogen, or a $C_1$-$C_{20}$ substituted or unsubstituted hydrocarbyl, halocarbyl, silylcarbyl or germycarbyl; each $R^b$ and each $R^c$ is independently $C_1$-$C_{10}$ alkyl (such as methyl, ethyl, propyl, butyl, pentyl, hexyl, heptyl, octyl, nonyl, decyl, or an isomer thereof), or hydrogen; R' is a $C_1$-$C_{20}$ substituted or unsubstituted hydrocarbyl, halocarbyl, silylcarbyl or germylcarbyl; T is $(CR^8R^9)_x$, $SiR^8R^9$ or $GeR^8R^9$ where x is 1 or 2, $R^8$ and $R^9$ are independently selected from substituted or unsubstituted hydrocarbyl, halocarbyl, silylcarbyl and germylcarbyl, y is 1, and $R^8$ and $R^9$ may optionally be bonded together to form a ring structure; each X is halogen or a $C_1$ to $C_{20}$ hydrocarbyl wherein the hydrocarbyls are optionally joined to form a chelating ligand, a diene, or an alkylidene.

In any embodiment of the invention described herein, M and/or M* are a group 4 metal, preferably titanium.

In any embodiment of the invention described herein, $R^3$ is not substituted with a group 15 or 16 heteroatom.

In any embodiment of the invention described herein, each $R^2$, $R^3$, $R^4$, $R^6$, and $R^7$ is independently hydrogen, or a $C_1$-$C_{50}$ substituted or unsubstituted hydrocarbyl, halocarbyl, silylcarbyl or germylcarbyl, preferably methyl, ethyl, propyl, butyl, pentyl, hexyl, heptyl, octyl, nonyl, decyl, undecyl, and dodecyl or an isomer thereof.

In any embodiment of the invention described herein, each $R^a$ is independently selected from the group consisting of methyl, ethyl, propyl, butyl, pentyl, hexyl, heptyl, octyl, nonyl, decyl, and isomers thereof, preferably methyl and ethyl, preferably methyl.

In any embodiment of the invention described herein, $R^b$ is independently selected from the group consisting of hydrogen, methyl, ethyl, propyl, butyl, pentyl, hexyl, heptyl, octyl, nonyl, decyl, and isomers thereof, preferably methyl and ethyl, preferably methyl.

In any embodiment of the invention described herein, $R^c$ is independently selected from the group consisting of hydrogen, methyl, ethyl, propyl, butyl, pentyl, hexyl, heptyl, octyl, nonyl, decyl, and isomers thereof, preferably hydrogen or methyl.

In any embodiment of the invention described herein, R' is a $C_1$-$C_{100}$ substituted or unsubstituted hydrocarbyl, halocarbyl, or silylcarbyl, preferably methyl, ethyl, propyl, butyl, pentyl, hexyl, heptyl, octyl, nonyl, decyl, undecyl, dodecyl or an isomer thereof, preferably t-butyl, neopentyl, cyclohexyl, cyclooctyl, cyclododecyl, adamantyl, or norbornyl.

In any embodiment of the invention described herein, T is $CR^8R^9$, $R^8R^9C-CR^8R^9$, $SiR^8R^9$ or $GeR^{8*}R^{9*}$ where $R^8$ and $R^9$ are independently selected from substituted or unsubstituted hydrocarbyl, halocarbyl, silylcarbyl and $R^8$ and $R^9$ may optionally be bonded together to form a ring structure, preferably each $R^8$ and $R^9$ is independently methyl, ethyl, propyl, butyl, pentyl, hexyl, heptyl, octyl, nonyl, decyl, benzyl, phenyl, methylphenyl or an isomer thereof, preferably methyl, ethyl, propyl, butyl, or hexyl.

In any embodiment of the invention described herein, at least one of $R^8$ or $R^9$ is not aryl. In any embodiment of the invention described herein, $R^8$ is not aryl. In any embodiment of the invention described herein, $R^9$ is not aryl. In any embodiment of the invention described herein, $R^8$ and $R^9$ are not aryl.

In any embodiment of the invention described herein, $R^8$ and $R^9$ are independently $C_1$-$C_{10}$ alkyls, preferably methyl, ethyl, propyl, butyl, pentyl, hexyl, heptyl, octyl, nonyl, decyl, or an isomer thereof.

In any embodiment of the invention described herein, each $R^2$, $R^3$, $R^4$, and $R^7$ is independently hydrogen or hydrocarbyl. In any embodiment of the invention described herein, each $R^2$, $R^3$, $R^6$, and $R^7$ is independently hydrogen or hydrocarbyl.

In any embodiment of the invention described herein, each $R^2$, $R^3$, $R^4$, and $R^7$ is independently hydrogen or a $C_1$-$C_{10}$ alkyl, preferably methyl, ethyl, propyl, butyl, pentyl, hexyl, heptyl, octyl, nonyl, decyl, or an isomer thereof.

In any embodiment of the invention described herein, each $R^2$, $R^3$, $R^6$, and $R^7$ is independently hydrogen or a $C_1$-$C_{10}$ alkyl, preferably methyl, ethyl, propyl, butyl, pentyl, hexyl, heptyl, octyl, nonyl, decyl, or an isomer thereof.

In any embodiment of the invention described herein, $R^2$ is a $C_1$-$C_{10}$ alkyl and $R^3$, $R^4$, and $R^6$ are hydrogen. In any embodiment of the invention described herein, $R^2$ is a $C_1$-$C_{10}$ alkyl and $R^3$, $R^6$, and $R^7$ are hydrogen.

In any embodiment of the invention described herein, $R^2$, $R^3$, $R^4$, and $R^6$ are hydrogen.

In any embodiment of the invention described herein, $R^2$, $R^3$, $R^6$, and $R^7$ are hydrogen.

In any embodiment of the invention described herein, $R^2$ is methyl, ethyl, or an isomer of propyl, butyl, pentyl or hexyl, and $R^3$, $R^4$, and $R^7$ are hydrogen. In any embodiment of the invention described herein, $R^2$ is methyl, ethyl, or an isomer of propyl, butyl, pentyl or hexyl, and $R^3$, $R^6$, and $R^7$ are hydrogen.

In any embodiment of the invention described herein, $R^2$ is methyl and $R^3$, $R^4$, and $R^7$ are hydrogen. In any embodiment of the invention described herein, $R^2$ is methyl and $R^3$, $R^6$, and $R^7$ are hydrogen.

In any embodiment of the invention, $R^3$ is hydrogen.

In any embodiment of the invention, $R^2$ is hydrogen.

In any embodiment of the invention described herein, R' is $C_1$-$C_{100}$ or $C_1$-$C_{30}$ substituted or unsubstituted hydrocarbyl.

In any embodiment of the invention described herein, R' is $C_1$-$C_{30}$ substituted or unsubstituted alkyl (linear, branched, or cyclic), aryl, alkaryl, or heterocyclic group.

In any embodiment of the invention described herein, R' is $C_1$-$C_{30}$ linear, branched or cyclic alkyl group.

In any embodiment of the invention described herein, R' is methyl, ethyl, or any isomer of propyl, butyl, pentyl, hexyl, heptyl, octyl, nonyl, decyl, undecyl, or dodecyl.

In any embodiment of the invention described herein, R' is a cyclic or polycyclic hydrocarbyl.

In any embodiment of the invention described herein, R' is selected from tert-butyl, neopentyl, cyclohexyl, cycloheptyl, cyclooctyl, cyclononyl, cyclodecyl, cycloundecyl, cyclododecyl, adamantyl, and norbornyl.

In any embodiment of the invention described herein, $R^i$ is selected from tert-butyl, neopentyl, cyclohexyl, cycloheptyl, cyclooctyl, cyclononyl, cyclodecyl, cycloundecyl, cyclododecyl, adamantyl, and norbornyl.

In any embodiment of the invention described herein, T is selected from diphenylmethylene, dimethylmethylene, 1,2-ethylene, cyclotrimethylenesilylene, cyclotetramethylenesilylene, cyclopentamethylenesilylene, dimethylsilylene, diethylsilylene, methylethylsilylene, and dipropylsilylene.

In any embodiment of the invention described herein, each $R^a$ is independently methyl, ethyl, propyl, butyl, pentyl or hexyl.

In any embodiment of the invention described herein, each $R^a$ is independently methyl or ethyl.

In any embodiment of the invention described herein, each $R^a$ is methyl.

In any embodiment of the invention described herein, each $R^b$ is independently hydrogen, methyl, ethyl, propyl, butyl, pentyl or hexyl.

In any embodiment of the invention described herein, each $R^b$ and each $R^c$ is independently hydrogen, methyl, ethyl, propyl, butyl, pentyl or hexyl.

In any embodiment of the invention described herein, each $R^b$ is independently hydrogen, methyl or ethyl.

In any embodiment of the invention described herein, each $R^b$ is methyl.

In any embodiment of the invention described herein, each X is hydrocarbyl, halocarbyl, or substituted hydrocarbyl or halocarbyl.

In any embodiment of the invention described herein, X is methyl, benzyl, or halo where halo includes fluoro, chloro, bromo and iodido.

In any embodiment of formula I or II described herein: 1) $R^3$ and/or $R^4$ are not aryl or substituted aryl, 2) $R^3$ is not directly bonded to a group 15 or 16 heteroatom, and 3) adjacent $R^4$, $R^c$, $R^a$ or $R^7$ do not join together to form a fused ring system, and 4) each $R^a$ is a C1 to C10 alkyl (preferably methyl, ethyl, propyl, butyl, pentyl, hexyl, heptyl, octyl, nonyl, decyl, or an isomer thereof).

Useful catalysts also include compounds represented by the formula VII:

$$T_y Cp'_m M G_n X_q$$

wherein Cp' is a tetrahydroindacenyl group (such as tetrahydro-s-indacenyl or tetrahydro-as-indacenyl) which may be substituted or unsubstituted, provided that when Cp' is tetrahydro-s-indacenyl: 1) the 3 and/or 4 positions are not aryl or substituted aryl, 2) the 3 position is not directly bonded to a group 15 or 16 heteroatom, 3) there are no additional rings fused to the tetrahydroindacenyl ligand, 4) T is not bonded to the 2-position, and 5) the 5, 6, or 7-position (preferably the 6 position) is geminally disubstituted, preferably with two $C_1$-$C_{10}$ alkyl groups;

M is a group 3, 4, 5, or 6 transition metal, preferably group 4 transition metal, for example titanium, zirconium, or hafnium (preferably titanium);

G is a heteroatom group represented by the formula $JR^i_z$ where J is N, P, O or S, $R^i$ is a $C_1$ to $C_{20}$ hydrocarbyl group, and z is 2–y when J is N or P, and 1–y when J is O or S (preferably J is N and z is 1);

T is a bridging group (such as dialkylsilylene or dialkylcarbylene); T is preferably $(CR^8R^9)_x$, $SiR^8R^9$ or $GeR^8R^9$ where x is 1 or 2, $R^8$ and $R^9$ are independently selected from substituted or unsubstituted hydrocarbyl, halocarbyl, silylcarbyl and germylcarbyl and $R^8$ and $R^9$ may optionally be bonded together to form a ring structure, and in a particular embodiment, $R^8$ and $R^9$ are not aryl);

y is 0 or 1, indicating the absence or presence of T;

X is a leaving group (such as a halide, a hydride, an alkyl group, an alkenyl group or an arylalkyl group);

m=1; n=1, 2 or 3; q=1, 2 or 3; and the sum of m+n+q is equal to the oxidation state of the transition metal (preferably 3, 4, 5, or 6, preferably 4); preferably m=1, n=1, q is 2, and y=1.

In any embodiment of formula VII described herein, M is a Group 4 transition metal (preferably Hf, Ti and/or Zr, preferably Ti).

In any embodiment of formula VII described herein, J is N, and $R^i$ is a linear branched or cyclic hydrocarbyl group having from one to twenty carbon atoms (such as methyl, ethyl, propyl, butyl, pentyl, hexyl, heptyl, octyl, nonyl, decyl, undecyl, dodecyl, or an isomer thereof, including t-butyl, cyclododecyl, cyclooctyl or an isomer thereof) and z is 1 or 2, preferably 1, and $JR^i z$ is cyclododecyl amido, t-butyl amido, and or 1-adamantyl amido.

In any embodiment of formula VII described herein, each X may be, independently, a halide, a hydride, an alkyl group, an alkenyl group or an arylalkyl group.

Alternately, in any embodiment of formula VII described herein, each X is, independently, selected from the group consisting of hydrocarbyl radicals having from 1 to 20 carbon atoms, aryls, hydrides, amides, alkoxides, sulfides, phosphides, halides, dienes, amines, phosphines, ethers, and a combination thereof, (two X's may form a part of a fused ring or a ring system), preferably each X is independently selected from halides, aryls and $C_1$ to $C_5$ alkyl groups, preferably each X is a phenyl, methyl, ethyl, propyl, butyl, pentyl, or chloro group.

In any embodiment of formula VII described herein, the Cp' group may be substituted with a combination of substituent groups R. Non-limiting examples of substituent groups R include one or more from the group selected from hydrogen, or linear, branched alkyl radicals, or alkenyl radicals, alkynyl radicals, cycloalkyl radicals or aryl radicals, acyl radicals, alkoxy radicals, aryloxy radicals, alkylthio radicals, dialkylamino radicals, alkoxycarbonyl radicals, aryloxycarbonyl radicals, carbamoyl radicals, alkyl- or dialkyl-carbamoyl radicals, acyloxy radicals, acylamino radicals, aroylamino radicals, straight, branched or cyclic, alkylene radicals, or combination thereof. In a preferred embodiment, substituent groups R have up to 50 non-hydrogen atoms, preferably from 1 to 30 carbon, that can also be substituted with halogens or heteroatoms or the like, provided that when Cp' is tetrahydro-s-indacenyl: 1) the 3 and/or 4 position is not aryl or substituted aryl, 2) the 3-position is not substituted with a group 15 or 16 heteroatom, 3) there are no additional rings fused to the tetrahydroindacenyl ligand, T is not bonded to the 2-position, and 5) the 5, 6, or 7-position (preferably the 6 position) is geminally disubstituted, preferably with two $C_1$-$C_{10}$ alkyl groups. Non-limiting examples of alkyl substituents R include methyl, ethyl, propyl, butyl, pentyl, hexyl, cyclopentyl, cyclohexyl, benzyl or phenyl groups and the like, including all their isomers, for example, tertiary butyl, isopropyl and the like. Other hydrocarbyl radicals include fluoromethyl, fluoroethyl, difluoroethyl, iodopropyl, bromohexyl chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)-silyl, methylbis(difluoromethyl)silyl, bromomethyldimethylgermyl and the like; and disubstituted boron radicals including dimethylboron for example; and disubstituted pnictogen radicals including dimethylamine, dimethylphosphine, diphenylamine, methylphenylphosphine, chalcogen radicals including methoxy, ethoxy, propoxy, phenoxy, methylsulfide and ethylsulfide. Non-hydrogen substituents R include the atoms carbon, silicon, boron, aluminum, nitrogen, phosphorus, oxygen, tin, sulfur, germanium and the like, including olefins such as, but not limited to, olefinically unsaturated substituents including vinyl-terminated ligands, for example but-3-enyl, prop-2-enyl, hex-5-enyl and the like.

In any embodiment of formula VII described herein, the Cp' group, the substituent(s) R are, independently, hydrocarbyl groups, heteroatoms, or heteroatom containing groups, such as methyl, ethyl, propyl, butyl, pentyl, hexyl, heptyl, octyl, nonyl, decyl, undecyl, dodecyl or an isomer thereof, N, O, S, P, or a C1 to C20 hydrocarbyl substituted with an N, O, S and or P heteroatom or heteroatom containing group (typically having up to 12 atoms, including the N, O, S and P heteroatoms), provided that when Cp' is tetrahydro-s-indacenyl, the 3 and/or 4 position are not aryl or substituted aryl, the 3 position is not substituted with a group 15 or 16 heteroatom, and there are no additional rings fused to the tetrahydroindacenyl ligand, T is not bonded to the 2-position, and the 5, 6, or 7-position (preferably the 6 position) is geminally disubstituted, preferably with two $C_1$-$C_{10}$ alkyl groups.

In any embodiment of formula VII described herein, the Cp' group is tetrahydro-as-indacenyl which may be substituted.

In any embodiment of formula VII described herein, y is 1 and T is a bridging group containing at least one Group 13, 14, 15, or 16 element, in particular boron or a Group 14, 15 or 16 element. Examples of suitable bridging groups include P(=S)R*, P(=Se)R*, P(=O)R*, R*$_2$C, R*$_2$Si, R*$_2$Ge, R*$_2$CCR*$_2$, R*$_2$CCR*$_2$CR*$_2$, R*$_2$CCR*$_2$CR*$_2$CR*$_2$, R*C=CR*, R* C=CR* CR*$_2$, R*$_2$CCR*=CR*CR*$_2$, R*C=CR*CR*=CR*, R*C=CR*CR*$_2$CR*$_2$, R*$_2$CSiR*$_2$, R*$_2$SiSiR*$_2$, R*$_2$SiOSiR*$_2$, R*$_2$CSiR*$_2$CR*$_2$, R*$_2$SiCR*$_2$SiR*$_2$, R*C=CR*SiR*$_2$, R*$_2$CGeR*$_2$, R*$_2$GeGeR*$_2$, R*$_2$CGeR*$_2$CR*$_2$, R*$_2$GeCR*$_2$GeR*$_2$, R*$_2$SiGeR*$_2$, R*C=CR*GeR*$_2$, R*B, R*$_2$C—BR*, R*$_2$C—BR*—CR*$_2$, R*$_2$C—O—CR*$_2$, R*$_2$CR*$_2$C—O—CR*$_2$CR*$_2$, R*$_2$C—O—CR*$_2$CR*$_2$, R*$_2$C—O—CR*=CR*, R*$_2$C—S—CR*$_2$, R*$_2$CR*$_2$C—S—CR*$_2$CR*$_2$, R*$_2$C—S—CR*$_2$CR*$_2$, R*$_2$C—S—CR*=CR*, R*$_2$C—Se—CR*$_2$, R*$_2$CR*$_2$C—Se—CR*$_2$CR*$_2$, R*$_2$C—Se—CR*$_2$CR*$_2$, R*$_2$C—Se—CR*=CR*, R*$_2$C—N=CR*, R*$_2$C—NR*—CR*$_2$, R*$_2$C—NR*—CR*$_2$CR*$_2$, R*$_2$C—NR*—CR*=CR*, R*$_2$CR*$_2$C—NR*—CR*$_2$CR*$_2$, R*$_2$C—P=CR*, R*$_2$C—PR*—CR*$_2$, O, S, Se, Te, NR*, PR*, AsR*, SbR*, O—O, S—S, R*N—NR*, R*P—PR*, O—S, O—NR*, O—PR*, S—NR*, S—PR*, and R*N—PR* where R* is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R* may join to form a substituted or unsubstituted, saturated, partially unsaturated or aromatic, cyclic or polycyclic substituent. Preferred examples for the bridging group T include CH$_2$, CH$_2$CH$_2$, SiMe$_2$, SiPh$_2$, SiMePh, Si(CH$_2$)$_3$, Si(CH$_2$)$_4$, O, S, NPh, PPh, NMe, PMe, NEt, NPr, NBu, PEt, PPr, Me$_2$SiOSiMe$_2$, and PBu. In a preferred embodiment of the invention, when Cp' is tetrahydro-s-indacenyl and T is R*$_2$Si, then R* is not aryl.

In some embodiments, R* is not aryl or substituted aryl.

In a preferred embodiment of the invention in any embodiment of any formula described herein, T is represented by the formula ER$^d$$_2$ or (ER$^d$$_2$)$_2$, where E is C, Si, or Ge, and each R$^d$ is, independently, hydrogen, halogen, $C_1$ to $C_{20}$ hydrocarbyl (such as methyl, ethyl, propyl, butyl, pentyl, hexyl, heptyl, octyl, nonyl, decyl, undecyl, or dodecyl) or a $C_1$ to $C_{20}$ substituted hydrocarbyl, and two R$^d$ can form a cyclic structure including aromatic, partially saturated, or saturated cyclic or fused ring system. Preferably, T is a bridging group comprising carbon or silica, such as dialkylsilyl, preferably T is selected from CH$_2$, CH$_2$CH$_2$, C(CH$_3$)$_2$, SiMe$_2$, cyclotrimethylenesilylene (Si(CH$_2$)$_3$), cyclopentamethylenesilylene (Si(CH$_2$)$_5$) and cyclotetramethylenesilylene (Si(CH$_2$)$_4$).

In some preferred embodiments, R$^d$ is not aryl or substituted aryl.

Illustrative, but not limiting, examples of preferred metallocenes for use in this invention's mixed catalyst composition include:
dimethylsilylene(2,6,6-trimethyl-1,5,6,7-tetrahydro-s-indacen-1-yl)(cyclododecylamido)M(R)$_2$ (preferably TiCl$_2$ or TiMe$_2$), dimethylsilylene(2,6,6-trimethyl-1,5,6,7-tetrahydro-s-indacen-1-yl)(t-butylamido)M(R)$_2$ (preferably TiCl$_2$ or TiMe$_2$),
dimethylsilylene(6,6-dimethyl-1,5,6,7-tetrahydro-s-indacen-1-yl)(cyclododecylamido)M(R)$_2$ (preferably TiCl$_2$ or TiMe$_2$),
dimethylsilylene (6,6-dimethyl-1,5,6,7-tetrahydro-s-indacen-1-yl)(t-butylamido)M(R)$_2$ (preferably TiCl$_2$ or TiMe$_2$),
dimethylsilylene(2,7,7-trimethyl-3,6,7,8-tetrahydro-as-indacen-3-yl)(cyclododecylamido)M(R)$_2$ (preferably TiCl$_2$ or TiMe$_2$),
dimethylsilylene(2,7,7-trimethyl-3,6,7,8-tetrahydro-as-indacen-3-yl)(t-butylamido)M(R)$_2$ (preferably TiCl$_2$ or TiMe$_2$),
dimethylsilylene(7,7-dimethyl-3,6,7,8-tetrahydro-as-indacen-3-yl)(cyclododecylamido)M(R)$_2$ (preferably TiCl$_2$ or TiMe$_2$),
dimethylsilylene(7,7-dimethyl-3,6,7,8-tetrahydro-as-indacen-3-yl)(t-butylamido)M(R)$_2$ (preferably TiCl$_2$ or TiMe$_2$),
µ-(CH$_3$)$_2$Si(2,6,6-trimethyl-1,5,6,7-tetrahydro-s-indacen-1-yl)(1-adamantylamido)M(R)$_2$;
µ-(CH$_3$)$_2$Si(6,6-dimethyl-1,5,6,7-tetrahydro-s-indacen-1-yl)(1-adamantylamido)M(R)$_2$;
µ-(CH$_3$)$_2$Si(2-methyl-6,6-diethyl-1,5,6,7-tetrahydro-s-indacen-1-yl)(1-adamantylamido)M(R)$_2$;
µ-(CH$_3$)$_2$Si(6,6-diethyl-1,5,6,7-tetrahydro-s-indacen-1-yl)(1-adamantylamido)M(R)$_2$;
µ-(CH$_3$)$_2$Si(2,7,7-trimethyl-3,6,7,8-tetrahydro-as-indacen-3-yl)(1-adamantylamido)M(R)$_2$;
µ-(CH$_3$)$_2$Si(7,7-dimethyl-3,6,7,8-tetrahydro-as-indacen-3-yl)(1-adamantylamido)M(R)$_2$;
µ-(CH$_3$)$_2$Si(2-methyl-3,6,7,8-tetrahydro-as-indacen-3-yl)(1-adamantylamido)M(R)$_2$;
µ-(CH$_3$)$_2$Si(2-methyl-7,7-diethyl-3,6,7,8-tetrahydro-as-indacen-3-yl)(1-adamantylamido)M(R)$_2$;
µ-(CH$_3$)$_2$Si(7,7-diethyl-3,6,7,8-tetrahydro-as-indacen-3-yl)(1-adamantylamido)M(R)$_2$;
µ-(CH$_3$)$_2$Si(2,6,6-trimethyl-1,5,6,7-tetrahydro-s-indacen-1-yl)(t-butylamido)M(R)$_2$;
µ-(CH$_3$)$_2$Si(6,6-dimethyl-1,5,6,7-tetrahydro-s-indacen-1-yl)(t-butylamido)M(R)$_2$;
µ-(CH$_3$)$_2$Si(2-methyl-6,6-diethyl-1,5,6,7-tetrahydro-s-indacen-1-yl)(t-butylamido)M(R)$_2$;
µ-(CH$_3$)$_2$Si(6,6-diethyl-1,5,6,7-tetrahydro-s-indacen-1-yl)(t-butylamido)M(R)$_2$;
µ-(CH$_3$)$_2$Si(2,7,7-trimethyl-3,6,7,8-tetrahydro-as-indacen-3-yl)(t-butylamido)M(R)$_2$;
µ-(CH$_3$)$_2$Si(7,7-dimethyl-3,6,7,8-tetrahydro-as-indacen-3-yl)(t-butylamido)M(R)$_2$;
µ-(CH$_3$)$_2$Si(2-methyl-3,6,7,8-tetrahydro-as-indacen-3-yl)(t-butylamido)M(R)$_2$;
µ-(CH$_3$)$_2$Si(2-methyl-7,7-diethyl-3,6,7,8-tetrahydro-as-indacen-3-yl)(t-butylamido)M(R)$_2$;
µ-(CH$_3$)$_2$Si(7,7-diethyl-3,6,7,8-tetrahydro-as-indacen-3-yl)(t-butylamido)M(R)$_2$;
µ-(CH$_3$)$_2$Si(2,6,6-trimethyl-1,5,6,7-tetrahydro-s-indacen-1-yl)(cyclododecylamido)M(R)$_2$;
µ-(CH$_3$)$_2$Si(6,6-dimethyl-1,5,6,7-tetrahydro-s-indacen-1-yl)(cyclododecylamido)M(R)$_2$;
µ-(CH$_3$)$_2$Si(2-methyl-6,6-diethyl-1,5,6,7-tetrahydro-s-indacen-1-yl)(cyclododecylamido)M(R)$_2$;
µ-(CH$_3$)$_2$Si(6,6-diethyl-1,5,6,7-tetrahydro-s-indacen-1-yl)(cyclododecylamido)M(R)$_2$;
µ-(CH$_3$)$_2$Si(2,7,7-trimethyl-3,6,7,8-tetrahydro-as-indacen-3-yl)(cyclododecylamido)M(R)$_2$;
µ-(CH$_3$)$_2$Si(7,7-dimethyl-3,6,7,8-tetrahydro-as-indacen-3-yl)(cyclododecylamido)M(R)$_2$;
µ-(CH$_3$)$_2$Si(2-methyl-3,6,7,8-tetrahydro-as-indacen-3-yl)(cyclododecylamido)M(R)$_2$;
µ-(CH$_3$)$_2$Si(2-methyl-7,7-diethyl-3,6,7,8-tetrahydro-as-indacen-3-yl)(cyclododecylamido)M(R)$_2$;
µ-(CH$_3$)$_2$Si(7,7-diethyl-3,6,7,8-tetrahydro-as-indacen-3-yl)(cyclododecylamido)M(R)$_2$;
µ-(CH$_2$)$_3$Si(2,6,6-trimethyl-1,5,6,7-tetrahydro-s-indacen-1-yl)(t-butylamido)M(R)$_2$;
µ-(CH$_2$)$_4$Si(2,6,6-trimethyl-1,5,6,7-tetrahydro-s-indacen-1-yl)(t-butylamido)M(R)$_2$;
µ-(CH$_2$)$_5$Si(2,6,6-trimethyl-1,5,6,7-tetrahydro-s-indacen-1-yl)(t-butylamido)M(R)$_2$;
µ-(CH$_3$)$_2$C(2,6,6-trimethyl-1,5,6,7-tetrahydro-s-indacen-1-yl)(t-butylamido)M(R)$_2$;
µ-(CH$_2$)$_3$Si(2,6,6-trimethyl-1,5,6,7-tetrahydro-s-indacen-1-yl)(t-butylamido)M(R)$_2$;
µ-(CH$_2$)$_4$Si(2,6,6-trimethyl-1,5,6,7-tetrahydro-s-indacen-1-yl)(t-butylamido)M(R)$_2$;
µ-(CH$_2$)$_5$Si(2,6,6-trimethyl-1,5,6,7-tetrahydro-s-indacen-1-yl)(t-butylamido)M(R)$_2$;
µ-(CH$_3$)$_2$C(2,6,6-trimethyl-1,5,6,7-tetrahydro-s-indacen-1-yl)(t-butylamido)M(R)$_2$; and
µ-(CH$_3$)$_2$Si(2,6,6-trimethyl-1,5,6,7-tetrahydro-s-indacen-1-yl)(neopentylamido)M(R)$_2$;
where M is selected from a group consisting of Ti, Zr, and Hf and R is selected from halogen or C1 to C5 alkyl, preferably R' is a methyl group or a halogen group, (preferably TiCl$_2$ or TiMe$_2$).

In alternate embodiments, two or more different transition metal compounds may be used herein. For purposes of this invention one transition metal compound is considered different from another if they differ by at least one atom. For example "Me$_2$Si(2,7,7-Me$_3$-3,6,7,8-tetrahydro-as-indacen-3-yl)(cyclohexylamido)TiCl$_2$" is different from Me$_2$Si(2,7,7-Me$_3$-3,6,7,8-tetrahydro-as-indacen-3-yl)(n-butylamido)TiCl$_2$" which is different from Me$_2$Si(2,7,7-Me$_3$-3,6,7,8-tetrahydro-as-indacen-3-yl)(n-butylamido)HfCl$_2$.

In a preferred embodiment, one mono-tetrahydroindacenyl compound as described herein is used in the catalyst system.

Activators

The terms "cocatalyst" and "activator" are used herein interchangeably and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing noncoordinating or weakly coordinating anion.

Alumoxane Activators

Alumoxane activators are utilized as activators in the catalyst systems described herein. Alumoxanes are generally oligomeric compounds containing —Al(R$^1$)—O— sub-units, where R$^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A, covered under U.S. Pat. No. 5,041,584).

When the activator is an alumoxane (modified or unmodified), some embodiments select the maximum amount of activator typically at up to a 5000-fold molar excess Al/M over the catalyst compound (per metal catalytic site). The minimum activator-to-catalyst-compound is a 1:1 molar ratio. Alternate preferred ranges include from 1:1 to 500:1, alternately from 1:1 to 200:1, alternately from 1:1 to 100:1, or alternately from 1:1 to 50:1.

Non Coordinating Anion Activators

Non-coordinating anion activators may also be used herein. The term "non-coordinating anion" (NCA) means an anion which either does not coordinate to a cation or which is only weakly coordinated to a cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) ammonium tetrakis (pentafluorophenyl) borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), in combination with the alumoxane or modified alumoxane activators. It is also within the scope of this invention to use neutral or ionic activators in combination with the alumoxane or modified alumoxane activators.

The catalyst systems of this invention can include at least one non-coordinating anion (NCA) activator. Specifically the catalyst systems may include an NCAs which either do not coordinate to a cation or which only weakly coordinate to a cation thereby remaining sufficiently labile to be displaced during polymerization.

The terms "cocatalyst" and "activator" are used herein interchangeably and are defined to be any compound which can activate any one of the catalyst compounds described above by converting the neutral catalyst compound to a catalytically active catalyst compound cation.

In a preferred embodiment boron containing NCA activators represented by the formula below can be used:

where: Z is (L-H) or a reducible Lewis acid; L is a neutral Lewis base; H is hydrogen; (L-H) is a Bronsted acid; $A^{d-}$ is a boron containing non-coordinating anion having the charge d−; d is 1, 2, or 3.

The cation component, $Z_d^+$ may include Bronsted acids such as protons or protonated Lewis bases or reducible Lewis acids capable of protonating or abstracting a moiety, such as an alkyl or aryl, from the bulky ligand metallocene containing transition metal catalyst precursor, resulting in a cationic transition metal species.

The activating cation $Z_d^+$ may also be a moiety such as silver, tropylium, carboniums, ferroceniums and mixtures, preferably carboniums and ferroceniums. Most preferably $Z_d^+$ is triphenyl carbonium. Preferred reducible Lewis acids can be any triaryl carbonium (where the aryl can be substituted or unsubstituted, such as those represented by the formula: $(Ar_3C^+)$, where Ar is aryl or aryl substituted with a heteroatom, a $C_1$ to $C_{40}$ hydrocarbyl, or a substituted C1 to C40 hydrocarbyl), preferably the reducible Lewis acids in formula (14) above as "Z" include those represented by the formula: $(Ph_3C)$, where Ph is a substituted or unsubstituted phenyl, preferably substituted with $C_1$ to $C_{40}$ hydrocarbyls or substituted a $C_1$ to $C_{40}$ hydrocarbyls, preferably $C_1$ to $C_{20}$ alkyls or aromatics or substituted $C_1$ to $C_{20}$ alkyls or aromatics, preferably Z is a triphenylcarbonium.

When $Z_d^+$ is the activating cation $(L-H)_d^+$, it is preferably a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiums from ethers such as dimethyl ether diethyl ether, tetrahydrofuran and dioxane, sulfoniums from thioethers, such as diethyl thioethers, tetrahydrothiophene, and mixtures thereof.

The anion component $A^{d-}$ includes those having the formula $[M^{k+}Q_n]^{d-}$ wherein k is 1, 2, or 3; n is 1, 2, 3, 4, 5, or 6 (preferably 1, 2, 3, or 4); n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst are the compounds described as (and particularly those specifically listed as) activators in U.S. Pat. No. 8,658,556, which is incorporated by reference herein.

Most preferably, the ionic stoichiometric activator $Z_d^+$ $(A^{d-})$ is one or more of N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

Bulky activators are also useful herein as NCAs. "Bulky activator" as used herein refers to anionic activators represented by the formula:

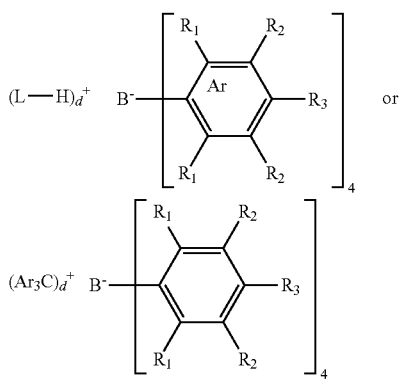

where: each $R_1$ is, independently, a halide, preferably a fluoride; Ar is substituted or unsubstituted aryl group (preferably a substituted or unsubstituted phenyl), preferably substituted with $C_1$ to $C_{40}$ hydrocarbyls, preferably $C_1$ to $C_{20}$ alkyls or aromatics; each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group); each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring); and L is an neutral Lewis base; (L-H)$^+$ is a Bronsted acid; d is 1, 2, or 3; wherein the anion has a molecular weight of greater than 1020 g/mol; wherein at least three of the substituents on the B atom each have a molecular volume of greater than 250 cubic Å, alternately greater than 300 cubic Å, or alternately greater than 500 cubic Å.

Preferably $(Ar_3C)_d^+$ is $(Ph_3C)_d^+$, where Ph is a substituted or unsubstituted phenyl, preferably substituted with $C_1$ to $C_{40}$ hydrocarbyls or substituted $C_1$ to $C_{40}$ hydrocarbyls, preferably $C_1$ to $C_{20}$ alkyls or aromatics or substituted $C_1$ to $C_{20}$ alkyls or aromatics.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple "Back of the Envelope" Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: $MV=8.3V_s$, where $V_s$ is the scaled volume. $V_s$ is the sum of the relative volumes of the constituent atoms, and is calculated from the molecular formula of the substituent using the following table of relative volumes. For fused rings, the $V_s$ is decreased by 7.5% per fused ring.

| Element | Relative Volume |
|---|---|
| H | 1 |
| 1$^{st}$ short period, Li to F | 2 |
| 2$^{nd}$ short period, Na to Cl | 4 |
| 1$^{st}$ long period, K to Br | 5 |
| 2$^{nd}$ long period, Rb to I | 7.5 |
| 3$^{rd}$ long period, Cs to Bi | 9 |

For a list of particularly useful Bulky activators please see U.S. Pat. No. 8,658,556, which is incorporated by reference herein.

In another embodiment, one or more of the NCA activators is chosen from the activators described in U.S. Pat. No. 6,211,105.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(perfluorophenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph$_3$C$^+$][B(C$_6$F$_5$)$_4^-$], [Me$_3$NH$^+$][B(C$_6$F$_5$)$_4^-$]; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl)phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium) tetrakis(pentafluorophenyl)borate, trialkylammonium tetrakis-(2,3,4,6-tetrafluorophenyl) borate, N,N-dialkylanilinium tetrakis-(2,3,4,6-tetrafluorophenyl)borate, trialkylammonium tetrakis (perfluoronaphthyl)borate, N,N-dialkylanilinium tetrakis (perfluoronaphthyl)borate, trialkylammonium tetrakis (perfluorobiphenyl)borate, N,N-dialkylanilinium tetrakis (perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl)phenyl)borate, di-(i-propyl)ammonium tetrakis(pentafluorophenyl)borate, (where alkyl is methyl, ethyl, propyl, n-butyl, sec-butyl, or t-butyl).

The typical NCA activator-to-catalyst ratio, e.g., all NCA activators-to-catalyst ratio is about a 1:1 molar ratio. Alternate preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

Activators useful herein also include those described in U.S. Pat. No. 7,247,687 at column 169, line 50 to column 174, line 43, particularly column 172, line 24 to column 173, line 53.

It is also within the scope of this invention that the catalyst compounds can be combined with combinations of alumoxanes and NCA's (see for example, U.S. Pat. No. 5,153,157, U.S. Pat. No. 5,453,410, EP 0 573 120 B1, WO 94/07928, and WO 95/14044 which discuss the use of an alumoxane in combination with an ionizing activator).

Optional Scavengers or Co-Activators

In addition to the activator compounds, scavengers, chain transfer agents or co-activators may be used. Aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum, and diethyl zinc.

Useful chain transfer agents that may also be used herein are typically a compound represented by the formula $AlR_3$, $ZnR_2$ (where each R is, independently, a $C_1$-$C_8$ aliphatic radical, preferably methyl, ethyl, propyl, butyl, penyl, hexyl octyl or an isomer thereof) or a combination thereof, such as diethyl zinc, trimethylaluminum, triisobutylaluminum, tri-octylaluminum, or a combination thereof.

Supports

In some embodiments, the complexes described herein may be supported (with or without an activator) by any method effective to support other coordination catalyst systems, effective meaning that the catalyst so prepared can be used for oligomerizing or polymerizing olefin in a heterogeneous process. The catalyst precursor, activator, co-activator if needed, suitable solvent, and support may be added in any order or simultaneously. Typically, the complex and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The complex may also be supported absent the activator; in that case, the activator (and co-activator if needed) is added to a polymerization process's liquid phase. Additionally, two or more different complexes may be placed on the same support. Likewise, two or more activators or an activator and co-activator may be placed on the same support.

Suitable solid particle supports are typically comprised of polymeric or refractory oxide materials, each being preferably porous. Preferably any support material that has an average particle size greater than 10 μm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component, however, an additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Useful supports typically have a surface area of from 10-700 m$^2$/g, a pore volume of 0.1-4.0 cc/g and an average particle size of 10-500 μm. Some embodiments select a surface area of 50-500 m$^2$/g, a pore volume of 0.5-3.5 cc/g, or an average particle size of 20-200 μm. Other embodiments select a surface area of 100-400 m$^2$/g, a pore volume of 0.8-3.0 cc/g, and an average particle size of 30-100 μm. Useful supports typically have a pore size of 10-1000 Angstroms, alternatively 50-500 Angstroms, or 75-350 Angstroms.

The catalyst complexes described herein are generally deposited on the support at a loading level of 10-100 micromoles of complex per gram of solid support; alternately 20-80 micromoles of complex per gram of solid support; or 40-60 micromoles of complex per gram of support. But greater or lesser values may be used provided that the total amount of solid complex does not exceed the support's pore volume.

In an alternate embodiment, catalyst complexes and catalyst systems described herein may be present on a fluorided support, e.g. a support, desirably particulate and porous, which has been treated with at least one inorganic fluorine containing compound. For example, the fluorided support composition can be a silicon dioxide support wherein a portion of the silica hydroxyl groups has been replaced with fluorine or fluorine containing compounds. For example, a useful support herein, is a silica support treated with ammonium hexafluorosilicate and/or ammonium tetrafluoroborate fluorine compounds. Typically the fluorine concentration present on the support is in the range of from 0.1 to 25 wt %, alternately 0.19 to 19 wt %, alternately from 0.6 to 3.5 wt %, based upon the weight of the support.

In an embodiment if of the invention the catalyst system comprises fluorided silica, alkylalumoxane activator, and the bridged monocyclopentadienyl group 4 transition metal compound, where the fluorided support has not been calcined at a temperature of 400° C. or more.

The catalyst compound may be present on a support at 1 to 100 μmol/g supported catalyst, preferably 20-60 μmol/g supported catalyst.

This invention also relates to metallocene catalyst compositions comprising the reaction product of at least three components: (1) one or more bridged metallocenes having one tetrahydroindacenyl group; (2) one or more alkylalumoxane activators; and (3) one or more fluorided support compositions, where the fluorided support composition has not been calcined at 400° C. or more, preferably the fluorided support composition has been calcined at a temperature of 100° C. to 395° C., alternately 125° C. to 350° C., alternately 150° C. to 300° C.).

Typically, the fluorided supports described herein are prepared by combining a solution of polar solvent (such as water) and fluorinating agent (such as SiF$_4$ or (NH$_4$)$_2$SiF$_6$) with a slurry of support (such as a toluene slurry of silica), then drying until it is free flowing, and optionally, calcining (typically at temperatures over 100° C. for at least 1 hour). The supports are then combined with activator(s) and catalyst compound (separately or together).

For more information on fluorided supports and methods to prepare them, please see U.S. Ser. No. 62/149,799, filed Apr. 20, 2015 (and all cases claiming priority to or the benefit of U.S. Ser. No. 62/149,799); U.S. Ser. No. 62/103,372, filed Jan. 14, 2015 (and all cases claiming priority to or the benefit of U.S. Ser. No. 62/103,372); and PCT/US2015/067582, filed Dec. 28, 2015 which are incorporated by reference herein.

Polymerization Processes

In embodiments herein, the invention relates to polymerization processes where monomer (such as ethylene), and optionally comonomer (such as hexene), are contacted with a catalyst system comprising the result of the combination of an activator, optional support (such as a fluorided support), and a tetrahydroindacene compound, as described above. The catalyst compound, optional support and activator may be combined in any order, and are combined typically prior to contacting with the monomer.

Monomers useful herein include substituted or unsubstituted C2 to C40 alpha olefins, preferably C2 to C20 alpha olefins, preferably C2 to C12 alpha olefins, preferably ethylene, propylene, butene, pentene, hexene, heptene, octene, nonene, decene, undecene, dodecene and isomers thereof. In a preferred embodiment of the invention, the monomers comprises ethylene and optional comonomers comprising one or more $C_3$ to $C_{40}$ olefins, preferably $C_4$ to $C_{20}$ olefins, or preferably $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_3$ to $C_{40}$ comonomers include propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, 5-ethylidene-2-norbornene, and their respective homologs and derivatives.

In a preferred embodiment one or more dienes are present in the polymer produced herein at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Preferred diolefin monomers useful in this invention include any hydrocarbon structure, preferably C4 to C30, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, 5-ethylidene-2-norbornene, 5-vinyl-2-norbornene, divinylbenzene, dicyclopentadiene or higher ring containing diolefins with or without substituents at various ring positions.

In a particularly preferred embodiment the process of the invention relates to the polymerization of ethylene and at least one comonomer having from 3 to 8 carbon atoms, preferably 4 to 8 carbon atoms. Particularly, the comonomers are propylene, butene-1, 4-methyl-pentene-1,3-methyl-pentene-1, hexene-1 and octene-1, the most preferred being hexene-1, butene-1 and octene-1.

Polymerization processes of this invention can be carried out in any manner known in the art. Any suspension, homogeneous, bulk, solution, slurry, or gas phase polymerization process known in the art can be used. Such processes can be run in a batch, semi-batch, or continuous mode. Gas phase polymerization processes and slurry processes are preferred. (A homogeneous polymerization process is defined to be a process where at least 90 wt % of the product is soluble in the reaction media.) A bulk homogeneous process is particularly preferred. (A bulk process is defined to be a process where monomer concentration in all feeds to the reactor is 70 volume % or more.) Alternately, no solvent or diluent is present or added in the reaction medium, (except for the small amounts used as the carrier for the catalyst system or other additives, or amounts typically found with the monomer; e.g., propane in propylene). In another embodiment, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt % based upon the weight of the solvents.

In a preferred embodiment, the feed concentration of the monomers and comonomers for the polymerization is 60 vol % solvent or less, preferably 40 vol % or less, or preferably 20 vol % or less, based on the total volume of the feedstream. Preferably the polymerization is run in a bulk process.

Preferred polymerizations can be run at any temperature and/or pressure suitable to obtain the desired polymers. Typical temperatures and/or pressures include a temperature in the range of from about 0° C. to about 300° C., preferably about 20° C. to about 200° C., preferably about 35° C. to about 150° C., preferably from about 40° C. to about 120° C., preferably from about 45° C. to about 80° C.; and at a pressure in the range of from about 0.35 MPa to about 16 MPa, preferably from about 0.45 MPa to about 13 MPa, or preferably from about 0.5 MPa to about 12 MPa.

In a typical polymerization, the run time of the reaction is up to 300 minutes, preferably in the range of from about 5 to 250 minutes, or preferably from about 10 to 120 minutes.

In some embodiments hydrogen is present in the polymerization reactor at a partial pressure of 0.001 to 50 psig (0.007 to 345 kPa), preferably from 0.01 to 25 psig (0.07 to 172 kPa), more preferably 0.1 to 10 psig (0.7 to 70 kPa).

In an alternate embodiment, the activity of the catalyst is at least 800 gpolymer/gsupported catalyst/hour, preferably 1000 or more gpolymer/gsupported catalyst/hour, preferably 100 or more gpolymer/gsupported catalyst/hour, preferably 1600 or more gpolymer/gsupported catalyst/hour.

In a preferred embodiment, little or no scavenger is used in the process to produce the ethylene polymer. Preferably, scavenger (such as tri alkyl aluminum) is present at zero mol %, alternately the scavenger is present at a molar ratio of scavenger metal to transition metal of less than 100:1, preferably less than 50:1, preferably less than 15:1, preferably less than 10:1.

In a preferred embodiment, the polymerization: 1) is conducted at temperatures of 0 to 300° C. (preferably 25 to 150° C., preferably 40 to 120° C., preferably 45 to 80° C.); 2) is conducted at a pressure of atmospheric pressure to 16 MPa (preferably 0.35 to 14 MPa, preferably from 0.45 to 12 MPa, preferably from 0.5 to 6 MPa); 3) is conducted in an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof; preferably where aromatics are preferably present in the solvent at less than 1 wt %, preferably less than 0.5 wt %, preferably at 0 wt % based upon the weight of the solvents); 4) the polymerization preferably occurs in one reaction zone; and 5) optionally hydrogen is present in the polymerization reactor at a partial pressure of 0.001 to 50 psig (0.007 to 345 kPa) (preferably from 0.01 to 25 psig (0.07 to 172 kPa), more preferably 0.1 to 10 psig (0.7 to 70 kPa)).

A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In a preferred embodiment, the polymerization occurs in one reaction zone.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

Slurry Phase Polymerization

A slurry polymerization process generally operates between 1 to about 50 atmosphere pressure range (15 psi to 735 psi, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In an embodiment, a preferred polymerization technique useful in the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. (In one embodiment 500 ppm or less of hydrogen is added, or 400 ppm or less or 300 ppm or less. In other embodiments at least 50 ppm of hydrogen is added, or 100 ppm or more, or 150 ppm or more.)

The reactor may be maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

Useful chain transfer agents are typically alkylalumoxanes, a compound represented by the formula $AlR_3$, $ZnR_2$ (where each R is, independently, a $C_1$-$C_8$ aliphatic radical, preferably methyl, ethyl, propyl, butyl, penyl, hexyl octyl or an isomer thereof) or a combination thereof, such as diethyl zinc, methylalumoxane, trimethylaluminum, triisobutylaluminum, trioctylaluminum, or a combination thereof.

Polyolefin Products

This invention also relates to compositions of matter produced by the methods described herein.

In a preferred embodiment, the process described herein produces ethylene homopolymers or ethylene copolymers, such as ethylene-alphaolefin (preferably C3 to C20) copolymers (such as ethylene-butene copolymers, ethylene-hexene and/or ethylene-octene copolymers) having: a Mw/Mn of greater than 1 to 4 (preferably greater than 1 to 3).

Likewise, the process of this invention produces ethylene copolymers. In a preferred embodiment, the copolymers produced herein have from 0 to 25 mole % (alternately from 0.5 to 20 mole %, alternately from 1 to 15 mole %, preferably from 3 to 10 mole %) of one or more $C_3$ to $C_{20}$ olefin comonomer (preferably $C_3$ to $C_{12}$ alpha-olefin, preferably propylene, butene, hexene, octene, decene, dodecene, preferably propylene, butene, hexene, octene).

In a preferred embodiment, the monomer is ethylene and the comonomer is hexene, preferably from 1 to 15 mole % hexene, alternately 1 to 10 mole %.

Typically, the polymers produced herein have an Mw of 5,000 to 1,000,000 g/mol (preferably 25,000 to 750,000 g/mol, preferably 50,000 to 500,000 g/mol), and/or an Mw/Mn of greater than 1 to 40 (alternately 1.2 to 20, alternately 1.3 to 10, alternately 1.4 to 5, 1.5 to 4, alternately 1.5 to 3).

In a preferred embodiment the polymer produced herein has a unimodal or multimodal molecular weight distribution as determined by Gel Permeation Chromotography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versus).

Unless otherwise indicated Mw, Mn and Mw/Mn are determined by using a High Temperature Gel Permeation Chromatography (Agilent PL-220), equipped with three in-line detectors, a differential refractive index detector (DRI), a light scattering (LS) detector, and a viscometer. Experimental details, including detector calibration, are described in: T. Sun, P. Brant, R. R. Chance, and W. W. Graessley, Macromolecules, Volume 34, Number 19, pp. 6812-6820, (2001) and references therein. Three Agilent PLgel 10 μm Mixed-B LS columns are used. The nominal flow rate is 0.5 mL/min, and the nominal injection volume is 300 μL. The various transfer lines, columns, viscometer and differential refractometer (the DRI detector) are contained in an oven maintained at 145° C. Solvent for the experiment is prepared by dissolving 6 grams of butylated hydroxytoluene as an antioxidant in 4 liters of Aldrich reagent grade 1,2,4-trichlorobenzene (TCB). The TCB mixture is then filtered through a 0.1 μm Teflon filter. The TCB is then degassed with an online degasser before entering the GPC-3D. Polymer solutions are prepared by placing dry polymer in a glass container, adding the desired amount of TCB, then heating the mixture at 160° C. with continuous shaking for about 2 hours. All quantities are measured gravimetrically. The TCB densities used to express the polymer concentration in mass/volume units are 1.463 g/ml at room temperature and 1.284 g/ml at 145° C. The injection concentration is from 0.5 to 2.0 mg/ml, with lower concentrations being used for higher molecular weight samples. Prior to running each sample the DRI detector and the viscometer are purged. Flow rate in the apparatus is then increased to 0.5 ml/minute, and the DRI is allowed to stabilize for 8 hours before injecting the first sample. The LS laser is turned on at least 1 to 1.5 hours before running the samples. The concentration, c, at each point in the chromatogram is calculated from the baseline-subtracted DRI signal, $I_{DRI}$, using the following equation:

$$c = K_{DRI} I_{DRI} / (dn/dc)$$

where $K_{DRI}$ is a constant determined by calibrating the DRI, and (dn/dc) is the refractive index increment for the system. The refractive index, n=1.500 for TCB at 145° C. and λ=690 nm. Units on parameters throughout this description of the GPC-3D method are such that concentration is expressed in g/cm$^3$, molecular weight is expressed in g/mole, and intrinsic viscosity is expressed in dL/g.

The LS detector is a Wyatt Technology High Temperature DAWN HELEOS. The molecular weight, M, at each point in the chromatogram is determined by analyzing the LS output using the Zimm model for static light scattering (M. B. Huglin, LIGHT SCATTERING FROM POLYMER SOLUTIONS, Academic Press, 1971).

$$\frac{K_o c}{\Delta R(\theta)} = \frac{1}{MP(\theta)} + 2 A_2 c$$

Here, $\Delta R(\theta)$ is the measured excess Rayleigh scattering intensity at scattering angle θ, c is the polymer concentration determined from the DRI analysis, $A_2$ is the second virial coefficient. $P(\theta)$ is the form factor for a monodisperse random coil, and $K_o$ is the optical constant for the system:

$$K_o = \frac{4\pi^2 n^2 \left(\frac{dn}{dc}\right)^2}{\lambda^4 N_A}$$

where $N_A$ is Avogadro's number, and (dn/dc) is the refractive index increment for the system, which take the same value as the one obtained from DRI method. The refractive index, n=1.500 for TCB at 145° C. and λ=690 nm.

A high temperature Viscotek Corporation viscometer, which has four capillaries arranged in a Wheatstone bridge configuration with two pressure transducers, is used to determine specific viscosity. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, [η], at each point in the chromatogram is calculated from the following equation:

$$\eta_s = c[\eta] + 0.3(c[\eta])^2$$

where c is concentration and was determined from the DRI output. All molecular weights are weight average unless otherwise noted. All molecular weights are reported in g/mol unless otherwise noted.

In a preferred embodiment the polymer produced herein has a composition distribution breadth index (CDBI) of 50% or more, preferably 60% or more, preferably 70% or more. CDBI is a measure of the composition distribution of monomer within the polymer chains and is measured by the procedure described in PCT publication WO 93/03093, published Feb. 18, 1993, specifically columns 7 and 8 as well as in Wild et al, J. Poly. Sci., Poly. Phys. Ed., Vol. 20, p. 441 (1982) and U.S. Pat. No. 5,008,204, including that fractions having a weight average molecular weight (Mw) below 15,000 are ignored when determining CDBI.

In another embodiment, the polymer produced herein has two peaks in the TREF measurement (see below). Two peaks in the TREF measurement as used in this specification and the appended claims means the presence of two distinct normalized ELS (evaporation mass light scattering) response peaks in a graph of normalized ELS response (vertical or y axis) versus elution temperature (horizontal or x axis with temperature increasing from left to right) using the TREF method below. A "peak" in this context means where the general slope of the graph changes from positive to negative with increasing temperature. Between the two peaks is a local minimum in which the general slope of the graph changes from negative to positive with increasing temperature. "General trend" of the graph is intended to exclude the multiple local minimums and maximums that can occur in intervals of 2° C. or less. Preferably, the two distinct peaks are at least 3° C. apart, more preferably at least 4° C. apart, even more preferably at least 5° C. apart. Additionally, both of the distinct peaks occur at a temperature on the graph above 20° C. and below 120° C. where the elution temperature is run to 0° C. or lower. This limitation avoids confusion with the apparent peak on the graph at low temperature caused by material that remains soluble at the lowest elution temperature. Two peaks on such a graph indicates a bi-modal composition distribution (CD). Bimodal CD may also be determined by other methods known to those skilled in the art. One such alternate method for TREF measurement then can be used if the above method does not show two peaks is disclosed in B. Monrabal, "Crystallization Analysis Fractionation: A New Technique for the Analysis of Branching Distribution in Polyolefins," Journal of Applied Polymer Science, Vol. 52, 491-499 (1994).

TREF Method

Temperature Rising Elution Fractionation (TREF) analysis is done using a CRYSTAF-TREF 200+ instrument from Polymer Char, S.A., Valencia, Spain. The principles of TREF analysis and a general description of the particular apparatus to be used are given in the article Monrabal, B.; del Hierro, P. *Anal. Bioanal. Chem.* 2011, 399, 1557. FIG. 3 of the article is an appropriate schematic of the particular apparatus used; however, the connections to the 6-port valve shown in FIG. 3 differ from the apparatus to be used in that the tubing connected to the 11-o'clock port is connected to the 9-o'clock port and the tubing connected to the 9-o'clock port is connected to the 11-o'clock port. Pertinent details of the analysis method and features of the apparatus to be used are as follows.

1,2-Dichlorobenzene (ODCB) solvent stabilized with approximately 380 ppm of 2,6-bis(1,1-dimethylethyl)-4-methylphenol (butylated hydroxytoluene) is used for preparing the sample solution and for elution. The sample to be analyzed (approximately 25 mg but as low as approximately 10 mg) is dissolved in ODCB (25 ml metered at ambient temperature) by stirring at 150° C. for 60 min. A small volume (0.5 ml) of the solution is introduced into a column (15-cm long by ⅜" o.d.) packed with an inert support (of stainless steel balls) at 150° C., and the column temperature is stabilized at 140° C. for 45 min. The sample volume is then allowed to crystallize in the column by reducing the temperature to 30° C. at a cooling rate of 1° C./min. The column is kept at 30° C. for 15 min before injecting the ODCB flow (1 ml/min) into the column for 10 min to elute and measure the polymer that did not crystallize (soluble fraction). The infrared detector used (Polymer Char IR4) generates an absorbance signal that is proportional to the concentration of polymer in the eluting flow. A complete TREF curve is then generated by increasing the temperature of the column from 30 to 140° C. at a rate of 2° C./min while maintaining the ODCB flow at 1 ml/min to elute and measure the dissolving polymer.

Blends

In another embodiment, the polymer produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In a preferred embodiment, the polymer (preferably the polyethylene produced herein) is present in the above blends, at from 10 to 99 wt %, based upon the weight of the polymers in the blend, preferably 20 to 95 wt %, even more preferably at least 30 to 90 wt %, even more preferably at least 40 to 90 wt %, even more preferably at least 50 to 90 wt %, even more preferably at least 60 to 90 wt %, even more preferably at least 70 to 90 wt %.

Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Films

Specifically, any of the foregoing polymers, such as the foregoing ethylene copolymers or blends thereof, may be used in a variety of end-use applications. Such applications include, for example, mono- or multi-layer blown, extruded, and/or shrink films. These films may be formed by any number of well known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxially orientation can be accomplished using typical cold drawing or hot drawing methods. Biaxial orientation can be accomplished using tenter frame equipment or a double bubble processes and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, preferably between 5 and 7, and in the Transverse Direction (TD) at a ratio of up to 15, preferably 7 to 9. However, in another embodiment the film is oriented to the same extent in both the MD and TD directions.

The films may vary in thickness depending on the intended application; however, films of a thickness from 1 to 50 μm are usually suitable. Films intended for packaging are usually from 10 to 50 μm thick. The thickness of the sealing layer is typically 0.2 to 50 μm. There may be a sealing layer on both the inner and outer surfaces of the film or the sealing layer may be present on only the inner or the outer surface.

In another embodiment, one or more layers may be modified by corona treatment, electron beam irradiation, gamma irradiation, flame treatment, or microwave. In a preferred embodiment, one or both of the surface layers is modified by corona treatment.

In another embodiment, this invention relates to:

1. A compound represented by the formula: $T_y Cp'_m MG_n X_q$ wherein: Cp' is a tetrahydroindacenyl group which may be substituted or unsubstituted, provided that when Cp' is tetrahydro-s-indacenyl: 1) the 3 and/or 4 positions are not aryl or substituted aryl, 2) the 3 position is not directly bonded to a group 15 or 16 heteroatom, 3) there are no additional rings fused to the tetrahydroindacenyl ligand, 4) T is not bonded to the 2-position, and 5) the 5, 6, or 7-position is geminally disubstituted; M is a group 3, 4, 5, or 6 transition metal; G is a heteroatom group represented by the formula $JR^i_z$ where J is N, P, O or S, $R^1$ is a $C_1$ to $C_{20}$ hydrocarbyl group, and z is 2-y when J is N or P and 1-y when J is O or S; T is a bridging group; y is 0 or 1; X is a leaving group; m=1; n=1, 2 or 3; q=1, 2 or 3, and the sum of m+n+q is equal to the oxidation state of the transition metal (e.g., 3, 4, 5 or 6).

2. A compound represented by the formula (I):

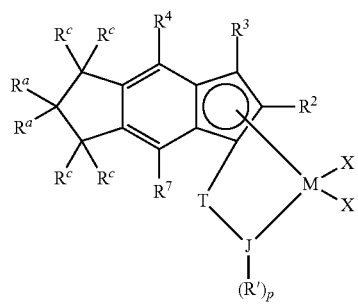

(I)

where: M is a group 4 metal; J is N, O, S or P; p is 1 when J is N or P, and is 0 when J is O or S; each $R^a$ is independently a $C_1$-$C_{10}$ alkyl; each $R^c$ is independently hydrogen or a $C_1$-$C_{10}$ alkyl; each $R^2$, $R^3$, $R^4$, and $R^7$ is independently hydrogen, or a $C_1$-$C_{50}$ substituted or unsubstituted hydrocarbyl, halocarbyl or silylcarbyl, provided that: 1) $R^3$ and/or $R^4$ are not aryl or substituted aryl, 2) $R^3$ is not substituted with a group 15 or 16 heteroatom; and 3) that adjacent $R^4$, $R^c$, $R^a$, and or $R^7$ do not join together to form a fused ring system; each R' and $R^i$ is independently a $C_1$-$C_{100}$ substituted or unsubstituted hydrocarbyl, halocarbyl, or silylcarbyl; T is $(CR^8R^9)_x$, $SiR^8R^9$ or $GeR^8R^9$ where x is 1 or 2, $R^8$ and $R^9$ are independently selected from hydrogen, or substituted or unsubstituted hydrocarbyl, halocarbyl, silylcarbyl and germylcarbyl and $R^8$ and $R^9$ may optionally be bonded together to form a ring structure; each X is, independently, a leaving group, or two Xs are joined and bound to the metal atom to form a metallocycle ring, or two Xs are joined to form a chelating ligand, a diene ligand, or an alkylidene.

3. A compound represented by the formula (II):

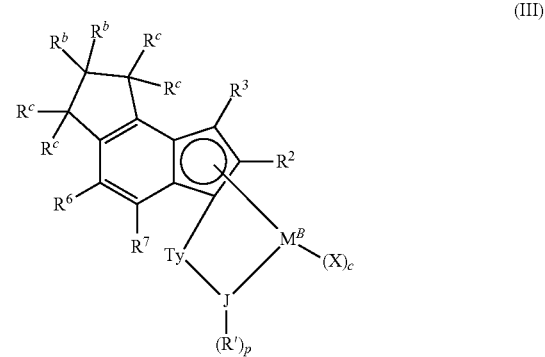

(III)

where M is group 3, 4, 5, or 6 transition metal; B is the oxidation state of M, and is 3, 4, 5 or 6; cis B-2; J is N, O, S or P; p is 2-y when J is N or P and 1-y when J is O or S; each $R^2$, $R^3$, $R^6$, and $R^7$, is independently hydrogen, or a $C_1$-$C_{50}$ substituted or unsubstituted hydrocarbyl, halocarbyl or silylcarbyl; each $R^b$ and $R^c$ is independently $C_1$-$C_{10}$ alkyl, or hydrogen; each R' is, independently, a $C_1$-$C_{100}$ substituted or unsubstituted hydrocarbyl, halocarbyl, silylcarbyl or germycarbyl; y is 0 or 1; T is $(CR^8R^9)_x$, $SiR^8R^9$ or $GeR^8R^9$ where x is 1 or 2, $R^8$ and $R^9$ are independently selected from hydrogen, substituted or unsubstituted hydrocarbyl, halocarbyl, silylcarbyl and germylcarbyl, and $R^8$ and $R^9$ may optionally be bonded together to form a ring structure; each X is, independently, a leaving group, or two Xs are joined and bound to the metal atom to form a metallocycle ring, or two Xs are joined to form a chelating ligand, a diene ligand, or an alkylidene.

4. The catalyst compound of paragraph 1, 2, or 3 wherein M is Ti.

5. The compound of paragraph 1, 2 or 3 where J is N, and R' and/or $R^i$ is methyl, ethyl, propyl, butyl, pentyl, hexyl, heptyl, octyl, nonyl, cyclooctyl, cyclododecyl, decyl, undecyl, dodecyl, adamantyl or an isomer thereof.

6. The catalyst compound of paragraph 2 wherein $R^2$, $R^3$, $R^4$, and/or $R^7$, are not aryl or substituted aryl.

7. The catalyst compound of paragraph 3 wherein $R^2$, $R^3$, $R^6$, and/or $R^7$, are not aryl or substituted aryl.

8. The compound of paragraph 2, wherein each $R^a$ is independently selected from the group consisting of methyl, ethyl, propyl, butyl, pentyl, hexyl and isomers thereof and each $R^c$ is independently selected from the group consisting of hydrogen, methyl, ethyl, propyl, butyl, pentyl, hexyl and isomers thereof.

9. The compound of paragraph 3 wherein both $R^b$, both $R^c$, or both $R^d$ are not hydrogen or are independently selected from the group consisting of hydrogen, methyl, ethyl, propyl, butyl, pentyl, hexyl and isomers thereof.

10. The compound of paragraph 1, wherein the sum of m+n+q is equal to 3, 4, 5, or 6.

11. The compound of paragraph 1, wherein Cp' is tetrahydro-s-indacenyl the 6 position is geminally disubstituted with two $C_1$-$C_{10}$ alkyl groups or Cp' is tetrahydro-as-indacenyl the 7 position is geminally disubstituted with two $C_1$-$C_{10}$ alkyl groups.

12. The compound of paragraph 1, wherein Cp' is tetrahydro-s-indacenyl and the 6 position is geminally disubstituted with two alkyl groups selected from the group consisting of methyl, ethyl, propyl, butyl, pentyl, hexyl, heptyl, octyl, nonyl, decyl, undecyl, and dodecyl and isomers thereof, or Cp' is tetrahydro-as-indacenyl and the 7 position is geminally disubstituted with two alkyl groups selected from the group consisting of methyl, ethyl, propyl, butyl, pentyl, hexyl, heptyl, octyl, nonyl, decyl, undecyl, and dodecyl and isomers thereof.

13. The compound of paragraph 1 wherein Cp' is tetrahydro-s-indacenyl and the 3 and 4 positions are not aryl or substituted aryl.

14. The compound of paragraph 3 wherein each $R^b$ is independently a $C_1$-$C_{10}$ alkyl.

15. The compound of paragraph 1, 2 or 3 where J is N, and R' is t-butyl, hexyl, neopentyl, cyclohexyl, cyclooctyl, cyclododecyl, adamantyl, or norbornyl.

16. The compound of paragraph 1, where the compound is any mono-tetrahydroindacenyl compound named herein.

17. A catalyst system comprising the compound of any of paragraphs 1 to 16 and an activator.

18. The catalyst system of paragraph 17, wherein the activator comprises a non-coordinating anion activator or an alumoxane.

19. The catalyst system of paragraph 17, where the catalyst system is supported (preferably wherein the catalyst system is a fluorided supported catalyst system preferably prepared by the method comprising combining a fluoride compound with polar solvent (such as water), then combining with a slurry of non-polar solvent and support, removing the non-polar solvent, thereafter combining the calcined support with a second solvent, which may be the same as or different from the non-polar solvent, and catalyst compounds and activators, wherein the fluorided support is calcined at a temperature from 100 to less than 400° C., before or after combination with the activator and/or catalyst compounds).

20. A process to produce olefin polymer comprising contacting olefin monomer with the catalyst system of any of paragraphs 17, 18 or 19.

21. The process of paragraph 20 wherein the monomer comprises ethylene and/or propylene.

22. The process of paragraph 20 or 21 wherein the catalyst system comprises one catalyst compound.

23. The process of paragraph 20, 21, or 22 wherein the process occurs at a temperature of from about 0° C. to about 300° C., at a pressure in the range of from about 0.35 MPa to about 10 MPa, and at a time up to 300 minutes.

24. The process of paragraph 20, 21, 22, or 23 wherein the monomer comprises two or more of ethylene, propylene, butene, pentene, hexene, heptene, octene, nonene, decene, undecene, or dodecene.

25. The process of paragraph 20, 21, 22, 23, or 24 wherein the monomer comprises ethylene and ethylidene norbornene.

Experimental

Room temperature is 23° C. unless otherwise noted.

The catalyst compounds used in the experiments were:

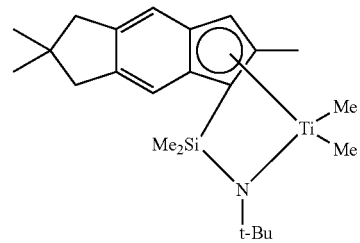

Cat A

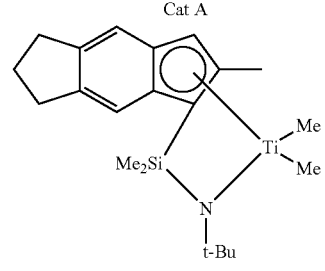

Comparative Cat D

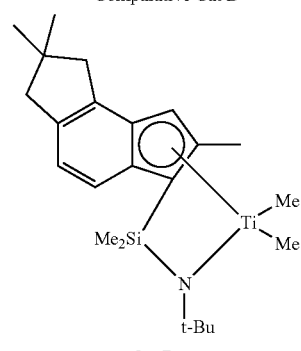

Cat B

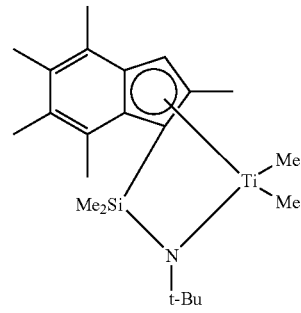

Comparative Cat C

Polymerization data (FIG. 1) for Catalyst A (black), catalyst B (dark grey), comparative catalyst C (light gray) and comparative catalyst D (white) (all at 0.04 µmol catalyst) show improved polymerization activity at both 70° C. and 100° C. polymerization temperature in make PP for catalysts A and B vs. the comparatives, C and D.

Polymerization data (FIG. 2) for Catalyst A (black), catalyst B (dark grey), comparative catalyst C (light gray) and comparative catalyst D (white) (0.10 µmol catalyst at 100° C. and 0.15 µmol catalyst at 110° C.) show improved polymerization activity at both 100° C. and 110° C. polymerization temperature in make PP for catalysts A and B vs. the comparatives, C and D.

Polymerization data (FIG. 3) for Catalyst A (black), catalyst B (dark grey), comparative catalyst C (light gray) and comparative catalyst D (white) showing improved propylene incorporation (less ethylene incorporation) while maintaining high polymer molecular weight.

Starting Reagents:

2-bromo-2-methylpropionyl bromide (Aldrich), $AlCl_3$ (Merck), $NaBH_4$ (Aldrich), TsOH (Aldrich), dichlorodimethylsilane (Merck), t-butylamine (Merck), 2.5 M $^n$BuLi in hexanes (Chemetall GmbH), MeMgBr in ether (Aldrich), $TiCl_4(THF)_2$ (Aldrich), 2-methylindan-1-one (Aldrich),), 1,2-bis(bromomethyl)benzene (Aldrich), iodomethane (Acros), $K_2CO_3$ (Merck), $Na_2CO_3$ (Aldrich), hydrazine hydrate (Merck), ethylene glycol (Merck), KOH (Merck), 37% hydrochloric acid (Merck), diethyl methylmalonate (Aldrich), sodium metal (Merck), anhydrous ethanol (Merck), thionyl chloride (Merck), potassium tert-butoxide (Acros), methanol (Merck), dichloromethane (Merck), hexane (Merck), toluene (Merck), silica gel 60 (40-63 um; Merck), and $CDCl_3$ (Deutero GmbH) were used as received. THF (Merck) and diethyl ether (Merck; ether) freshly distilled from benzophenone ketyl were used for organometallic synthesis and catalysis.

Synthesis of Pre-Catalyst A (Cat ID=A)

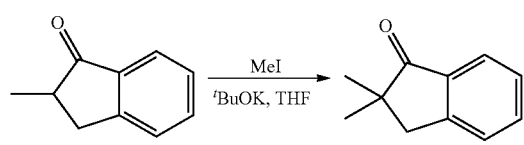

To a solution of 176 g (1.21 mol) of 2-methylindan-1-one and 205 g (1.44 mol, 1.2 eq.) of MeI in 200 ml of THF cooled to 0° C., a solution of 176 g (1.57 mol, 1.3 eq.) of $^t$BuOK in 1200 ml of THF was added dropwise for 4 h. The reaction mixture was stirred overnight at room temperature and then poured into 2 liters of water. Crude product was extracted with 300 ml of hexane and then 2×300 ml of dichloromethane. The combined organic extract was dried over $K_2CO_3$, passed through a short pad of silica gel 60 (40-63 um), and the eluent was evaporated to dryness to give red oil. This oil was then distilled in vacuum to give 185 g (96%) of 2,2-dimethylindan-1-one as yellowish oil which crystallizes at room temperature, b.p. 76-78° C./5 mm Hg.

Anal. calc. for $C_{11}H_{12}O$: C, 82.46; H, 7.55. Found: C, 82.24; H, 7.61.

$^1$H NMR ($CDCl_3$): δ 7.76 (d, 1H, J=7.6 Hz), 7.59 (dt, 1H, J=7.6, 1.2 Hz), 7.44-7.35 (m, 2H), 3.00 (s, 2H), 1.24 (s, 6H). $^{13}C\{^1H\}$ NMR ($CDCl_3$): δ 211.38, 152.18, 135.30, 134.77, 127.37, 126.59, 124.40, 45.43, 42.81, 25.22.

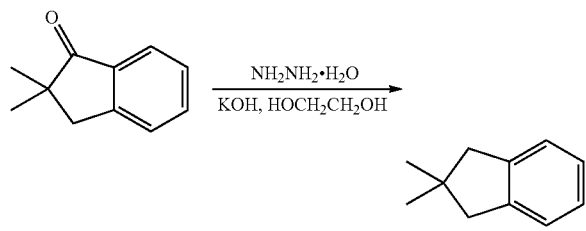

A mixture of 129 g (~2.3 mol) of KOH, 182.5 g (1.14 mol) of 2,2-dimethylindan-1-one and 144 ml of hydrazine hydrate in 850 ml of ethylene glycol was refluxed for 5 h. Then, the reflux condenser was replaced by a Claisen distillation head with condenser, and a mixture of $H_2O$, $NH_2NH_2$, product and ethylene glycol was distilled off until the distillation temperature reached 195° C. The residue was then allowed to cool to room temperature, 300 ml of ethylene glycol, second portion of 2,2-dimethylindan-1-one (182.5 g, 1.139 mol) and hydrazine hydrate (144 ml) was added, and the reduction procedure was repeated as described above. Upper layer of the combined distillate (from two successive reductions) was separated, and the aqueous phase was diluted with 1000 ml of water. Crude product was extracted with 3×300 ml of dichloromethane. The combined organic extract was washed by 1 M HCl, dried over $K_2CO_3$, passed through a short pad of silica gel 60 (40-63 um), and the elute was evaporated to dryness. The residue was distilled in vacuum to give 290 g (87%) of 2,2-dimethylindane as colorless liquid, b.p. 73.5° C./20 mm Hg.

Anal. calc. for $C_{11}H_{14}$: C, 90.35; H, 9.65. Found: C, 90.50; H, 9.73.

$^1$H NMR ($CDCl_3$): δ 7.19-7.08 (m, 4H, Ar—H), 2.72 (s, 4H, 2×CH$_2$ in indanyl), 1.15 (s, 6H, 2×CH$_3$ in indanyl). $^{13}C\{^1H\}$ NMR ($CDCl_3$): δ 143.51, 125.93, 124.70, 47.70, 40.05, 28.77.

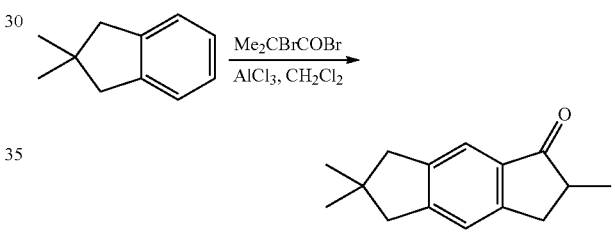

To a suspension of 420 g (3.15 mol, 2.66 eq.) of $AlCl_3$ in 400 ml of dichloromethane cooled to −40° C., 273 g (1.19 mol) of 2-bromo-2-methylpropionyl bromide and a solution of 173.5 g (1.19 mol) of 2,2-dimethylindane in 300 ml of dichloromethane were subsequently added for 30 min. The cooling bath was then removed, and the solution was stirred overnight at room temperature. The reaction mixture was poured into 2 kg of crushed ice, the organic phase was separated, and the water phase was extracted with 3×500 ml of dichloromethane. The combined organic extract was washed with aqueous $K_2CO_3$, dried over anhydrous $K_2CO_3$, passed through a short pad of silica gel 60 (40-63 um), and the eluent was evaporated to dryness to give a yellow oil. This oil was distilled in vacuum to give 245 g (96%) of 2,6,6-trimethyl-3,5,6,7-tetrahydro-s-indacen-1(2H)-one (on the evidence of NMR spectroscopy, this oil includes ca. 85-90% of the desired product) as slightly yellowish oil which crystallizes rapidly at room temperature, b.p. 153-165° C./1 mm Hg. This crude product was then re-crystallized from 700 ml of hot hexane. Crystals precipitated from this solution for one week at +5° C. were collected and dried in vacuum. This procedure gave 191 g (75%) of pure 2,6,6-trimethyl-3,5,6,7-tetrahydro-s-indacen-1(2H)-one as white crystalline solid. The mother liquor was evaporated to dryness to give 52.4 g of a ca. 1:1 mixture of the isomeric linear and angular indanones.

Anal. calc. for $C_{15}H_{18}O$: C, 84.07; H, 8.47. Found: C, 84.42; H, 8.60.

¹H NMR (CDCl₃): δ 7.52 (s, 1H, Ar—H), 7.21 (s, 1H, Ar—H), 3.32 (dd, 1H, J=16.5 Hz, J=7.1 Hz, 3-H in indan-1-one), 2.75, 2.73 (2×s, 4H, 2×CH₂ in indanyl), 2.77-2.58 (m, 2H, 2,3'-H in indan-1-one), 1.29 (d, 3H, J=7.3 Hz, 2-Me in indan-1-one), 1.15 (s, 6H, 2×CH₃ in indanyl).

¹³C{¹H} NMR (CDCl₃): δ 208.99, 152.64, 152.40, 143.51, 135.08, 122.43, 119.65, 47.78, 46.77, 42.28, 40.65, 34.74, 28.44, 16.44.

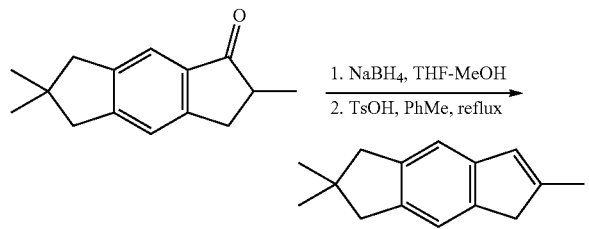

To a solution of 99.1 g (463 mmol) of 2,6,6-trimethyl-3,5,6,7-tetrahydro-s-indacen-1(2H)-one in 450 ml of THF cooled to 5° C., 26.3 g (695 mmol) of NaBH₄ was added. Further on, 225 ml of methanol was added dropwise by vigorous stirring for ca. 5 h at 5° C. The resulting mixture was stirred for 3 h at room temperature and then evaporated to dryness. The residue was partitioned between 500 ml of dichloromethane and 500 ml of 2 M HCl. The organic layer was separated, and the aqueous layer was extracted with 100 ml of dichloromethane. The combined organic extract was evaporated to dryness to give colorless oil. To a solution of this oil in 1000 ml of toluene 1 g of TsOH was added, and this mixture was refluxed with Dean-Stark head for 20 min, then cooled to room temperature using a water bath. The resulting solution was washed by 10% aqueous Na₂CO₃. The organic layer was separated, and the aqueous layer was extracted with 2×100 ml of dichloromethane. The combined organic extract was dried over K₂CO₃ and then passed through a short pad of silica gel 60 (40-63 um). The silica gel pad was additionally washed by 100 ml of dichloromethane. The combined organic elute was evaporated to dryness to yield yellowish liquid. This crude product was distilled in vacuum to give 77.7 g (85%) of 2,2,6-trimethyl-1,2,3,5-tetrahydro-s-indacene as yellowish oil which crystallizes rapidly at room temperature, b.p. 144-148° C./10 mm Hg.

Anal. calc. for C₁₅H₁₈: C, 90.85; H, 9.15. Found: C, 90.60; H, 9.04.

¹H NMR (CDCl₃): δ 7.14 (s, 1H, Ar—H), 7.03 (s, 1H, Ar—H), 6.41 (bs, 1H, vinylic Cp-H in indenyl), 3.21 (s, 2H, benzylic CH₂ in indenyl), 2.70 (s, 4H, 2×CH₂ in indanyl), 2.11 (s, 3H, 2-Me in indenyl), 1.14 (s, 6H, 2×CH₃ in indanyl). ¹³C{¹H} NMR (CDCl₃): δ 144.83, 144.22, 141.58, 141.35, 138.85, 127.08, 119.94, 116.08, 47.58, 47.53, 42.22, 40.25, 28.88, 16.79.

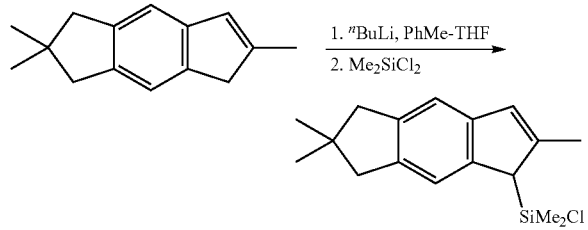

To a solution of 9.92 g (50.0 mmol) of 2,2,6-trimethyl-1,2,3,5-tetrahydro-s-indacene in 200 ml of toluene, 20.0 ml (50.0 mmol) of 2.5 M ⁿBuLi in hexanes was added at room temperature. The resulting viscous solution was stirred for 3 h, and then 20 ml of THF was added. The resulting suspension was stirred for 1 h at 60° C., then cooled to −30° C., and 20 ml (21.4 g, 166 mmol, 3.3 eq.) of dichlorodimethylsilane was added in one portion. The formed solution was refluxed for 1 h, then filtered through glass frit (G3). The precipitate was additionally washed by 50 ml of toluene. The combined filtrate was evaporated to dryness to give 14.7 g (100%) of chloro(dimethyl)(2,6,6-trimethyl-1,5,6,7-tetrahydro-s-indacen-1-yl)silane as viscous yellowish oil which was further used without an additional purification.

Anal. calc. for C₁₇H₂₃ClSi: C, 70.19; H, 7.97. Found: C, 70.44; H, 8.20.

¹H NMR (CDCl₃): δ 7.25 (s, 1H, Ar—H), 7.12 (s, 1H, Ar—H), 6.56 (s, 1H, vinylic Cp-H in indenyl), 3.49 (s, 1H, benzylic Cp-H in indenyl), 2.85-2.65 (m, 4H, C₅H₄Me₂), 2.26 (s, 3H, 2-Me), 1.19, 1.14 (2×s, 2×3H, C₅H₄Me₂), 0.40, 0.15 (2×s, 2×3H, SiMe₂Cl). ¹³C{¹H} NMR (CDCl₃): δ 144.41, 143.72, 141.26, 140.71, 138.70, 127.40, 119.94, 116.26, 49.33, 47.64, 47.55, 40.40, 28.85, 17.57, 1.07, −0.62.

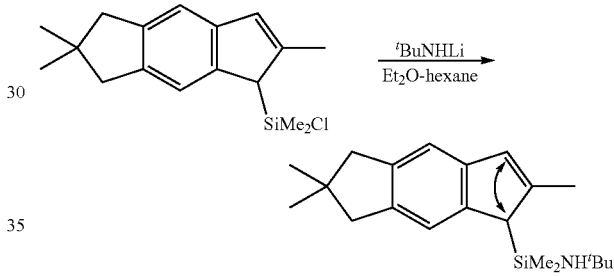

To a solution of 6.30 ml (4.39 g, 60 mmol, 1.2 eq.) of tert-butylamine in 150 ml of ether cooled to −50° C., 20 ml (50 mmol) of 2.5 M ⁿBuLi in hexanes was added. The reaction mixture was stirred for 4 h at room temperature, and to the formed suspension cooled to −78° C. a solution of 14.7 g (50 mmol) of chloro(dimethyl)(2,6,6-trimethyl-1,5,6,7-tetrahydro-s-indacen-1-yl)silane in 150 ml of ether was added. The resulting mixture was allowed to warm to room temperature and stirred overnight. Then, it was evaporated to dryness, and the residue was dissolved in 250 ml of toluene. This solution was filtered through glass frit (G3), and the precipitate was additionally washed by 50 ml of toluene. The filtrate was concentrated under vacuum to give viscous yellowish oil (15.6 g, 95%). On the evidence of NMR spectroscopy, this oil consists of two isomeric compounds, i.e. N-(tert-butyl)-1,1-dimethyl-1-(2,6,6-trimethyl-1,5,6,7-tetrahydro-s-indacen-1-yl)silanamine (allylic isomer, ca. 70%) and N-(tert-butyl)-1,1-dimethyl-1-(2,6,6-trimethyl-3,5,6,7-tetrahydro-s-indacen-1-yl)silanamine (vinylic isomer, ca. 30%).

Anal. calc. for C₂₁H₃₃NSi: C, 77.00; H, 10.15; N, 4.28. Found: C, 77.29; H, 10.40; N, 4.01. N-(tert-butyl)-1,1-dimethyl-1-(2,6,6-trimethyl-1,5,6,7-tetrahydro-s-indacen-1-yl)silanamine (allylic isomer): ¹H NMR (CDCl₃): δ 7.32 (s, 1H, Ar—H), 7.19 (s, 1H, Ar—H), 6.58 (s, 1H, vinylic Cp-H in indenyl), 3.39 (s, 1H, benzylic Cp-H in indenyl), 2.95-2.75 (m, 4H, C₅H₄Me₂), 2.35 (s, 3H, 2-Me), 1.35-1.21 (m, 15H, ᵗBu+C₅H₄Me₂), 0.68 (bs, 1H, NH), 0.24, 0.04 (2×s, 2×3H, SiMe₂).

N-(tert-butyl)-1,1-dimethyl-1-(2,6,6-trimethyl-3,5,6,7-tetrahydro-s-indacen-1-yl)silanamine (vinylic isomer): $^1$H NMR (CDCl$_3$): δ 7.54 (s, 1H, Ar—$\underline{H}$), 7.27 (s, 1H, Ar—$\underline{H}$), 3.40 (s, 2H, benzylic Cp-$\underline{H}$ in indenyl), 2.95-2.75 (m, 4H, C$_5$$\underline{H}_4$Me$_2$), 2.36 (s, 3H, 2-Me), 1.35-1.21 (m, 15H, $^t$$\underline{Bu}$+C$_5$H$_4$$\underline{Me}_2$), 0.89 (bs, 1H, N$\underline{H}$), 0.54 (s, 6H, Si$\underline{Me}_2$).

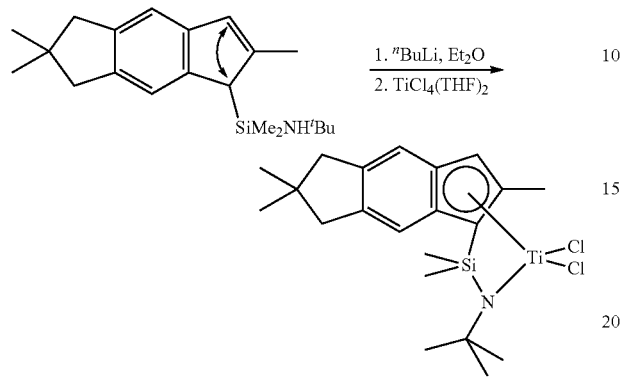

To a solution of 15.6 g (47.6 mmol) of N-(tert-butyl)-1,1-dimethyl-1-(2,6,6-trimethyl-tetrahydro-s-indacen-1-yl)silanamine (prepared above) in 200 ml of ether, 40.0 ml (100 mmol) of 2.5 M $^n$BuLi in hexanes was added in one portion at −78° C. This mixture was stirred for 4 h at room temperature, the resulting reddish solution was cooled to −78° C. and 16.7 g (50.0 mmol) of TiCl$_4$(THF)$_2$ was added in one portion. The formed mixture was stirred for 24 h at room temperature and then evaporated to dryness. The residue was extracted with 200 ml of warm toluene, and the formed hot suspension was filtered through glass frit (G3). The precipitate was additionally washed by 2×50 ml of hot toluene. The combined filtrate was evaporated to dryness, and the residue was extracted with 4×100 ml of warm hexane. The combined organic extract was evaporated to ca. 250 ml. Crystals precipitated from this solution overnight at room temperature were collected, washed by 10 ml of cold hexane, and dried in vacuum. This procedure gave 8.39 g (40%) of Me$_2$Si(η$^5$-2,6,6-trimethyl-1,5,6,7-tetrahydro-s-indacen-1-yl)(η$^1$-N$^t$Bu)TiCl$_2$. The mother liquor was concentrated to ca. 100 ml. Again, crystals precipitated from this solution overnight at room temperature were collected, washed by 10 ml of cold hexane, and dried in vacuum. This procedure gave 2.71 g (13%) of the target complex. Thus, the total yield of Me$_2$Si(η$^5$-2,6,6-trimethyl-1,5,6,7-tetrahydro-s-indacen-1-yl)(η$^1$-N$^t$Bu)TiCl$_2$ was 53%. Anal. calc. for C$_{21}$H$_{31}$Cl$_2$NSiTi: C, 56.76; H, 7.03; N, 3.15. Found: C, 56.90; H, 7.18; N, 2.97. $^1$H NMR (CDCl$_3$): δ 7.46 (s, 1H, Ar—$\underline{H}$), 7.40 (s, 1H, Ar—$\underline{H}$), 7.02 (s, 1H, Cp-$\underline{H}$ in indenyl), 2.85-2.67 (m, 4H, C$_5$$\underline{H}_4$Me$_2$), 2.34 (s, 3H, 2-Me), 1.38 (s, 9H, $^t$$\underline{Bu}$), 1.145, 1.138 (2×s, 2×3H, C$_5$H$_4$$\underline{Me}_2$), 0.90, 0.76 (2×s, 2×3H, Si$\underline{Me}_2$).

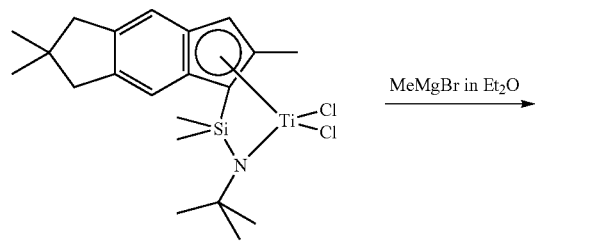

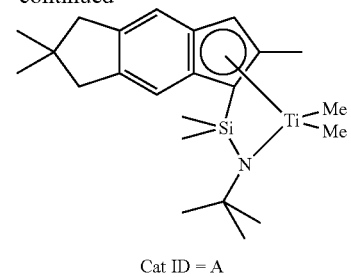

Cat ID = A

To a suspension of 8.39 g (35.9 mmol) of Me$_2$Si(η$^5$-2,6,6-trimethyl-1,5,6,7-tetrahydro-s-indacen-1-yl)(η$^1$-N$^t$Bu)TiCl$_2$ in 150 ml of ether cooled to −30° C., 28 ml (59.1 mmol, 3.1 eq.) of 2.11 M MeMgBr in ether was added in one portion. The reaction mixture was stirred overnight at room temperature and then evaporated to dryness. The residue was extracted with 4×50 ml of warm hexane. The combined extract was evaporated to ca. 30 ml and then filtered through glass frit (G3). Crystals precipitated from this filtrate overnight at −30° C. were collected, washed by 2×10 ml of cold (−30° C.) hexane, and dried in vacuum. This procedure gave 4.53 g (11.2 mmol, 60%) of Me$_2$Si(η$^5$-2,6,6-trimethyl-1,5,6,7-tetrahydro-s-indacen-1-yl)-(η$^1$-N$^t$Bu)TiMe$_2$. The mother liquor was concentrated to ca. 10 ml. Crystals precipitated from this solution overnight at −30° C. were collected, washed by 10 ml of cold (−30° C.) hexane, and dried in vacuum. This procedure gave 1.45 g (19%) of the target complex. Thus, the total yield of Me$_2$Si(η$^5$-2,6,6-trimethyl-1,5,6,7-tetrahydro-s-indacen-1-yl)(η$^1$-N$^t$Bu)TiMe$_2$ was 79%. Anal. calc. for C$_{23}$H$_{37}$NSiTi: C, 68.46; H, 9.24; N, 3.47. Found: C, 68.19; H, 9.36; N, 3.41. $^1$H NMR (CDCl$_3$): δ 7.42 (s, 1H, Ar—$\underline{H}$), 7.22 (s, 1H, Ar—$\underline{H}$), 6.94 (s, 1H, Cp-$\underline{H}$ in indenyl), 2.75 (s, 2H, C$_5$$\underline{H}_4$Me$_2$), 2.69 (d, 1H, J=15.47, C$_5$$\underline{H}_4$Me$_2$), 2.625 (d, 1H, J=15.47, C$_5$$\underline{H}_4$Me$_2$), 2.13 (s, 3H, 2-Me), 1.50 (s, 9H, $^t$$\underline{Bu}$), 1.13, 1.11 (2×s, 2×3H, C$_5$H$_4$$\underline{Me}_2$), 0.65, 0.56 (2×s, 2×3H, Si$\underline{Me}_2$), 0.5, −0.52 (2×s, 2×3H, Ti$\underline{Me}_2$).

Synthesis of Pre-Catalyst B (Cat ID=B)

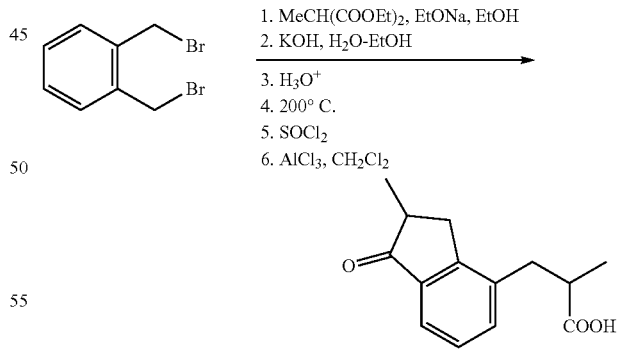

In a three-necked round-bottom flask, 46.0 g (2.0 mol) of sodium metal was dissolved in 1100 ml of dry ethanol. To the resulting solution, 349 g (2.0 mol) of diethyl methylmalonate was added. This mixture was stirred for 15 min., then 264 g (1.0 mol) of 1,2-bis(bromomethyl)benzene was added in portions at such a rate as to maintain a gentle reflux. This mixture was refluxed for 3 h and then cooled to room temperature. A solution of 411 g of KOH in 1200 ml of water was added. The resulting mixture was refluxed for 6 h to saponificate the ester formed. Ethanol and water were distilled off until temperature reached 95° C., and 4 liters of water and then 12 M HCl (to pH 1) were added to the residue. The precipitated acid was filtered off, washed with 3×500 ml of water, and then decarboxylated at 200° C. to give 3,3'-(1,2-phenylene)bis(2-methylpropanoic acid).

$^1$H NMR (CDCl$_3$): δ 11.4 (bs, 2H, COOH), 7.16 (s, 4H, Ar—H), 3.20-3.11 (m, 2H, 3-H in propanoic acid), 2.79-2.63 (m, 4H, 2,3'-H in propanoic acid), 1.195 (d, 6H, J=6.57, 2-Me in propanoic acid). $^{13}$C{$^1$H} NMR (CDCl$_3$): δ 182.78, 137.29, (129.92, 129.85), 126.61, (40.66, 40.62), 35.66, (16.63, 16.57). [in parentheses—diastereomeric signals.]

A mixture of this acid and 511 ml of SOCl$_2$ was stirred at room temperature for 24 hours. An excess of thionyl chloride was distilled off, and the residue was dried in vacuum to give crude 3,3'-(1,2-phenylene)bis(2-methylpropanoyl chloride) which was further used without an additional purification.

To a stirred suspension of 166.5 g (1.25 mol) of AlCl$_3$ in 1200 ml of dichloromethane cooled to 0° C., a solution of 3,3'-(1,2-phenylene)bis(2-methylpropanoyl chloride) (prepared above) in 200 ml of dichloromethane was added dropwise. This mixture was stirred overnight at room temperature and then poured on 2 kg of ice. The organic layer was separated, and the aqueous layer was additionally extracted with 3×250 ml of dichloromethane. The combined organic extract was evaporated to dryness, and the residue was dissolved in a cold solution of 100 g KOH in 1200 ml H$_2$O. The obtained solution was extracted with 2×200 ml of ether, then acidified with 12 M HCl to pH 1. Resulting mixture was extracted with 3×400 ml of dichloromethane. The combined organic extract was passed through a short pad of silica gel 60 (40-63 um), and the elute was evaporated to dryness to give 147.5 g (64%) of 2-methyl-3-(2-methyl-1-oxo-2,3-dihydro-1H-inden-4-yl)propanoic acid as yellow oil which was further used without an additional purification.

$^1$H NMR (CDCl$_3$): δ 10.2 (bs, 1H, COOH), 7.65 (d, 1H, J=7.58 Ar—H), 7.43 (d, 1H, J=7.58 Ar—H), 7.33 ('t', 1H, J=7.58 Ar—H), 3.43-3.33 (m, 1H), 3.16-3.11 (m, 1H), 2.87-2.81 (m, 1H), 2.76-2.63 (m, 3H), 1.32, 1.31 (2×d, 3H, J=7.32, 2-Me in propanoic acid), 1.25 (d, 3H, J=6.83 Hz, CH$_3$ in indan-1-one). $^{13}$C{$^1$H} NMR (CDCl$_3$): δ 209.79, (181.54, 181.50), 152.27, 136.86, 136.46, 134.93, 127.76, 122.35, 41.87, 39.84, 35.23, 33.60, 16.86, 16.29. [$^2$in parentheses—diastereomeric signals.]

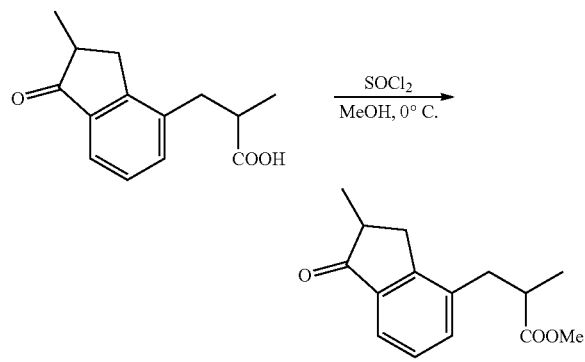

To a solution of 408 g (1.76 mol) of 2-methyl-3-(2-methyl-1-oxo-2,3-dihydro-1H-inden-4-yl)propanoic acid in 1400 ml of MeOH cooled to 0° C., 154 ml (251 g, 2.11 mol, 1.2 eq.) of thionyl chloride was added dropwise for 2 h. This mixture was allowed to reach room temperature and then refluxed for 0.5 h. The obtained mixture was evaporated on Rotavap, the residue was dissolved in 1000 ml of dichloromethane. This solution was washed with aqueous K$_2$CO$_3$, dried over anhydrous K$_2$CO$_3$, and evaporated to dryness to give yellow oil. This oil was distilled in vacuum to give 335 g (78%) of methyl 2-methyl-3-(2-methyl-1-oxo-2,3-dihydro-1H-inden-4-yl)propanoate as yellowish oil, b.p. 162° C./3 mm Hg.

Anal. calc. for C$_{15}$H$_{18}$O$_3$: C, 73.15; H, 7.37. Found: C, 73.56; H, 7.61.

$^1$H NMR (CDCl$_3$): 7.62 (d, 1H, J=7.58 Ar—H), 7.39 (d, 1H, J=7.58 Ar—H), 7.31 ('t', 1H, J=7.58 Ar—H), 3.63 (s, 3H, COOMe), 3.42-3.32 (m, 1H), 3.12-3.07 (m, 1H), 2.86-2.61 (m, 4H), 1.32, 1.31 (2×d, 3H, J=6.57, 2-Me in propanoic acid), 1.21, 1.21 (2×d, 3H, J=6.57 Hz, CH$_3$ in indan-1-one). $^{13}$C{$^1$H} NMR (CDCl$_3$): δ 209.37, 176.14, 152.12, 137.15, 136.52, 134.81, 127.67, 122.20, 51.66, (41.92, 41.88), (40.00, 39.97), 35.64, 33.62, (17.11, 17.08), (16.31, 16.27). [$^3$ in parentheses—diastereomeric signals.]

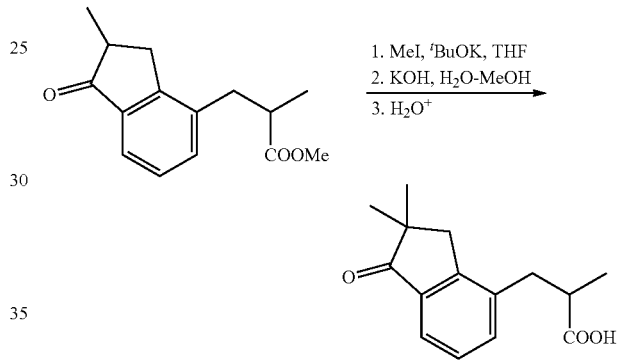

To a mixture of 335 g (1.36 mol) of methyl 2-methyl-3-(2-methyl-1-oxo-2,3-dihydro-1H-inden-4-yl)propanoate and 232 g (1.63 mol, 1.2 eq.) of MeI cooled to 0° C., a solution of 183 g (1.63 mol, 1.2 eq.) of $^t$BuOK in 1200 ml of THF was added dropwise for 4 h, and the reaction mixture was then stirred overnight at room temperature. Further on, this mixture was evaporated on Rotavap. To the residue a solution of 150 g of KOH in 800 ml of water and 250 ml of MeOH was added. The resulting mixture was refluxed for 4 h to saponificate the ester. Further on, MeOH and water were distilled off until temperature reached 95° C., and 3 liters of water and then 12 M HCl (to pH 1) were added to the residue. Crude product was extracted with 500 ml of dichloromethane. The aqueous phase was additionally extracted with 3×250 ml of dichloromethane. The combined organic extract was evaporated to dryness, and the residue was re-crystallized from a ca. 5:1 mixture of hexane and benzene to give 296 g (88%) of 3-(2,2-dimethyl-1-oxo-2,3-dihydro-1H-inden-4-yl)-2-methylpropanoic acid.

$^1$H NMR (CDCl$_3$): δ 7.66 (d, 1H, J=7.58 Ar—H), 7.44 (d, 1H, J=7.58 Ar—H), 7.34 ('t', 1H, J=7.58 Ar—H), 3.115 (dd, 1H, J=13.64 Hz, J=6.82 Hz, 3-H in propanoic acid), 2.99, 2.93 (2×d, 2×1H, CH$_2$ in indan-1-one), 2.825 (m, 1H, 2-H in propanoic acid), 2.72 (dd, 1H, J=13.64 Hz, J=7.83 Hz, 3'-H in indan-1-one), 1.25 (d, 3H, J=6.82 Hz, 2-Me in propanoic acid), 1.25, 1.24 (2×s, 2×3H, 2×CH$_3$ in indan-1-one). $^{13}$C{$^1$H} NMR (CDCl$_3$): δ 211.67, 181.80, 150.98, 136.87, 135.44, 135.06, 127.84, 122.83, 45.45, 41.54, 39.92, 35.22, 25.27, 16.86.

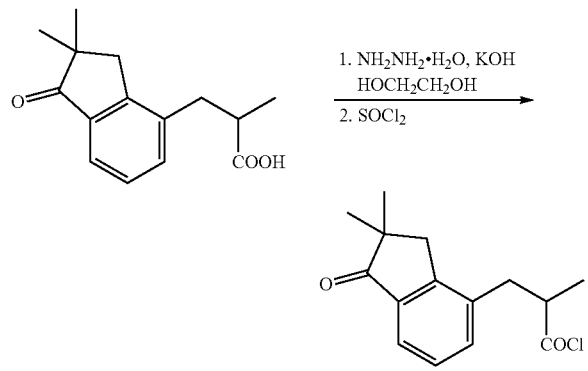

1. NH$_2$NH$_2$·H$_2$O, KOH
   HOCH$_2$CH$_2$OH
2. SOCl$_2$

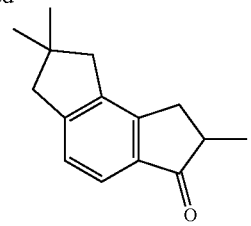

To a solution of 296 g (1.2 mol) of 3-(2,2-dimethyl-1-oxo-2,3-dihydro-1H-inden-4-yl)-2-methylpropanoic acid in a mixture of 260 g (~4.6 mol) of KOH and 2500 ml of ethylene glycol, 252 ml of hydrazine hydrate was added. The reaction mixture was refluxed for 5 h. Then, the reflux condenser was replaced by a Claisen distillation head with condenser, and a mixture of H$_2$O, NH$_2$NH$_2$ and ethylene glycol was slowly distilled off until the distillation temperature reached 195° C. The residue was then allowed to cool to room temperature, poured into 5 liters of water, acidified with 12 N HCl to pH=1, and extracted with 1 liter of dichloromethane. The aqueous phase was additionally extracted with 2×500 ml of dichloromethane. The combined organic extract was washed with 1 liter of water and evaporated to dryness to give 3-(2,2-dimethyl-2,3-dihydro-1H-inden-4-yl)-2-methylpropanoic acid as red viscous oil. $^1$H NMR (CDCl$_3$): δ 7.1-7.0 (m, 2H, Ar—H), 6.94 (d, 1H, J=7.08 Hz, Ar—H), 3.02 (dd, 1H, J=13.5 Hz, J=6.2 Hz, 3-H in propanoic acid), 2.79-2.64 (m, 5H, 2×CH$_2$ in indanyl and 2-H in propanoic acid), 2.59 (dd, 1H, J=13.5 Hz, J=8.4 Hz, 3'-H in indan-1-one), 1.17 (d, 3H, J=7.07 Hz, 2-Me in propanoic acid), 1.14 (s, 6H, 2×CH$_3$ in indanyl). $^{13}$C{$^1$H} NMR (CDCl$_3$): δ 182.86, 143.75, 142.33, 135.09, 126.71, 126.27, 122.92, 47.86, 46.18, 40.27, 39.71, 36.76, 28.83, 16.49.

A mixture of the above-obtained acid and 307 ml (501 g, 4.21 mol) of thionyl chloride was stirred for 24 h at room temperature. An excess of thionyl chloride was distilled off, the residue was distilled in vacuum to give 270 g [90% from 3-(2,2-dimethyl-1-oxo-2,3-dihydro-1H-inden-4-yl)-2-methylpropanoic acid] of 3-(2,2-dimethyl-2,3-dihydro-1H-inden-4-yl)-2-methylpropionyl chloride, b.p. 138-150° C./2 mm Hg.

$^1$H NMR (CDCl$_3$): δ 7.15-7.0 (m, 2H, Ar—H), 6.93 (d, 1H, J=7.08 Hz, Ar—H), 3.19-3.06 (m, 2H), 2.77-2.6 (m, 5H), 1.265 (d, 3H, J=7.07 Hz, 2-Me in propionyl chloride), 1.16, 1.15 (2×s, 2×3H, 2×CH$_3$ in indanyl). $^{13}$C{$^1$H} NMR (CDCl$_3$): δ 177.19, 144.04, 142.31, 133.64, 126.75, 126.49, 123.39, 52.25, 47.80, 46.19, 39.84, 36.71, 28.80, 16.59.

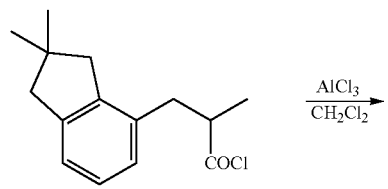

AlCl$_3$ / CH$_2$Cl$_2$

-continued

To a suspension of 173 g (1.29 mol, 1.2 eq.) of AlCl$_3$ in 1000 ml of dichloromethane cooled to 0° C., a solution of 270 g (1.08 mol) of 3-(2,2-dimethyl-2,3-dihydro-1H-inden-4-yl)-2-methylpropionyl chloride in 2500 ml of dichloromethane was added for 1 h. The cooling bath was then removed, and the solution was stirred overnight at room temperature. The reaction mixture was poured into 2 kg of crushed ice, the organic phase was separated, and the water phase was extracted by 3×500 ml of dichloromethane. The combined organic extract was washed with aqueous K$_2$CO$_3$, dried over anhydrous K$_2$CO$_3$, passed through a short pad of silica gel 60 (40-63 um), and the elute was evaporated to dryness. The residue was distilled in vacuum to give 223 g (97%) of 2,7,7-trimethyl-1,6,7,8-tetrahydro-as-indacen-3(2H)-one as yellowish oil which crystallizes at room temperature, b.p. 137-138° C./1 mm Hg.

Anal. calc. for C$_{15}$H$_{18}$O: C, 84.07; H, 8.47. Found: C, 84.42; H, 8.69.

$^1$H NMR (CDCl$_3$): δ 7.565 (d, 1H, J=7.58 Hz, Ar—H), 7.18 (d, 1H, J=7.58 Hz, Ar—H), 3.24 (dd, 1H, J=17.2 Hz, J=7.8 Hz, 3-H in indan-1-one), 2.80, 2.71 (2×s, 4H, 2×CH$_2$ in indanyl), 2.75-2.65 (m, 1H, 2-H in indan-1-one), 2.56 (dd, 1H, J=17.2 Hz, J=3.54 Hz, 3'-H in indan-1-one), 1.31 (d, 3H, J=7.58 Hz, 2-Me in indan-1-one), 1.20, 1.18 (2×s, 2×3H, 2×CH$_3$ in indanyl). $^{13}$C{$^1$H} NMR (CDCl$_3$): δ 209.31, 151.10, 149.82, 140.60, 134.81, 123.97, 122.22, 48.12, 44.86, 42.13, 40.34, 33.48, 28.90, 16.46.

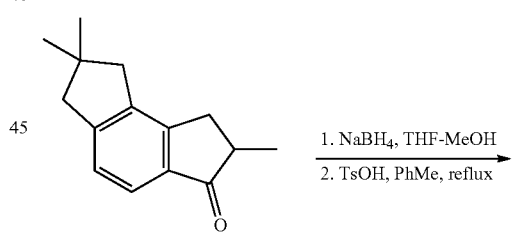

1. NaBH$_4$, THF-MeOH
2. TsOH, PhMe, reflux

To a solution of 94.9 g (442.8 mmol) of 2,7,7-trimethyl-1,6,7,8-tetrahydro-as-indacen-3(2H)-one in 440 ml of THF cooled to 5° C., 25.1 g (664 mmol) of NaBH$_4$ was added. Further on, 220 ml of methanol was added dropwise to this vigorously stirred mixture for ca. 5 h at 5° C. The resulting mixture was stirred for 3 h at room temperature, then evaporated to dryness, and the residue was partitioned between 500 ml of dichloromethane and 500 ml of 2 M HCl. The organic layer was separated, and the aqueous layer was additionally extracted with 100 ml of dichloromethane. The combined organic extract was evaporated to dryness. To a solution of the residue in 900 ml of toluene 1 g of TsOH was added, and this mixture was refluxed with Dean-Stark head for 20 min., then cooled to room temperature using a water bath. The resulting solution was washed by 10% aqueous $Na_2CO_3$. The organic layer was separated, and the aqueous layer was extracted with 2×100 ml of dichloromethane. The combined organic extract was dried over $K_2CO_3$ and then passed through a short pad of silica gel 60 (40-63 um). The silica gel pad was additionally washed by 100 ml of dichloromethane. The combined organic elute was evaporated to dryness. This crude product was distilled in vacuum to give 79.6 g (91%) of 2,2,7-trimethyl-1,2,3,6-tetrahydro-as-indacene as yellowish oil which crystallizes rapidly at room temperature, b.p. 119-125° C./2 mm Hg. Anal. calc. for $C_{15}H_{18}$: C, 90.85; H, 9.15. Found: C, 90.76; H, 9.24. $^1H$ NMR (CDCl$_3$): δ 7.06-6.99 (m, 2H, Ar—H), 6.45 (bs, 1H, vinylic Cp-H in indenyl), 3.13 (s, 2H, benzylic CH$_2$ in indenyl), 2.74, 2.67 (2×s, 2×2H, 2×CH$_2$ in indanyl), 2.13 (s, 3H, 2-Me in indenyl), 1.16 (s, 6H, 2×CH$_3$ in indanyl). $^{13}C\{^1H\}$ NMR (CDCl$_3$): δ 144.40, 144.10, 139.37, 139.08, 138.18, 127.32, 122.41, 117.62, 47.66, 45.87, 41.19, 40.26, 29.09, 16.77.

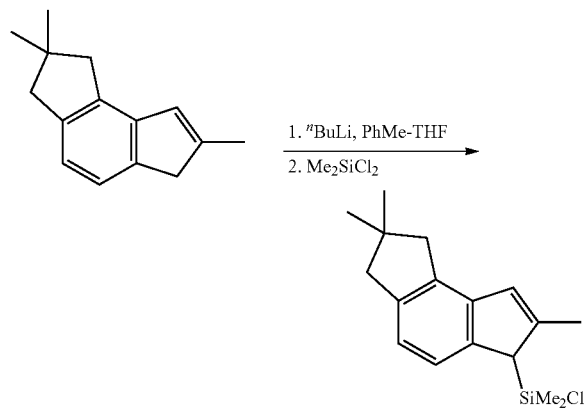

To a solution of 9.92 g (50.0 mmol) of 2,2,7-trimethyl-1,2,3,6-tetrahydro-as-indacene in 200 ml of toluene 20.0 ml (50.0 mmol) of 2.5 M $^n$BuLi in hexanes was added at room temperature. The resulting viscous solution was stirred for 3 h, then 20 ml of THF was added. The resulting mixture was stirred for 1 h at 60° C., then cooled to −30° C., and 20 ml (21.4 g, 166 mmol, 3.3 eq.) of dichlorodimethylsilane was added in one portion. The resulting solution was warmed to room temperature and then refluxed for 1 h. The resulting mixture was filtered through glass frit (G3), and the precipitate was additionally washed by 50 ml of toluene. The combined filtrate was evaporated to dryness to give 14.6 g (~100%) of chloro(dimethyl)(2,7,7-trimethyl-3,6,7,8-tetrahydro-as-indacen-3-yl)silane as viscous yellowish liquid which was further used without an additional purification. $^4$containing 10% of unknown impurity with the same set of signals in the $^1H$ NMR spectrum. Anal. calc. for $C_{17}H_{23}ClSi$: C, 70.19; H, 7.97. Found: C, 70.44; H, 8.31. $^1H$ NMR (CDCl$_3$): δ 7.27 (d, 1H, J=7.64 Hz, Ar—H), 6.98 (d, 1H, J=7.64 Hz, Ar—H), 6.60 (s, 1H, vinylic Cp-H in indenyl), 3.58 (s, 1H, benzylic Cp-H in indenyl), 2.83 (s, 2H, C$_5$H$_4$Me$_2$), 2.81, 2.80 (2×s, 2×H, C$_5$H$_4$Me$_2$), 2.33 (s, 3H, 2-Me), 1.24, 1.21 (2×s, 2×3H, C$_5$H$_4$Me$_2$), 0.47, 0.14 (2×s, 2×3H, SiMe$_2$Cl).

$^{13}C\{^1H\}$ NMR (CDCl$_3$): δ 145.98, 141.51, 141.21, 140.26, 134.58, 125.61, 121.22, 119.43, 49.84, 47.80, 45.96, 40.39, 29.06, 17.70, 1.28, −0.91.

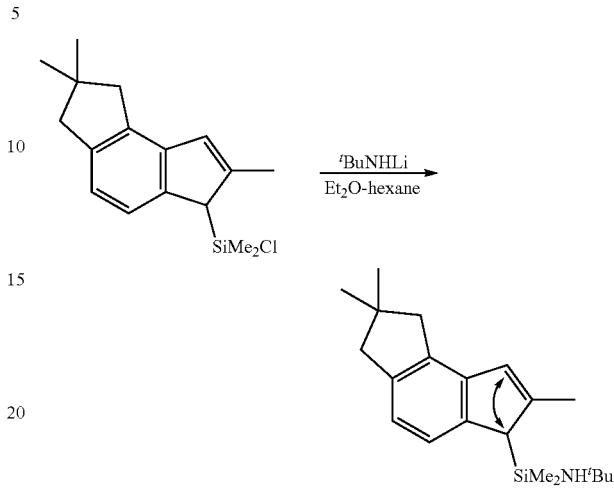

To a solution of 6.3 ml (4.39 g, 60 mmol) of tert-butylamine in 150 ml of ether cooled to −50° C., 18 ml (45 mmol) of 2.5 M $^n$BuLi in hexanes was added. This mixture was stirred for 4 h at room temperature, and to the resulting suspension cooled to −78° C. a solution of 14.6 g (~50 mmol) of chloro(dimethyl)(2,7,7-trimethyl-3,6,7,8-tetrahydro-as-indacen-3-yl)silane in 150 ml of ether was added. The resulting mixture was allowed to warm to room temperature and stirred overnight. Then, it was evaporated to dryness, and the residue was dissolved in 200 ml of toluene. This solution was filtered through glass frit (G3), and the precipitate was additionally washed by 50 ml of toluene. The combined filtrate was evaporated to dryness to give viscous yellowish oil (15.7 g, 96%). On the evidence of NMR spectroscopy, this product consists of two isomeric compounds, i.e.: N-(tert-butyl)-1,1-dimethyl-1-(2,7,7-trimethyl-3,6,7,8-tetrahydro-as-indacen-3-yl)silanamine (allylic isomer, ca. 70%) and N-(tert-butyl)-1,1-dimethyl-1-(2,7,7-trimethyl-1,6,7,8-tetrahydro-as-indacen-3-yl)silanamine (vinylic isomer, ca. 30%), and ca. 10% of unknown impurity. It was further used without an additional purification. Anal. calc. for $C_{21}H_{33}NSi$: C, 77.00; H, 10.15; N, 4.28. Found: C, 77.55; H, 9.90; N, 4.03. N-(tert-butyl)-1,1-dimethyl-1-(2,7,7-trimethyl-3,6,7,8-tetrahydro-as-indacen-3-yl)silanamine (allylic isomer): $^1H$ NMR (CDCl$_3$): δ 7.34 (d, 1H, J=7.64 Hz, Ar—H), 7.01 (d, 1H, J=7.64 Hz, Ar—H), 6.60 (s, 1H, vinylic Cp-H in indenyl), 3.47 (s, 1H, benzylic Cp-H in indenyl), 2.91 (s, 2H, C$_5$H$_4$Me$_2$), 2.89, 2.88 (2×s, 2×H, C$_5$H$_4$Me$_2$), 2.40 (s, 3H, 2-Me), 1.36-1.26 (m, 15H, $^t$Bu+C$_5$H$_4$Me$_2$), 0.70 (bs, 1H, NH), 0.26, 0.05 (2×s, 2×3H, SiMe$_2$).

N-(tert-butyl)-1,1-dimethyl-1-(2,7,7-trimethyl-1,6,7,8-tetrahydro-as-indacen-3-yl)silanamine (vinylic isomer): $^1H$ NMR (CDCl$_3$): δ 7.57 (d, 1H, J=7.83 Hz, Ar—H), 7.17 (d, 1H, J=7.83 Hz, Ar—H), 3.33 (s, 2H, benzylic Cp-H in indenyl), 2.61 (s, 2H, C$_5$H$_4$Me$_2$), 2.93, 2.89 (2×s, 2×H, C$_5$H$_4$Me$_2$), 2.40 (s, 3H, 2-Me), 1.36-1.26 (m, 15H, $^t$Bu+C$_5$H$_4$Me$_2$), 0.92 (bs, 1H, NH), 0.56 (s, 6H, SiMe$_2$).

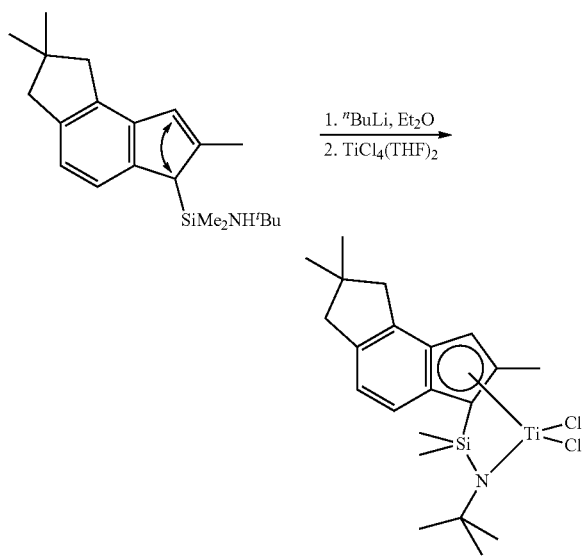

To a solution of 15.7 g (47.9 mmol) of N-(tert-butyl)-1,1-dimethyl-1-(2,7,7-trimethyl-tetrahydro-as-indacen-3-yl)silanamine (prepared above) in 150 ml of ether, 40.0 ml (100 mmol) of 2.5 M "BuLi in hexanes was added in one portion at −78° C. This mixture was stirred 5 h at room temperature, the resulting reddish solution was cooled to −78° C., and 16.7 g (50.0 mmol) of TiCl$_4$(THF)$_2$ was added in one portion. The obtained mixture was stirred for 24 h at room temperature and then evaporated to dryness. The residue was extracted with 150 ml of hot toluene, and this hot extract was filtered through glass frit (G3). The precipitate was additionally washed by 50 ml of hot toluene. The combined filtrate was evaporated to dryness, and the residue was extracted by 3×75 ml of hot hexane. The combined extract was evaporated to ca. 50 ml. Crystals precipitated from this solution overnight at room temperature were collected, washed by 15 ml of hexane, and dried in vacuum. This procedure gave 7.67 g (17.3 mmol, 36%) of Me$_2$Si($\eta^5$-2,7,7-trimethyl-3,6,7,8-tetrahydro-as-indacen-3-yl)-($\eta^1$-N$^t$Bu)TiCl$_2$. The mother liquor was concentrated to ca. 30 ml. Crystals precipitated from this solution overnight at room temperature were collected, washed by 10 ml of hexane, and dried in vacuum. This procedure gave 2.43 g (11%) of the target complex. Thus, the total yield of Me$_2$Si($\eta^5$-2,7,7-trimethyl-3,6,7,8-tetrahydro-as-indacen-3-yl)($\eta^1$-N$^t$Bu)TiCl$_2$ was 48%.

Anal. calc. for C$_{21}$H$_{31}$Cl$_2$NSiTi: C, 56.76; H, 7.03; N, 3.15. Found: C, 56.90; H, 7.19; N, 3.21. $^1$H NMR (CDCl$_3$): δ 7.57 (d, 1H, J=8.71 Hz, Ar—H), 7.12 (d, 1H, J=8.71 Hz, Ar—H), 6.94 (s, 1H, Cp-H in indenyl), 2.90-2.75 (m, 4H, C$_5$H$_4$Me$_2$), 2.38 (s, 3H, 2-Me), 1.37 (s, 9H, $^t$Bu), 1.24, 1.21 (2×s, 2×3H, C$_5$H$_4$Me$_2$), 0.91, 0.77 (2×s, 2×3H, SiMe$_2$).

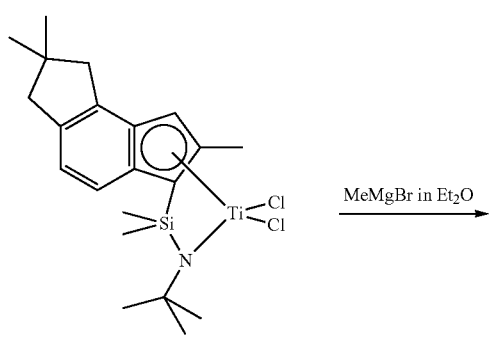

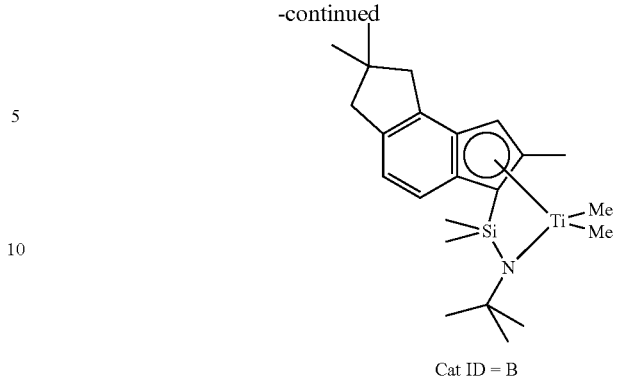

Cat ID = B

To a solution of 7.67 g (17.3 mmol) of Me$_2$Si($\eta^5$-2,7,7-trimethyl-3,6,7,8-tetrahydro-as-indacen-3-yl)($\eta^1$-N$^t$Bu)TiCl$_2$ in 150 ml of ether cooled to −30° C., 25 ml (52.8 mmol, 3.1 eq.) of 2.11 M MeMgBr in ether was added in one portion, and the reaction mixture was stirred for 1 h at room temperature, then evaporated to dryness. The residue was extracted with 4×50 ml of hot hexane. The combined extract was evaporated to ca. 30 ml, filtered through glass frit (G3), and then concentrated to ca. 10 ml. Yellow crystals precipitated from this solution overnight at room temperature were collected, washed by 3×10 ml of cold (−30° C.) hexane, and dried in vacuum. This procedure gave 2.65 g (38%) of Me$_2$Si($\eta^5$-2,7,7-trimethyl-3,6,7,8-tetrahydro-as-indacen-3-yl)($\eta^1$-N$^t$Bu)TiMe$_2$. The mother liquor was concentrated to ca. 15 ml. Crystals precipitated from this solution overnight at room temperature were collected, washed by 2×7 ml of cold (−30° C.) hexane, and dried in vacuum. This procedure gave 2.57 g (37%) of the target complex. This procedure repeated for the obtained mother liquor gave additional 0.63 g (9%) of the desired compound. Thus, the total yield of Me$_2$Si($\eta^5$-2,7,7-trimethyl-3,6,7,8-tetrahydro-as-indacen-3-yl)-($\eta^1$-N$^t$Bu)TiMe$_2$ was 84%. Anal. calc. for C$_{23}$H$_{37}$NSiTi: C, 68.46; H, 9.24; N, 3.47. Found: C, 68.54; H, 9.15; N, 3.29. $^1$H NMR (CDCl$_3$): δ 7.29 (d, 1H, J=8.71 Hz, Ar—H), 6.93 (d, 1H, J=8.71 Hz, Ar—H), 6.87 (s, 1H, Cp-H in indenyl), 3.00-2.72 (m, 4H, C$_5$H$_4$Me$_2$), 2.16 (s, 3H, 2-Me), 1.49 (s, 9H, $^t$Bu), 1.24, 1.20 (2×s, 2×3H, C$_5$H$_4$Me$_2$), 0.66, 0.57 (2×s, 2×3H, SiMe$_2$), 0.50, −0.60 (2×s, 2×3H, TiMe$_2$).

Polymerization Examples

Solutions of the pre-catalysts (Catalyst A or B, prepared above, or comparative compounds C or D) were made using toluene (ExxonMobil Chemical Company—anhydrous, stored under N2) (98%). Pre-catalyst solutions were typically 0.5 mmol/L.

Solvents, polymerization grade toluene and/or isohexanes were supplied by ExxonMobil Chemical Company and are purified by passing through a series of columns: two 500 cc Oxyclear cylinders in series from Labclear (Oakland, Calif.), followed by two 500 cc columns in series packed with dried 3 Å mole sieves (8-12 mesh; Aldrich Chemical Company), and two 500 cc columns in series packed with dried 5 Å mole sieves (8-12 mesh; Aldrich Chemical Company).

1-octene (C8; 98%, Aldrich Chemical Company) was dried by stirring over NaK overnight followed by filtration through basic alumina (Aldrich Chemical Company, Brockman Basic 1).

Polymerization grade ethylene (C2) was used and further purified by passing it through a series of columns: 500 cc Oxyclear cylinder from Labclear (Oakland, Calif.) followed by a 500 cc column packed with dried 3 Å mole sieves (8-12 mesh; Aldrich Chemical Company), and a 500 cc column packed with dried 5 Å mole sieves (8-12 mesh; Aldrich Chemical Company).

Polymerization grade propylene (C3) was used and further purified by passing it through a series of columns: 2250 cc Oxiclear cylinder from Labclear followed by a 2250 cc column packed with 3 Å mole sieves (8-12 mesh; Aldrich Chemical Company), then two 500 cc columns in series packed with 5 Å mole sieves (8-12 mesh; Aldrich Chemical Company), then a 500 cc column packed with Selexsorb CD (BASF), and finally a 500 cc column packed with Selexsorb COS (BASF).

Activation of the pre-catalysts was by dimethylanilinium tetrakisperfluorophenylborate (Boulder Scientific and Albemarle Corp) typically used as a 5 mmol/L solution in toluene. The molar ratio of activator to pre-catalyst was 1.1. For polymerization runs using dimethylanilinium tetrakisperfluorophenylborate, tri-n-octylaluminum (TnOAl, neat, AkzoNobel) was also used as a scavenger prior to introduction of the activator and pre-catalyst into the reactor. TnOAl was typically used as a 5 mmol/L solution in toluene.

Reactor Description and Preparation:

Polymerizations were conducted in an inert atmosphere ($N_2$) drybox using autoclaves equipped with an external heater for temperature control, glass inserts (internal volume of reactor=23.5 mL for C2 and C2/C8; 22.5 mL for C3 runs), septum inlets, regulated supply of nitrogen, ethylene and propylene, and equipped with disposable PEEK mechanical stirrers (800 RPM). The autoclaves were prepared by purging with dry nitrogen at 110° C. or 115° C. for 5 hours and then at 25° C. for 5 hours.

Ethylene Polymerization (PE) or Ethylene/1-Octene Copolymerization (EO):

The reactor was prepared as described above, and then purged with ethylene. For dimethylanilinium tetrakisperfluorophenylborate activated runs, toluene, 1-octene (100 μL when used) and scavenger (TnOAl, 0.5 μmol) were added via syringe at room temperature and atmospheric pressure. The reactor was then brought to process temperature (80° C.) and charged with ethylene to process pressure (75 psig=618.5 kPa or 200 psig=1480.3 kPa) while stirring at 800 RPM. The activator solution, followed by the pre-catalyst solution, was injected via syringe to the reactor at process conditions. Ethylene was allowed to enter (through the use of computer controlled solenoid valves) the autoclaves during polymerization to maintain reactor gauge pressure (+/−2 psig). Reactor temperature was monitored and typically maintained within +/−1° C. Polymerizations were halted by addition of approximately 50 psi $O_2$/Ar (5 mole % $O_2$) gas mixture to the autoclave for approximately 30 seconds. The polymerizations were quenched after a predetermined cumulative amount of ethylene had been added (maximum quench value in psid) or for a maximum of 30 minutes polymerization time. Afterwards, the reactors were cooled and vented. Polymers were isolated after the solvent was removed in-vacuo. Yields reported include total weight of polymer and residual catalyst. Catalyst activity is reported as grams of polymer per mmol transition metal compound per hour of reaction time (g/mmol·hr). Ethylene homopolymerization runs are summarized in Table 1, and ethylene/1-octene copolymerization runs are summarized in Table 2.

Propylene Polymerization (PP):

The reactor was prepared as described above, then heated to 40° C., and then purged with propylene gas at atmospheric pressure. For dimethylanilinium tetrakisperfluorophenylborate activated runs, isohexanes, liquid propylene (1.0 mL) and scavenger (TnOAl, 0.5 μmol) were added via syringe. The reactor was then brought to process temperature (70, 100, or 110° C.) while stirring at 800 RPM. The activator solution, followed by the pre-catalyst solution, were injected via syringe to the reactor at process conditions. Reactor temperature was monitored and typically maintained within +/−1° C. Polymerizations were halted by addition of approximately 50 psi $O_2$/Ar (5 mole % $O_2$) gas mixture to the autoclaves for approximately 30 seconds. The polymerizations were quenched based on a predetermined pressure loss of 8 psid (maximum quench value) or for a maximum of 30 or 45 minutes polymerization time (maximum reaction time in minutes). The reactors were cooled and vented. The polymers were isolated after the solvent was removed in-vacuo. The actual quench time (s) is reported as all polymerization quenched at 8 psid. Yields reported include total weight of polymer and residual catalyst. Catalyst activity is reported as grams of polymer per mmol transition metal compound per hour of reaction time (g/mmol·hr). Propylene homopolymerization examples are reported in Table 3 with additional characterization in Tables 4 and 5.

Ethylene Propylene Copolymerization (EP):

The reactor was prepared as described above, then heated to 40° C. and then purged with ethylene gas at atmospheric pressure. Ethylene pressure (125 psid) was then added to the reactor. Isohexanes (4.27 ml) and scavenger (TnOAl, 0.5 μmol) were added via syringe. The stirrers were then started and maintained at 800 RPM. Liquid propylene (0.5 ml) was then injected into the reactor. The reactor was then brought to process temperature (80° C.). The activator solution, followed by the pre-catalyst solution, was injected via syringe to the reactor at process conditions. Reactor temperature was monitored and typically maintained within +/−1° C. of 80° C. Polymerizations were halted by addition of approximately 50 psi $O_2$/Ar (5 mole % $O_2$) gas mixture to the autoclaves for approximately 30 seconds. The polymerizations were quenched based on a predetermined pressure loss of approximately 4 psi or for a maximum of 30 minutes polymerization time. The reactors were cooled and vented. The polymer was isolated after the solvent was removed in-vacuo. The quench time (s) is reported in Table 6 for each run. Yields reported include total weight of polymer and residual catalyst. Catalyst activity is reported as grams of polymer per mmol transition metal compound per hour of reaction time (g/mmol·r). Ethylene/propylene copolymerization examples are reported in Table 6.

Polymer Characterization

For analytical testing, polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 165° C. in a shaker oven for approximately 3 hours. The typical concentration of polymer in solution was between 0.1 to 0.9 mg/mL with a BHT concentration of 1.25 mg BHT/mL of TCB. Samples were cooled to 135° C. for testing.

High temperature size exclusion chromatography was performed using an automated "Rapid GPC" system as described in U.S. Pat. Nos. 6,491,816; 6,491,823; 6,475,391; 6,461,515; 6,436,292; 6,406,632; 6,175,409; 6,454,947; 6,260,407; and 6,294,388; each of which is incorporated herein by reference. Molecular weights (weight average molecular weight (Mw) and number average molecular weight (Mn)) and molecular weight distribution (MWD=Mw/Mn), which is also sometimes referred to as the polydispersity (PDI) of the polymer, were measured by Gel Permeation Chromatography using a Symyx Technology GPC equipped with evaporative light scattering detector (ELSD) and calibrated using polystyrene standards (Polymer Laboratories: Polystyrene Calibration Kit S-M-10: Mp (peak Mw) between 5000 and 3,390,000). Samples (250 µL of a polymer solution in TCB were injected into the system) were run at an eluent flow rate of 2.0 mL/minute (135° C. sample temperatures, 165° C. oven/columns) using three Polymer Laboratories: PLgel 10 µm Mixed-B 300×7.5 mm columns in series. No column spreading corrections were employed. Numerical analyses were performed using Epoch™ software available from Symyx Technologies. The molecular weights (Mw, Mn, and PDI=Mw/Mn) obtained are relative to linear polystyrene standards and are reported in Tables 1, 2, and 3.

Differential Scanning Calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./minute and then cooled at a rate of 50° C./minute. Melting points were collected during the heating period. The results are reported in the Tables 1 and 2 under the heading, Tm (° C.). The polypropylenes produced (see Tables 3) are largely amorphous polyolefins with no recordable Tm.

Samples for infrared analysis were prepared by depositing the stabilized polymer solution onto a silanized wafer (Part number S10860, Symyx). By this method, approximately between 0.12 and 0.24 mg of polymer is deposited on the wafer cell. The samples were subsequently analyzed on a Brucker Equinox 55 FTIR spectrometer equipped with Pikes' MappIR specular reflectance sample accessory. Spectra, covering a spectral range of 5000 cm$^{-1}$ to 500 cm$^{-1}$, were collected at a 2 cm$^{-1}$ resolution with 32 scans.

For ethylene-1-octene copolymers, the wt % octene in the copolymer was determined via measurement of the methyl deformation band at ~1375 cm$^{-1}$. The peak height of this band was normalized by the combination and overtone band at ~4321 cm$^{-1}$, which corrects for path length differences. The normalized peak height was correlated to individual calibration curves from $^1$H NMR data to predict the wt % octene content within a concentration range of ~2 to 35 wt % for octene. Typically, R$^2$ correlations of 0.98 or greater are achieved. These numbers are reported in Table 2 under the heading C8 wt %).

For ethylene-propylene copolymers, the wt. % ethylene is determined via measurement of the methylene rocking band (~770 cm$^{-1}$ to 700 cm$^{-1}$). The peak area of this band is normalized by sum of the band areas of the combination and overtone bands in the 4500 cm$^{-1}$ to 4000 cm$^{-1}$ range. The normalized band area is then correlated to a calibration curve from $^{13}$C NMR data to predict the wt. % ethylene within a concentration range of approx. 5 to 40 wt. %. Typically, R$^2$ correlations of 0.98 or greater are achieved. These numbers are reported in Table 6 under the heading C2 wt. %.

For some samples, polymer end-group analysis was determined by $^1$H NMR using a Varian Unity+400 MHz instrument run with a single 30° flip angle, RF pulse. 120 pulses with a delay of 8 seconds between pulses were signal averaged. The polymer sample was dissolved in heated d$_2$-1,1,2,2-tetrachloroethane and signal collection took place at 120° C. Vinylenes were measured as the number of vinylenes per 1000 carbon atoms using the resonances between 5.5-5.31 ppm. Trisubstituted end-groups ("trisubs") were measured as the number of trisubstituted groups per 1000 carbon atoms using the resonances between 5.3-4.85 ppm, by difference from vinyls. Vinyl end-groups were measured as the number of vinyls per 1000 carbon atoms using the resonances between 5.9-5.65 and between 5.3-4.85 ppm. Vinylidene end-groups were measured as the number of vinylidenes per 1000 carbon atoms using the resonances between 4.85-4.65 ppm. The values reported in Table 4 are % vinylene, % trisubstituted (% trisub), % vinyl and % vinylidene where the percentage is relative to the total olefinic unsaturation per 1000 carbon atoms.

$^{13}$C NMR spectroscopy was used to characterize some polypropylene polymer samples produced in experiments reported in Table 3. The $^{13}$C NMR data are reported in Table 5. Unless otherwise indicated the polymer samples for $^{13}$C NMR spectroscopy were dissolved in d$_2$-1,1,2,2-tetrachloroethane and the samples were recorded at 125° C. using a NMR spectrometer with a $^{13}$C NMR frequency of 150 MHz. Polymer resonance peaks are referenced to mmmm=21.8 ppm. Calculations involved in the characterization of polymers by NMR follow the work of F. A. Bovey in "Polymer Conformation and Configuration" Academic Press, New York 1969 and J. Randall in "Polymer Sequence Determination, Carbon-13 NMR Method", Academic Press, New York, 1977.

The stereodefects measured as "stereo defects/10,000 monomer units" are calculated from the sum of the intensities of mmrr, mmrm+rmmr, and rmrm resonance peaks times 5000. The intensities used in the calculations are normalized to the total number of monomers in the sample. Methods for measuring 2.1 regio defects/10,000 monomers and 1.3 regio defects/10,000 monomers follow standard methods. Additional references include Grassi, A. et. al. *Macromolecules*, 1988, 21, 617-622 and Busico et. al. *Macromolecules*, 1994, 27, 7538-7543. The average meso run length=10000/[(stereo defects/10000 C)+(2,1-regio defects/10000 C)+(1,3-regio-defects/10000 C)].

Polymerization results are collected in Tables 1, 2, 3, 4, and 5 below. "Ex#" stands for example number. Under the Ex# column heading, the following abbreviations are defined: PE=polyethylene, EO=ethylene-1-octene copolymer, PP=polypropylene, CPE=comparative polyethylene, CEO=comparative ethylene-1-octene copolymer, CPP=comparative polypropylene. Examples starting with a "C" as in CPP and CPE are comparative examples. "Cat ID" identifies the pre-catalyst used in the experiment. Corresponding letters identifying the pre-catalyst are located in the synthetic experimental section. "Cat (µmol)" is the amount of pre-catalyst added to the reactor. For all experiments using borate activators, the molar ratio of activator:pre-catalyst was 1:1. T(° C.) is the polymerization temperature. "Yield" is polymer yield, and is not corrected for catalyst residue. "Quench time (s)" is the actual duration of the polymerization run in seconds. "Quench Value (psid)" for ethylene based polymerization runs is the set maximum amount of ethylene uptake (conversion) for the experiment. If a polymerization quench time is less than the maximum time set, then the polymerization ran until the set maximum value of ethylene uptake was reached. For propylene homopolymerization runs, quench value indicates the maximum set pressure loss (conversion) of propylene during the polymerization. Activity is reported at grams polymer per mmol of catalyst per hour.

GPC-SEC

Mw, Mn, and Mw/Mn are determined by using a High Temperature Size Exclusion Chromatograph (Polymer Laboratories), equipped with three in-line detectors, a differential refractive index detector (DRI), a light scattering (LS) detector, and a viscometer. Experimental details, including detector calibration, are described in: T. Sun, P. Brant, R. R. Chance, and W. W. Graessley, Macromolecules, Volume 34, Number 19, pp. 6812-6820, (2001), and references therein. Three Polymer Laboratories PLgel 10 μm Mixed-B LS columns are used. The nominal flow rate is 0.5 ml/min, and the nominal injection volume is 300 μL. The various transfer lines, columns, viscometer and differential refractometer (the DRI detector) are contained in an oven maintained at 145° C. Solvent for the experiment is prepared by dissolving 6 grams of butylated hydroxytoluene as an antioxidant in 4 liters of Aldrich reagent grade 1, 2, 4 trichlorobenzene (TCB). The TCB mixture is then filtered through a 0.1 μm Teflon filter. The TCB is then degassed with an online degasser before entering the Size Exclusion Chromatograph. Polymer solutions are prepared by placing dry polymer in a glass container, adding the desired amount of TCB, then heating the mixture at 160° C. with continuous shaking for about 2 hours. All quantities are measured gravimetrically. The TCB densities used to express the polymer concentration in mass/volume units are 1.463 g/ml at room temperature and 1.284 g/ml at 145° C. The injection concentration is from 0.5 to 2.0 mg/ml, with lower concentrations being used for higher molecular weight samples. Prior to running each sample the DRI detector and the injector are purged. Flow rate in the apparatus is then increased to 0.5 ml/minute, and the DRI is allowed to stabilize for 8 to 9 hours before injecting the first sample. The LS laser is turned on at least 1 to 1.5 hours before running the samples. The concentration, c, at each point in the chromatogram is calculated from the baseline-subtracted DRI signal, IDRI, using the following equation:

$$c = K_{DRI} I_{DRI}/(dn/dc)$$

where KDRI is a constant determined by calibrating the DRI, and (dn/dc) is the refractive index increment for the system. The refractive index, n=1.500 for TCB at 145° C. and λ=660 nm. Units on parameters throughout this description of the GPC-SEC method are such that concentration is expressed in g/cm3, molecular weight is expressed in g/mole, and intrinsic viscosity is expressed in dL/g.

The LS detector is a Wyatt Technology High Temperature DAWN HELEOS. The molecular weight, M, at each point in the chromatogram is determined by analyzing the LS output using the Zimm model for static light scattering (M. B. Huglin, LIGHT SCATTERING FROM POLYMER SOLUTIONS, Academic Press, 1971):

$$\frac{K_o c}{\Delta R(\theta)} = \frac{1}{MP(\theta)} + 2A_2 c$$

Here, ΔR(θ) is the measured excess Rayleigh scattering intensity at scattering angle θ, c is the polymer concentration determined from the DRI analysis, A$_2$ is the second virial coefficient, for purposes of this invention A$_2$=0.0006, (dn/dc) is the refractive index increment for the system. P(θ) is the form factor for a monodisperse random coil, and K$_o$ is the optical constant for the system:

$$K_o = \frac{4\pi^2 n^2 \left(\frac{dn}{dc}\right)^2}{\lambda^4 N_A}$$

where NA is Avogadro's number, and (dn/dc) is the refractive index increment for the system. The refractive index, n=1.500 for TCB at 145° C. and λ=660 nm.

A high temperature Viscotek Corporation viscometer, which has four capillaries arranged in a Wheatstone bridge configuration with two pressure transducers, is used to determine specific viscosity. One transducer measures the total pressure drop across the detector, and the other, positioned between the two sides of the bridge, measures a differential pressure. The specific viscosity, η$_s$, for the solution flowing through the viscometer is calculated from their outputs. The intrinsic viscosity, [η], at each point in the chromatogram is calculated from the following equation:

$$\eta_s = c[\eta] + 0.3(c[\eta])^2$$

where c is concentration and was determined from the DRI output.

The branching index (g'$_{vis}$) is calculated using the output of the SEC-DRI-LS-VIS method as follows. The average intrinsic viscosity, [η]$_{avg}$, of the sample is calculated by:

$$[\eta]_{avg} = \frac{\sum c_i [\eta]_i}{\sum c_i}$$

where the summations are over the chromatographic slices, i, between the integration limits.

The branching index g'vis is defined as:

$$g'vis = \frac{[\eta]_{avg}}{kM_v^\alpha}$$

where, for purpose of this invention and claims thereto, α=0.695 and k=0.000579 for linear ethylene polymers, α=0.705 k=0.000262 for linear propylene polymers, and α=0.695 and k=0.000181 for linear butene polymers. M$_v$ is the viscosity-average molecular weight based on molecular weights determined by LS analysis. See Macromolecules, 2001, 34, 6812-6820 and Macromolecules, 2005, 38, 7181-7183, for guidance on selecting a linear standard having similar molecular weight and comonomer content, and determining k coefficients and α exponents.

TABLE 1

PE Examples

| Ex# | Cat ID | Cat (μmol) | yield (g) | quench time (s) | Activity (g P/mmol cat · hr) | Mn | Mw | Mw/Mn | Tm (° C.) |
| --- | --- | --- | --- | --- | --- | --- | --- | --- | --- |
| PE-1 | A | 0.025 | 0.0942 | 13 | 1,051,535 | 1,424,148 | 2,634,981 | 1.85 | 132.7 |
| PE-2 | A | 0.025 | 0.0824 | 15 | 796,349 | 2,110,086 | 3,191,050 | 1.51 | 133.4 |
| PE-3 | A | 0.025 | 0.0964 | 12 | 1,119,484 | 1,875,890 | 3,026,295 | 1.61 | 131.9 |
| PE-4 | B | 0.025 | 0.0956 | 12 | 1,197,078 | 2,084,724 | 3,419,614 | 1.64 | 132.1 |
| PE-5 | B | 0.025 | 0.0926 | 16 | 818,061 | 1,899,984 | 3,459,165 | 1.82 | 133.4 |

TABLE 1-continued

PE Examples

| Ex# | Cat ID | Cat (µmol) | yield (g) | quench time (s) | Activity (g P/mmol cat · hr) | Mn | Mw | Mw/Mn | Tm (° C.) |
|---|---|---|---|---|---|---|---|---|---|
| PE-6 | B | 0.025 | 0.0914 | 19 | 707,613 | 2,081,871 | 3,335,367 | 1.60 | 132.2 |
| CPE-1 | C | 0.025 | 0.0913 | 40 | 328,680 | 1,267,877 | 2,047,756 | 1.62 | 134.7 |
| CPE-2 | C | 0.025 | 0.0294 | 1320 | 3,208 | 1,165,727 | 1,715,756 | 1.47 | 134.9 |
| CPE-3 | C | 0.025 | 0.0882 | 33 | 386,043 | 1,288,006 | 2,063,431 | 1.60 | 134.9 |
| CPE-4 | D | 0.025 | 0.0978 | 10 | 1,437,061 | 1,979,709 | 3,413,748 | 1.72 | 134.2 |
| CPE-6 | D | 0.025 | 0.0776 | 17 | 661,207 | 2,050,549 | 3,162,260 | 1.54 | 134.3 |
| CPE-7 | E | 0.030 | 0.0966 | 11 | 1,083,364 | 1,054,226 | 2,868,315 | 2.72 | 135.9 |
| CPE-8 | E | 0.030 | 0.0878 | 55 | 191,564 | 1,236,744 | 2,581,785 | 2.09 | 129.8 |
| CPE-9 | E | 0.030 | 0.0953 | 20 | 568,955 | 991,496 | 2,862,475 | 2.89 | 134.9 |

Total sovent volume: 5.0 ml toluene; quench pressure of 20 psi uptake

TABLE 2

EO Examples

| Ex# | Cat ID | Cat (µmol) | Pressure (psig) | Quench Value (psid) | Quench time (s) | yield (g) | Activity (g P/mmol cat · hr) | Mn | Mw | Mw/Mn | C8 (wt %) | Tm (° C.) |
|---|---|---|---|---|---|---|---|---|---|---|---|---|
| EO-1 | A | 0.025 | 75 | 20 | 206 | 0.1177 | 82,316 | 262,435 | 1,393,623 | 5.31 | 29.4 | 98.6 |
| EO-2 | A | 0.025 | 75 | 20 | 167 | 0.1199 | 103,325 | 238,475 | 1,454,229 | 6.10 | 33.8 | 83.9 |
| EO-3 | A | 0.025 | 75 | 20 | 166 | 0.1203 | 104,294 | 239,910 | 1,196,953 | 4.99 | 32.2 | 86.2 |
| EO-4 | A | 0.025 | 200 | 15 | 17 | 0.1835 | 1,536,279 | 622,224 | 1,560,758 | 2.51 | 16.4 | 104.1 |
| EO-5 | A | 0.025 | 200 | 15 | 32 | 0.1937 | 871,650 | 720,000 | 1,762,310 | 2.45 | 17.6 | 103.5 |
| EO-6 | A | 0.025 | 200 | 15 | 12 | 0.1870 | 2,189,268 | 622,207 | 1,579,191 | 2.54 | 15.3 | 105.6 |
| EO-7 | B | 0.025 | 75 | 20 | 149 | 0.1153 | 111,133 | 1,375,74 | 3,496,302 | 2.54 | 30.6 | 108.2 |
| EO-8 | B | 0.025 | 75 | 20 | 136 | 0.1220 | 128,892 | 384,273 | 2,633,127 | 6.85 | 35.3* | 84.7 |
| EO-9 | B | 0.025 | 75 | 20 | 168 | 0.1239 | 106,453 | 194,282 | 822,800 | 4.24 | 34.7 | 84.2 |
| EO-10 | B | 0.025 | 200 | 15 | 24 | 0.1863 | 1,136,746 | 394,939 | 1,349,003 | 3.42 | 19.8 | 100.0 |
| EO-11 | B | 0.025 | 200 | 15 | 26 | 0.2028 | 1,114,626 | 424,547 | 1,479,876 | 3.49 | 17.8 | 100.2 |
| EO-12 | B | 0.025 | 200 | 15 | 21 | 0.1959 | 1,356,231 | 479,622 | 1,379,324 | 2.88 | 17.7 | 102.8 |
| CEO-1 | C | 0.025 | 75 | 20 | 137 | 0.1200 | 126,501 | 155,841 | 522,277 | 3.35 | 30.1 | 94.5 |
| CEO-2 | C | 0.025 | 75 | 20 | 185 | 0.1126 | 87,835 | 126,592 | 452,869 | 3.58 | 30.6 | 94.8 |
| CEO-3 | C | 0.025 | 75 | 20 | 190 | 0.1161 | 88,084 | 138,247 | 436,637 | 3.16 | 31.5 | 94.5 |
| CEO-4 | C | 0.025 | 200 | 15 | 38 | 0.1915 | 725,684 | 466,942 | 998,128 | 2.14 | 12.5 | 112.7 |
| CEO-5 | C | 0.025 | 200 | 15 | 45 | 0.1847 | 592,356 | 429,282 | 898,455 | 2.09 | 11.7 | 110.7 |
| CEO-6 | C | 0.025 | 200 | 15 | 42 | 0.1943 | 666,171 | 406,761 | 933,668 | 2.30 | 15.1 | 113.2 |
| CEO-7 | D | 0.025 | 75 | 20 | 190 | 0.1261 | 95,722 | 254,763 | 1,006,754 | 3.95 | 34.1 | 87.0 |
| CEO-8 | D | 0.025 | 75 | 20 | 167 | 0.1251 | 107,742 | | | | 32.4 | 81.2 |
| CEO-9 | D | 0.025 | 75 | 20 | 155 | 0.1204 | 111,639 | 391,721 | 1,216,467 | 3.11 | 29.6 | 98.7 |
| CEO-10 | D | 0.025 | 200 | 15 | 37 | 0.1921 | 755,803 | 731,114 | 1,679,638 | 2.30 | 16.8 | 102.3 |
| CEO-11 | D | 0.025 | 200 | 15 | 15 | 0.1618 | 1,606,841 | 872,283 | 1,642,255 | 1.88 | 14.4 | 101.3 |
| CEO-12 | D | 0.025 | 200 | 15 | 22 | 0.1700 | 1,133,333 | 607,788 | 1,495,798 | 2.46 | 17.1 | 104.6 |
| CEO-13 | E | 0.030 | 75 | 20 | 116 | 0.1338 | 137,938 | 39,555 | 1,050,457 | 26.56 | 25.5 | 111.1 |
| CEO-14 | E | 0.030 | 75 | 20 | 116 | 0.1354 | 139,828 | 15,379 | 866,138 | 56.32 | 34.6 | 111.4 |
| CEO-15 | E | 0.030 | 75 | 20 | 111 | 0.1318 | 143,131 | 31,864 | 608,194 | 19.09 | 31.4 | 110.1 |
| CEO-16 | E | 0.030 | 200 | 15 | 31 | 0.2237 | 880,131 | 35,453 | 524,780 | 14.80 | 30.3 | |
| CEO-17 | E | 0.030 | 200 | 15 | 50 | 0.2309 | 554,160 | 34,229 | 798,568 | 23.33 | 27.1 | |
| CEO-18 | E | 0.030 | 200 | 15 | 62 | 0.2292 | 446,494 | 18,000 | 621,697 | 34.54 | 30.1 | |

Total solvent volume: 4.9 ml toluene.
*Outside calibration range.

TABLE 3

PP examples

| Ex# | Cat ID | Cat (µmol) | Isohexane (uL) | Toluene (uL) | T (C) | Max Rxn Time (min) | quench time (s) | yield (g) | Activity (g P/mmol cat · hr) | Mn | Mw | Mw/Mn |
|---|---|---|---|---|---|---|---|---|---|---|---|---|
| PP-1 | A | 0.04 | 3810 | 290 | 70 | 30 | 48 | 0.2438 | 453,347 | 83,624 | 137,954 | 1.65 |
| PP-2 | A | 0.04 | 3810 | 290 | 70 | 30 | 56 | 0.2753 | 444,032 | 85,151 | 144,988 | 1.70 |
| PP-3 | A | 0.04 | 3810 | 290 | 70 | 30 | 50 | 0.2538 | 455,020 | 86,254 | 143,125 | 1.66 |
| PP-4 | A | 0.04 | 3810 | 290 | 100 | 30 | 69 | 0.1548 | 202,795 | 38,487 | 60,404 | 1.57 |
| PP-5 | A | 0.04 | 3810 | 290 | 100 | 30 | 71 | 0.1497 | 190,566 | 37,002 | 57,855 | 1.56 |
| PP-6 | A | 0.04 | 3810 | 290 | 100 | 30 | 71 | 0.1483 | 186,933 | 35,653 | 55,936 | 1.57 |
| PP-7 | B | 0.04 | 3810 | 290 | 70 | 30 | 52 | 0.2483 | 430,578 | 92,313 | 150,999 | 1.64 |
| PP-8 | B | 0.04 | 3810 | 290 | 70 | 30 | 51 | 0.2248 | 395,930 | 94,929 | 155,552 | 1.64 |
| PP-9 | B | 0.04 | 3810 | 290 | 70 | 30 | 52 | 0.2453 | 424,558 | 93,805 | 152,317 | 1.62 |

TABLE 3-continued

PP examples

| Ex# | Cat ID | Cat (μmol) | Isohexane (uL) | Toluene (uL) | T (C) | Max Rxn Time (min) | quench time (s) | yield (g) | Activity (g P/mmol cat · hr) | Mn | Mw | Mw/Mn |
|---|---|---|---|---|---|---|---|---|---|---|---|---|
| PP-10 | B | 0.04 | 3810 | 290 | 100 | 30 | 79 | 0.1248 | 142,719 | 41,631 | 63,994 | 1.54 |
| PP-11 | B | 0.04 | 3810 | 290 | 100 | 30 | 97 | 0.1100 | 102,484 | 36,799 | 56,980 | 1.55 |
| PP-12 | B | 0.04 | 3810 | 290 | 100 | 30 | 68 | 0.1397 | 185,716 | 42,511 | 65,536 | 1.54 |
| CPP-1 | C | 0.04 | 3810 | 290 | 70 | 30 | 100 | 0.1528 | 137,383 | 96,410 | 143,858 | 1.49 |
| CPP-2 | C | 0.04 | 3810 | 290 | 70 | 30 | 100 | 0.1631 | 147,232 | 102,111 | 153,300 | 1.50 |
| CPP-3 | C | 0.04 | 3810 | 290 | 70 | 30 | 103 | 0.1671 | 146,152 | 103,893 | 153,962 | 1.48 |
| CPP-4 | C | 0.04 | 3810 | 290 | 100 | 30 | 231 | 0.0811 | 31,556 | 35,304 | 52,951 | 1.50 |
| CPP-5 | C | 0.04 | 3810 | 290 | 100 | 30 | 218 | 0.0831 | 34,339 | 35,569 | 53,504 | 1.50 |
| CPP-6 | D | 0.04 | 3810 | 290 | 70 | 30 | 60 | 0.2040 | 305,491 | 127,716 | 205,001 | 1.61 |
| CPP-7 | D | 0.04 | 3810 | 290 | 70 | 30 | 56 | 0.1988 | 322,378 | 135,928 | 217,014 | 1.60 |
| CPP-8 | D | 0.04 | 3810 | 290 | 70 | 30 | 73 | 0.2238 | 277,056 | 127,350 | 206,429 | 1.62 |
| CPP-9 | D | 0.04 | 3810 | 290 | 100 | 30 | 80 | 0.1153 | 129,389 | 53,786 | 81,785 | 1.52 |
| CPP-10 | D | 0.04 | 3810 | 290 | 100 | 30 | 111 | 0.1144 | 92,673 | 47,212 | 72,285 | 1.53 |
| CPP-11 | D | 0.04 | 3810 | 290 | 100 | 30 | 90 | 0.1104 | 110,400 | 46,456 | 72,369 | 1.56 |
| PP-13 | A | 0.10 | 3790 | 310 | 100 | 45 | 30 | 0.1906 | 225,711 | 24,394 | 42,600 | 1.75 |
| PP-14 | A | 0.10 | 3790 | 310 | 100 | 45 | 36 | 0.2115 | 210,331 | 23,187 | 41,483 | 1.79 |
| PP-15 | A | 0.10 | 3790 | 310 | 100 | 45 | 33 | 0.1924 | 209,257 | 23,258 | 40,400 | 1.74 |
| PP-16 | A | 0.10 | 3790 | 310 | 100 | 45 | 31 | 0.2087 | 243,146 | 23,950 | 42,895 | 1.79 |
| PP-17 | A | 0.15 | 3685 | 415 | 110 | 45 | 28 | 0.1979 | 169,629 | 14,870 | 26,989 | 1.81 |
| PP-18 | A | 0.15 | 3685 | 415 | 110 | 45 | 25 | 0.1983 | 194,253 | 14,936 | 27,046 | 1.81 |
| PP-19 | A | 0.15 | 3685 | 415 | 110 | 45 | 30 | 0.2039 | 160,974 | 15,477 | 28,328 | 1.83 |
| PP-20 | A | 0.15 | 3685 | 415 | 110 | 45 | 28 | 0.2056 | 175,601 | 15,106 | 27,729 | 1.84 |
| PP-21 | B | 0.10 | 3790 | 310 | 100 | 45 | 24 | 0.1493 | 227,746 | 26,367 | 43,673 | 1.66 |
| PP-22 | B | 0.10 | 3790 | 310 | 100 | 45 | 29 | 0.1683 | 210,375 | 27,804 | 45,927 | 1.65 |
| PP-23 | B | 0.10 | 3790 | 310 | 100 | 45 | 30 | 0.1663 | 196,934 | 28,632 | 47,688 | 1.67 |
| PP-24 | B | 0.10 | 3790 | 310 | 100 | 45 | 33 | 0.1826 | 199,805 | 27,246 | 46,413 | 1.70 |
| PP-25 | B | 0.15 | 3685 | 415 | 110 | 45 | 23 | 0.1676 | 174,887 | 18,884 | 32,146 | 1.70 |
| PP-26 | B | 0.15 | 3685 | 415 | 110 | 45 | 23 | 0.1715 | 178,957 | 18,435 | 31,141 | 1.69 |
| PP-27 | B | 0.15 | 3685 | 415 | 110 | 45 | 35 | 0.1754 | 119,591 | 21,533 | 35,988 | 1.67 |
| PP-28 | B | 0.15 | 3685 | 415 | 110 | 45 | 28 | 0.1943 | 166,543 | 18,481 | 32,415 | 1.75 |
| CPP-12 | C | 0.10 | 3790 | 310 | 100 | 45 | 62 | 0.1375 | 79,839 | 24,606 | 39,337 | 1.60 |
| CPP-13 | C | 0.10 | 3790 | 310 | 100 | 45 | 72 | 0.1342 | 66,914 | 24,469 | 39,167 | 1.60 |
| CPP-14 | C | 0.10 | 3790 | 310 | 100 | 45 | 54 | 0.1336 | 89,067 | 24,466 | 39,306 | 1.61 |
| CPP-15 | C | 0.10 | 3790 | 310 | 100 | 45 | 64 | 0.1441 | 81,694 | 24,892 | 40,137 | 1.61 |
| CPP-16 | C | 0.15 | 3685 | 415 | 110 | 45 | 63 | 0.1310 | 49,590 | 16,771 | 27,255 | 1.63 |
| CPP-17 | C | 0.15 | 3685 | 415 | 110 | 45 | 55 | 0.1456 | 64,117 | 15,103 | 25,350 | 1.68 |
| CPP-18 | C | 0.15 | 3685 | 415 | 110 | 45 | 53 | 0.1410 | 64,335 | 15,380 | 25,136 | 1.63 |
| CPP-19 | C | 0.15 | 3685 | 415 | 110 | 45 | 45 | 0.1397 | 74,507 | 16,546 | 26,787 | 1.62 |
| CPP-20 | D | 0.10 | 3790 | 310 | 100 | 45 | 40 | 0.1745 | 156,269 | 31,976 | 52,920 | 1.66 |
| CPP-21 | D | 0.10 | 3790 | 310 | 100 | 45 | 47 | 0.1968 | 149,784 | 33,027 | 56,264 | 1.70 |
| CPP-22 | D | 0.10 | 3790 | 310 | 100 | 45 | 30 | 0.1561 | 184,855 | 34,152 | 56,228 | 1.65 |
| CPP-23 | D | 0.10 | 3790 | 310 | 100 | 45 | 38 | 0.1556 | 146,639 | 33,521 | 56,407 | 1.68 |
| CPP-24 | D | 0.15 | 3685 | 415 | 110 | 45 | 38 | 0.1869 | 119,298 | 19,626 | 34,407 | 1.75 |
| CPP-25 | D | 0.15 | 3685 | 415 | 110 | 45 | 37 | 0.1979 | 130,126 | 20,996 | 36,743 | 1.75 |
| CPP-26 | D | 0.15 | 3685 | 415 | 110 | 45 | 36 | 0.1845 | 124,382 | 19,831 | 35,169 | 1.77 |
| CPP-27 | D | 0.15 | 3685 | 415 | 110 | 45 | 29 | 0.1782 | 145,966 | 21,858 | 37,617 | 1.72 |

TABLE 4

$^1$H NMR data for polypropylenes

| Ex# | Cat ID | T (C) | total unsaturation/ 1000 C | % vinylene | % trisub | % vinyl | % vinylidene |
|---|---|---|---|---|---|---|---|
| PP-14 | A | 100 | 1.46 | 11.0 | 20.5 | 32.9 | 35.6 |
| PP-15 | A | 100 | 1.47 | 12.9 | 16.3 | 32.0 | 38.8 |
| PP-18 | A | 110 | 2.12 | 12.3 | 21.2 | 33.0 | 33.5 |
| PP-20 | A | 110 | 1.96 | 11.2 | 20.9 | 33.2 | 34.7 |
| PP-21 | B | 100 | 1.41 | 11.3 | 22.7 | 29.8 | 36.2 |
| PP-23 | B | 100 | 1.12 | 9.8 | 16.1 | 33.0 | 41.1 |
| PP-25 | B | 110 | 1.93 | 10.4 | 24.9 | 31.1 | 33.7 |
| PP-28 | B | 110 | 1.09 | 9.2 | 14.7 | 33.9 | 42.2 |
| CPP-12 | C | 100 | 1.23 | 31.7 | 14.6 | 22.8 | 30.9 |
| CPP-13 | C | 100 | 1.27 | 26.8 | 18.1 | 22.0 | 33.1 |
| CPP-16 | C | 110 | 2.03 | 21.2 | 25.1 | 24.1 | 29.6 |
| CPP-19 | C | 110 | 1.98 | 24.2 | 22.7 | 23.2 | 29.8 |
| CPP-20 | D | 100 | 1.12 | 10.7 | 18.8 | 32.1 | 38.4 |
| CPP-21 | D | 100 | 1.15 | 9.6 | 20.0 | 31.3 | 39.1 |
| CPP-26 | D | 110 | 1.93 | 11.9 | 22.8 | 33.7 | 31.6 |
| CPP-27 | D | 110 | 1.44 | 14.6 | 14.6 | 32.6 | 38.2 |

TABLE 5

13C NMR data for polypropylenes

| Ex# | Cat ID | T (C) | m | r | mmmm | mmmr | rmmr | mmrr | mmrm + rmrr |
|---|---|---|---|---|---|---|---|---|---|
| PP-3 | A | 70 | 0.4318 | 0.5682 | 0.0455 | 0.0892 | 0.0612 | 0.1399 | 0.2220 |
| PP-4 | A | 100 | 0.4132 | 0.5868 | 0.0324 | 0.0766 | 0.0608 | 0.1239 | 0.2368 |
| PP-7 | B | 70 | 0.4918 | 0.5082 | 0.0822 | 0.1185 | 0.0599 | 0.1643 | 0.1995 |
| PP-12 | B | 100 | 0.4517 | 0.5483 | 0.0552 | 0.1034 | 0.0552 | 0.1448 | 0.2138 |
| CPP-3 | C | 70 | 0.4119 | 0.5881 | 0.0326 | 0.0809 | 0.0561 | 0.1384 | 0.2272 |
| CPP-8 | D | 70 | 0.4082 | 0.5918 | 0.0297 | 0.0742 | 0.0594 | 0.1224 | 0.2412 |

| Ex# | rmmm | rrrr | mrrr | mrrm | stereo defects/ 10000 monomer | 2,1-regio defects/ 10000 monomer | % $(CH_2)_2$ | ave. meso run length |
|---|---|---|---|---|---|---|---|---|
| PP-3 | 0.1101 | 0.1154 | 0.1399 | 0.0769 | 2344 | 3.3 | 6.5 | 4.26 |
| PP-4 | 0.1263 | 0.1105 | 0.1539 | 0.0789 | 2435 | 3.8 | 7.6 | 4.10 |
| PP-7 | 0.0986 | 0.0739 | 0.1115 | 0.0915 | 2293 | 3.6 | 7.1 | 4.35 |
| PP-12 | 0.1172 | 0.0828 | 0.1241 | 0.1034 | 2379 | 4.2 | 8.3 | 4.20 |
| CPP-3 | 0.1188 | 0.1005 | 0.1423 | 0.1031 | 2409 | 4.7 | 9.4 | 4.14 |
| CPP-8 | 0.1262 | 0.1132 | 0.1577 | 0.0761 | 2440 | 3.6 | 7.2 | 4.09 |

TABLE 6

EP examples

| Ex# | Cat ID | quench time (s) | yield (g) | Activity (g P/ mmol cat · hr) | Mn | Mw | Mz | Mw/ Mn | C2 (wt %) |
|---|---|---|---|---|---|---|---|---|---|
| EP-1 | A | 30 | 0.1796 | 2,155,200 | 126,710 | 461,633 | 1,763,888 | 3.64 | 51.2 |
| EP-2 | A | 32 | 0.1798 | 2,022,750 | 153,036 | 443,776 | 1,493,597 | 2.90 | 51.3 |
| EP-3 | A | 39 | 0.1668 | 1,539,692 | 176,224 | 473,466 | 1,475,285 | 2.69 | 48.4 |
| EP-7 | B | 21 | 0.165 | 2,828,571 | 156,978 | 400,593 | 1,249,185 | 2.55 | 49.1 |
| EP-8 | B | 25 | 0.1894 | 2,727,360 | 112,838 | 379,266 | 1,272,844 | 3.36 | 43.6 |
| EP-9 | B | 26 | 0.1766 | 2,445,231 | 188,501 | 438,190 | 1,301,067 | 2.32 | 45.4 |
| CEP-1 | C | 37 | 0.1689 | 1,643,351 | 174,082 | 456,424 | 1,337,574 | 2.62 | 59.7* |
| CEP-2 | C | 37 | 0.168 | 1,634,595 | 152,734 | 450,719 | 1,561,478 | 2.95 | 56.4* |
| CEP-3 | C | 20 | 0.1161 | 2,089,800 | 240,514 | 541,954 | 1,433,144 | 2.25 | 56.9* |
| CEP-7 | D | 38 | 0.1855 | 1,757,368 | 145,553 | 454,895 | 1,474,093 | 3.13 | 49.2 |
| CEP-8 | D | 36 | 0.163 | 1,630,000 | 200,292 | 510,538 | 1,705,425 | 2.55 | 52.9 |
| CEP-9 | D | 38 | 0.1834 | 1,737,474 | 153,199 | 461,388 | 1,439,115 | 3.01 | 48.4 |

Total volume solvent (isohexane and toluene) 4.875 ml;
*Outside calibration range.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa. Likewise, the terms "comprising," "consisting essentially of," "consisting of" also include the product of the combinations of elements listed after the term.

What is claimed is:

1. A compound represented by the formula: $T_y Cp'_m MG_n X_q$ wherein: Cp' is a tetrahydroindacenyl group which is optionally substituted or unsubstituted, provided that when Cp' is tetrahydro-s-indacenyl: 1) the 3 and/or 4 positions are not aryl or substituted aryl, 2) the 3 position is not directly bonded to a group 15 or 16 heteroatom, 3) there are no additional rings fused to the tetrahydroindacenyl ligand, 4) T is not bonded to the 2-position, and 5) the 5, 6, or 7-position is geminally disubstituted;

M is a group 3, 4, 5, or 6 transition metal;

G is a heteroatom group represented by the formula $JR^i_z$ where J is N, P, O or S, $R^i$ is a $C_1$ to $C_{20}$ hydrocarbyl group, and z is 1 or 2;

T is a bridging group;

y is 0 or 1;

X is a leaving group;

m=1;

n=1, 2 or 3;

q=1, 2 or 3; and the sum of m+n+q is equal to the oxidation state of the transition metal.

2. A compound represented by the formula (I):

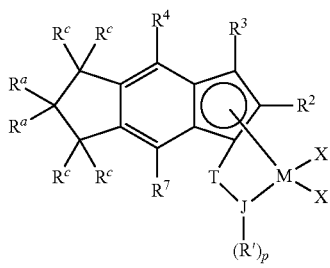

where:
M is a group 4 metal;
J is N, O, S or P;
p is 1 when J is N or P, and is 0 when J is O or S;
each $R^a$ is independently a $C_1$-$C_{10}$ alkyl;
each $R^c$ is independently hydrogen or a $C_1$-$C_{10}$ alkyl;
$R^2$, $R^3$, $R^4$, and $R^7$ are independently hydrogen, or a $C_1$-$C_{50}$ substituted or unsubstituted hydrocarbyl, halocarbyl or silylcarbyl, provided that: 1) $R^3$ and/or $R^4$ are not aryl or substituted aryl, 2) $R^3$ is not substituted with a group 15 or 16 heteroatom; and 3) that adjacent $R^4$, $R^c$, $R^a$, and or $R^7$ do not join together to form a fused ring system;
each R' is independently a $C_1$-$C_{100}$ substituted or unsubstituted hydrocarbyl, halocarbyl, or silylcarbyl;
T is $(CR^8R^9)_x$, $SiR^8R^9$ or $GeR^8R^9$ where x is 1 or 2, $R^8$ and $R^9$ are independently selected from hydrogen, or substituted or unsubstituted hydrocarbyl, halocarbyl, silylcarbyl and germylcarbyl and $R^8$ and $R^9$ are optionally bonded together to form a ring structure;
each X is, independently, a leaving group, or two Xs are joined and bound to the metal atom to form a metallocycle ring, or two Xs are joined to form a chelating ligand, a diene ligand, or an alkylidene.

3. A compound represented by the formula (III):

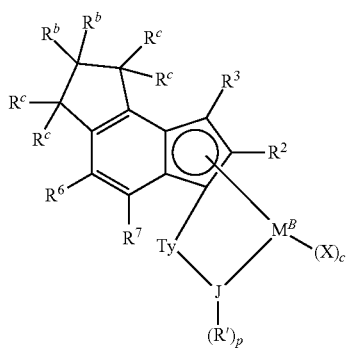

where M is group 3, 4, 5, or 6 transition metal;
B is the oxidation state of M, and is 3, 4, 5 or 6;
c is B-2;
J is N, O, S or P;
p is 1 when J is N or P, and is 0 when J is O or S;
$R^2$, $R^3$, $R^6$, and $R^7$, are independently hydrogen, or a $C_1$-$C_{50}$ substituted or unsubstituted hydrocarbyl, halocarbyl or silylcarbyl;
each $R^b$ and $R^c$ is independently $C_1$-$C_{10}$ alkyl, or hydrogen;

each R' is, independently, a $C_1$-$C_{100}$ substituted or unsubstituted hydrocarbyl, halocarbyl, silylcarbyl or germycarbyl;
T is $(CR^8R^9)_x$, $SiR^8R^9$ or $GeR^8R^9$ where x is 1 or 2, $R^8$ and $R^9$ are independently selected from hydrogen, substituted or unsubstituted hydrocarbyl, halocarbyl, silylcarbyl and germylcarbyl, and $R^8$ and $R^9$ may optionally be bonded together to form a ring structure;
each X is, independently, a leaving group, or two Xs are joined and bound to the metal atom to form a metallocycle ring, or two Xs are joined to form a chelating ligand, a diene ligand, or an alkylidene.

4. The catalyst compound of claim 1, wherein M is Ti.

5. The compound of claim 1, where J is N, and R' is methyl, ethyl, propyl, butyl, pentyl, hexyl, heptyl, octyl, nonyl, cyclooctyl, cyclododecyl, decyl, undecyl, dodecyl, adamantyl or an isomer thereof.

6. The catalyst compound of claim 2 wherein $R^2$, $R^3$, $R^4$, and/or $R^7$, are not aryl or substituted aryl.

7. The catalyst compound of claim 3, wherein $R^2$, $R^3$, $R^6$, and/or $R^7$, are not aryl or substituted aryl.

8. The compound of claim 2, wherein each $R^a$ is independently selected from the group consisting of methyl, ethyl, propyl, butyl, pentyl, hexyl and isomers thereof.

9. The compound of claim 1, wherein the sum of m+n+q is equal to 3, 4, 5, or 6.

10. The compound of claim 1, wherein the Cp' is tetrahydro-s-indacenyl and the 6 position is geminally disubstituted with two $C_1$-$C_{10}$ alkyl groups.

11. The compound of claim 1, wherein the Cp' is tetrahydro-s-indacenyl and the 6 position is geminally disubstituted with two alkyl groups selected from the group consisting of methyl, ethyl, propyl, butyl, pentyl, hexyl, heptyl, octyl, nonyl, decyl, undecyl, and dodecyl and isomers thereof.

12. The compound of claim 1, wherein the Cp' is tetrahydro-s-indacenyl and the 3 and 4 positions are not aryl or substituted aryl.

13. The compound of claim 3, wherein each $R^b$ is independently a $C_1$-$C_{10}$ alkyl.

14. The compound of claim 1, where J is N, and $R^i$ is t-butyl, hexyl, neopentyl, cyclohexyl, cyclooctyl, cyclododecyl, adamantyl, or norbornyl.

15. A composition comprising one or more of:
dimethylsilylene(2,6,6-trimethyl-1,5,6,7-tetrahydro-s-indacen-1-yl)(cyclododecylamido)M(R)$_2$;
dimethylsilylene(2,6,6-trimethyl-1,5,6,7-tetrahydro-s-indacen-1-yl)(t-butylamido)M(R)$_2$;
dimethylsilylene(6,6-dimethyl-1,5,6,7-tetrahydro-s-indacen-1-yl)(cyclododecylamido)M(R)$_2$;
dimethylsilylene (6,6-dimethyl-1,5,6,7-tetrahydro-s-indacen-1-yl)(t-butylamido)M(R)$_2$;
dimethylsilylene(2,7,7-trimethyl-3,6,7,8-tetrahydro-as-indacen-3-yl)(cyclododecylamido)M(R)$_2$;
dimethylsilylene(2,7,7-trimethyl-3,6,7,8-tetrahydro-as-indacen-3-yl)(t-butylamido)M(R)$_2$,
dimethylsilylene(7,7-dimethyl-3,6,7,8-tetrahydro-as-indacen-3-yl)(cyclododecylamido)M(R)$_2$;
dimethylsilylene(7,7-dimethyl-3,6,7,8-tetrahydro-as-indacen-3-yl)(t-butylamido)M(R)$_2$;
μ-(CH$_3$)$_2$Si(2,6,6-trimethyl-1,5,6,7-tetrahydro-s-indacen-1-yl)(1-adamantylamido)M(R)$_2$;
μ-(CH$_3$)$_2$Si(6,6-dimethyl-1,5,6,7-tetrahydro-s-indacen-1-yl)(1-adamantylamido)M(R)$_2$;
μ-(CH$_3$)$_2$Si(2-methyl-6,6-diethyl-1,5,6,7-tetrahydro-s-indacen-1-yl)(1-adamantylamido)M(R)$_2$;

μ-(CH₃)₂Si(6,6-diethyl-1,5,6,7-tetrahydro-s-indacen-1-yl)(1-adamantylamido)M(R)₂;
μ-(CH₃)₂Si(2,7,7-trimethyl-3,6,7,8-tetrahydro-as-indacen-3-yl)(1-adamantylamido)M(R)₂;
μ-(CH₃)₂Si(7,7-dimethyl-3,6,7,8-tetrahydro-as-indacen-3-yl)(1-adamantylamido)M(R)₂;
μ-(CH₃)₂Si(2-methyl-3,6,7,8-tetrahydro-as-indacen-3-yl)(1-adamantylamido)M(R)₂;
μ-(CH₃)₂Si(2-methyl-7,7-diethyl-3,6,7,8-tetrahydro-as-indacen-3-yl)(1-adamantylamido)M(R)₂;
μ-(CH₃)₂Si(7,7-diethyl-3,6,7,8-tetrahydro-as-indacen-3-yl)(1-adamantylamido)M(R)₂;
μ-(CH₃)₂Si(2,6,6-trimethyl-1,5,6,7-tetrahydro-s-indacen-1-yl)(t-butylamido)M(R)₂;
μ-(CH₃)₂Si(6,6-dimethyl-1,5,6,7-tetrahydro-s-indacen-1-yl)(t-butylamido)M(R)₂;
μ-(CH₃)₂Si(2-methyl-6,6-diethyl-1,5,6,7-tetrahydro-s-indacen-1-yl)(t-butylamido)M(R)₂;
μ-(CH₃)₂Si(6,6-diethyl-1,5,6,7-tetrahydro-s-indacen-1-yl)(t-butylamido)M(R)₂;
μ-(CH₃)₂Si(2,7,7-trimethyl-3,6,7,8-tetrahydro-as-indacen-3-yl)(t-butylamido)M(R)₂;
μ-(CH₃)₂Si(7,7-dimethyl-3,6,7,8-tetrahydro-as-indacen-3-yl)(t-butylamido)M(R)₂;
μ-(CH₃)₂Si(2-methyl-3,6,7,8-tetrahydro-as-indacen-3-yl)(t-butylamido)M(R)₂;
μ-(CH₃)₂Si(2-methyl-7,7-diethyl-3,6,7,8-tetrahydro-as-indacen-3-yl)(t-butylamido)M(R)₂;
μ-(CH₃)₂Si(7,7-diethyl-3,6,7,8-tetrahydro-as-indacen-3-yl)(t-butylamido)M(R)₂;
μ-(CH₃)₂Si(2,6,6-trimethyl-1,5,6,7-tetrahydro-s-indacen-1-yl)(cyclododecylamido)M(R)₂;
μ-(CH₃)₂Si(6,6-dimethyl-1,5,6,7-tetrahydro-s-indacen-1-yl)(cyclododecylamido)M(R)₂;
μ-(CH₃)₂Si(2-methyl-6,6-diethyl-1,5,6,7-tetrahydro-s-indacen-1-yl)(cyclododecylamido)M(R)₂;
μ-(CH₃)₂Si(6,6-diethyl-1,5,6,7-tetrahydro-s-indacen-1-yl)(cyclododecylamido)M(R)₂;
μ-(CH₃)₂Si(2,7,7-trimethyl-3,6,7,8-tetrahydro-as-indacen-3-yl)(cyclododecylamido)M(R)₂;
μ-(CH₃)₂Si(7,7-dimethyl-3,6,7,8-tetrahydro-as-indacen-3-yl)(cyclododecylamido)M(R)₂;
μ-(CH₃)₂Si(2-methyl-3,6,7,8-tetrahydro-as-indacen-3-yl)(cyclododecylamido)M(R)₂;
μ-(CH₃)₂Si(2-methyl-7,7-diethyl-3,6,7,8-tetrahydro-as-indacen-3-yl)(cyclododecylamido)M(R)₂;
μ-(CH₃)₂Si(7,7-diethyl-3,6,7,8-tetrahydro-as-indacen-3-yl)(cyclododecylamido)M(R)₂;
μ-(CH₂)₃Si(2,6,6-trimethyl-1,5,6,7-tetrahydro-s-indacen-1-yl)(t-butylamido)M(R)₂;
μ-(CH₂)₄Si(2,6,6-trimethyl-1,5,6,7-tetrahydro-s-indacen-1-yl)(t-butylamido)M(R)₂;
μ-(CH₂)₅Si(2,6,6-trimethyl-1,5,6,7-tetrahydro-s-indacen-1-yl)(t-butylamido)M(R)₂;
μ-(CH₃)₂C(2,6,6-trimethyl-1,5,6,7-tetrahydro-s-indacen-1-yl)(t-butylamido)M(R)₂;
μ-(CH₂)₃Si(2,6,6-trimethyl-1,5,6,7-tetrahydro-s-indacen-1-yl)(t-butylamido)M(R)₂;
μ-(CH₂)₄Si(2,6,6-trimethyl-1,5,6,7-tetrahydro-s-indacen-1-yl)(t-butylamido)M(R)₂;
μ-(CH₂)₅Si(2,6,6-trimethyl-1,5,6,7-tetrahydro-s-indacen-1-yl)(t-butylamido)M(R)₂;
μ-(CH₃)₂C(2,6,6-trimethyl-1,5,6,7-tetrahydro-s-indacen-1-yl)(t-butylamido)M(R)₂; and
μ-(CH₃)₂Si(2,6,6-trimethyl-1,5,6,7-tetrahydro-s-indacen-1-yl)(neopentylamido)M(R)₂;

where M is selected from a group consisting of Ti, Zr, and Hf and R is selected from halogen and $C_1$ to $C_5$ alkyl.

16. The compound of claim 3, wherein the compound is represented by the formula:

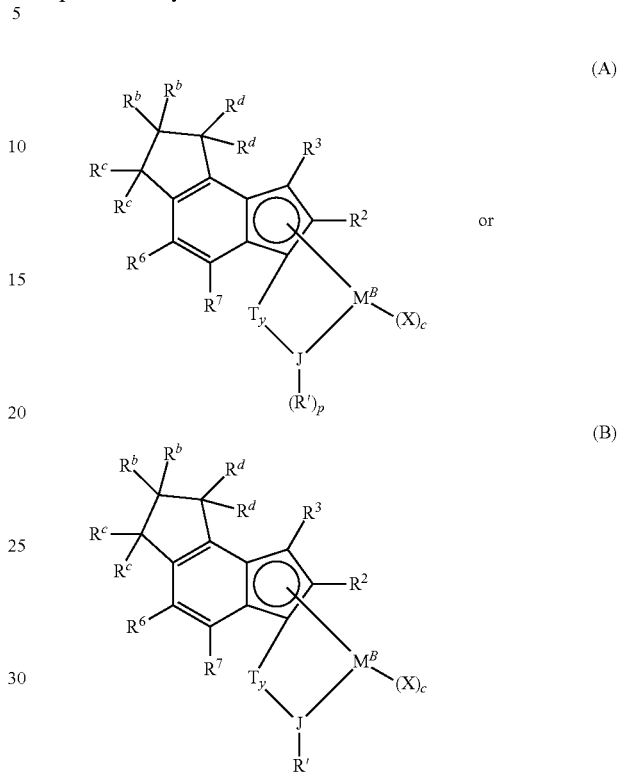

where M, B, c, J, p, $R^2$, $R^3$, $R^6$, $R^7$, R', T, y and X are as defined in claim 3 and each $R^b$, $R^c$, and $R^d$ is independently $C_1$-$C_{10}$ alkyl, or hydrogen, provided that both $R^b$, both $R^c$, or both $R^d$ are not hydrogen.

17. A catalyst system comprising the compound of claim 1 and an activator.

18. The catalyst system of claim 17, wherein the activator comprises a non-coordinating anion activator and/or an alumoxane.

19. The catalyst system of claim 17, where the catalyst system is supported.

20. A process to produce olefin polymer comprising contacting olefin monomer with the catalyst system of claim 17.

21. The process of claim 20, wherein the monomer comprises ethylene and/or propylene.

22. The process of claim 20, wherein the catalyst system comprises one catalyst compound.

23. The process of claim 20, wherein the process occurs at a temperature of from about 0° C. to about 300° C., at a pressure in the range of from about 0.35 MPa to about 16 MPa, and at a time up to 300 minutes.

24. The process of claim 20, wherein the monomer comprises two or more of ethylene, propylene, butene, pentene, hexene, heptene, octene, nonene, decene, undecene, or dodecene.

25. The process of claim 20, wherein the monomer comprises ethylene, propylene and 5-ethylidene-2-norbornene.

* * * * *